(12) United States Patent
Nolan

(10) Patent No.: US 11,859,240 B2
(45) Date of Patent: *Jan. 2, 2024

(54) METHODS OF IDENTIFYING MULTIPLE EPITOPES IN CELLS

(71) Applicant: Roche Sequencing Solutions, Inc., Pleasanton, CA (US)

(72) Inventor: Garry P. Nolan, Redwood City, CA (US)

(73) Assignee: ROCHE SEQUENCING SOLUTIONS, INC., Pleasanton, CA (US)

(*) Notice: Subject to any disclaimer, the term of this patent is extended or adjusted under 35 U.S.C. 154(b) by 107 days.

This patent is subject to a terminal disclaimer.

(21) Appl. No.: 18/102,056

(22) Filed: Jan. 26, 2023

(65) Prior Publication Data

US 2023/0167484 A1 Jun. 1, 2023

Related U.S. Application Data

(63) Continuation of application No. 17/951,008, filed on Sep. 22, 2022, now Pat. No. 11,732,290, which is a continuation of application No. 17/870,697, filed on Jul. 21, 2022, now Pat. No. 11,566,278, which is a continuation of application No. 16/795,203, filed on Feb. 19, 2020, now abandoned, which is a continuation of application No. 16/147,250, filed on Sep. 28, 2018, now Pat. No. 10,982,256, which is a
(Continued)

(51) Int. Cl.
*C12Q 1/68* (2018.01)
*C12Q 1/6806* (2018.01)
*C12Q 1/6816* (2018.01)
*C12Q 1/686* (2018.01)

(52) U.S. Cl.
CPC ........... *C12Q 1/6806* (2013.01); *C12Q 1/686* (2013.01); *C12Q 1/6816* (2013.01)

(58) Field of Classification Search
CPC ....................................................... C12Q 1/68
USPC .............................................................. 435/6.1
See application file for complete search history.

(56) References Cited

U.S. PATENT DOCUMENTS

| 4,568,649 A | 2/1986 | Bertoglio-matte |
| 4,988,617 A | 1/1991 | Landegren et al. |

(Continued)

FOREIGN PATENT DOCUMENTS

| CN | 103703143 | 4/2014 |
| DE | 10149786 | 7/2003 |

(Continued)

OTHER PUBLICATIONS

Brenner et al. In vitro cloning of complex mixtures of DNA on microbeads: physical separation of differentially expressed cDNAs] (2000) Proc. Natl. Acad. Set USA 97:1665 [Proc Natl Acad Sci U S A. Feb. 15, 2000;97(4):1665-70. doi: 10.1073/pnas.97.4.1665.*

(Continued)

*Primary Examiner* — Aaron A Priest
(74) *Attorney, Agent, or Firm* — James S. Keddie; Bozicevic, Field & Francis LLP

(57) ABSTRACT

The invention provides methods, compositions, kits and devices for the detection of target molecules. In some embodiments, the invention allows for multiplexed target molecule detection.

26 Claims, 13 Drawing Sheets

Related U.S. Application Data continuation of application No. 13/981,711, filed as application No. PCT/US2012/023411 on Jan. 31, 2012, now Pat. No. 10,144,950.

(60) Provisional application No. 61/444,067, filed on Feb. 17, 2011, provisional application No. 61/437,854, filed on Jan. 31, 2011.

(56) References Cited

U.S. PATENT DOCUMENTS

| | | | |
|---|---|---|---|
| 5,185,243 | A | 2/1993 | Ullman et al. |
| 5,242,794 | A | 9/1993 | Whiteley et al. |
| 5,494,810 | A | 2/1996 | Barany et al. |
| 5,831,012 | A | 11/1998 | Nilsson et al. |
| 5,858,732 | A | 1/1999 | Solomon et al. |
| 6,262,490 | B1 | 7/2001 | Hsu et al. |
| 6,350,579 | B1 | 2/2002 | Nelson |
| 6,582,938 | B1 | 6/2003 | Su et al. |
| 6,670,461 | B1 | 12/2003 | Wengel et al. |
| 6,723,510 | B2 | 4/2004 | Lubenow |
| 6,770,748 | B2 | 8/2004 | Imanishi et al. |
| 6,787,308 | B2 | 9/2004 | Balasubramanian et al. |
| 6,794,499 | B2 | 9/2004 | Wengel et al. |
| 6,830,936 | B2 | 12/2004 | Anderson et al. |
| 6,833,246 | B2 | 12/2004 | Balasubramanian |
| 6,897,023 | B2 | 5/2005 | Fu et al. |
| 6,969,488 | B2 | 11/2005 | Bridgham et al. |
| 7,294,298 | B2 | 11/2007 | Iijima |
| 7,294,503 | B2 | 11/2007 | Quake et al. |
| 7,378,280 | B2 | 5/2008 | Quake et al. |
| 7,393,655 | B2 | 7/2008 | Salon et al. |
| 7,473,767 | B2 | 1/2009 | Dimitrov |
| 7,919,237 | B2 | 4/2011 | Dimitrov et al. |
| 8,090,603 | B2 | 1/2012 | Payne et al. |
| 8,519,115 | B2 | 8/2013 | Webster et al. |
| 8,603,749 | B2 | 12/2013 | Gillevet |
| 8,697,363 | B2 | 4/2014 | Mir et al. |
| 8,986,926 | B2 | 3/2015 | Ferree et al. |
| 10,144,950 | B2 | 12/2018 | Nolan |
| 10,174,310 | B2 | 1/2019 | Nolan |
| 10,626,442 | B2 | 4/2020 | Nolan |
| 10,982,256 | B2 | 4/2021 | Nolan |
| 10,982,271 | B2 | 4/2021 | Bava et al. |
| 10,995,362 | B2 | 5/2021 | Dallett et al. |
| 11,214,794 | B2 | 1/2022 | Nolan |
| 11,512,341 | B1 | 11/2022 | Nolan |
| 11,560,585 | B2 | 1/2023 | Nolan |
| 2001/0041344 | A1 | 11/2001 | Sepetov et al. |
| 2002/0012930 | A1 | 1/2002 | Rothberg et al. |
| 2002/0192687 | A1 | 12/2002 | Mirkin et al. |
| 2003/0022207 | A1 | 1/2003 | Balasubramanian et al. |
| 2003/0044781 | A1 | 3/2003 | Korlach et al. |
| 2003/0050453 | A1 | 3/2003 | Sorge |
| 2003/0058629 | A1 | 3/2003 | Hirai et al. |
| 2003/0064398 | A1 | 4/2003 | Barnes |
| 2003/0068629 | A1 | 4/2003 | Rothberg et al. |
| 2003/0082551 | A1 | 5/2003 | Zarling |
| 2003/0100102 | A1 | 5/2003 | Rothberg et al. |
| 2003/0148344 | A1 | 8/2003 | Rothberg et al. |
| 2003/0219801 | A1 | 11/2003 | Lipshutz |
| 2003/0232348 | A1 | 12/2003 | Jones et al. |
| 2004/0106110 | A1 | 6/2004 | Balasubramanian et al. |
| 2004/0110153 | A1 | 6/2004 | Dong et al. |
| 2004/0248161 | A1 | 12/2004 | Rothberg et al. |
| 2005/0079510 | A1 | 4/2005 | Berka et al. |
| 2005/0100932 | A1 | 5/2005 | Lapidus et al. |
| 2005/0124022 | A1 | 6/2005 | Srinivasan et al. |
| 2005/0255491 | A1 | 11/2005 | Lee et al. |
| 2006/0002471 | A1 | 1/2006 | Lippincott et al. |
| 2006/0012784 | A1 | 1/2006 | Ulmer |
| 2006/0012793 | A1 | 1/2006 | Harris |
| 2006/0024678 | A1 | 2/2006 | Buzby |
| 2006/0024711 | A1 | 2/2006 | Lapidus et al. |
| 2006/0078909 | A1 | 4/2006 | Srinivasan et al. |
| 2006/0078937 | A1 | 4/2006 | Korlach et al. |
| 2006/0088872 | A1 | 4/2006 | Ahmadian et al. |
| 2006/0246475 | A1 | 11/2006 | Peterson et al. |
| 2006/0275923 | A1 | 12/2006 | Hammond |
| 2007/0072208 | A1 | 3/2007 | Drmanac |
| 2007/0166708 | A1 | 7/2007 | Dimitrov et al. |
| 2007/0298411 | A1* | 12/2007 | Choo ............... C12N 5/00 435/395 |
| 2008/0241820 | A1 | 10/2008 | Krutzik et al. |
| 2008/0269068 | A1 | 10/2008 | Church et al. |
| 2009/0005252 | A1 | 1/2009 | Drmanac et al. |
| 2009/0063206 | A1 | 3/2009 | Payne et al. |
| 2009/0220978 | A1 | 9/2009 | Dimitrov et al. |
| 2010/0047924 | A1 | 2/2010 | Webster et al. |
| 2010/0203543 | A1 | 8/2010 | Krutzik et al. |
| 2010/0240101 | A1 | 9/2010 | Lieberman et al. |
| 2010/0261026 | A1 | 10/2010 | Ferree et al. |
| 2010/0273159 | A1 | 10/2010 | Melo |
| 2010/0311598 | A1 | 12/2010 | Shapiro |
| 2011/0076690 | A1 | 3/2011 | Gumbrecht |
| 2011/0160078 | A1 | 6/2011 | Fodor et al. |
| 2011/0166034 | A1 | 7/2011 | Kwong |
| 2011/0166304 | A1 | 7/2011 | Zanthoff et al. |
| 2011/0195853 | A1 | 8/2011 | Kavusi et al. |
| 2011/0207134 | A1 | 8/2011 | Faham et al. |
| 2011/0263688 | A1 | 10/2011 | Barany |
| 2012/0100047 | A1 | 4/2012 | Brutler et al. |
| 2012/0270212 | A1 | 10/2012 | Rabinowitz |
| 2013/0274117 | A1 | 10/2013 | Church |
| 2013/0296194 | A1 | 11/2013 | Jacobson et al. |
| 2014/0186827 | A1 | 7/2014 | Pieprzyk et al. |
| 2015/0132743 | A1 | 5/2015 | Egido |
| 2015/0329852 | A1 | 11/2015 | Nolan |
| 2016/0138086 | A1 | 5/2016 | Seelig et al. |
| 2016/0251697 | A1 | 9/2016 | Nolan |
| 2017/0009278 | A1 | 1/2017 | Soderberg |
| 2017/0321251 | A1 | 11/2017 | Nolan |
| 2018/0089373 | A1 | 3/2018 | Matsuguchi et al. |
| 2018/0320241 | A1 | 11/2018 | Nolan |
| 2018/0333851 | A1 | 11/2018 | Lapham |
| 2019/0093146 | A1 | 3/2019 | Nolan |
| 2019/0093156 | A1 | 3/2019 | Bava et al. |
| 2019/0153513 | A1 | 5/2019 | Dallett et al. |
| 2019/0177717 | A1 | 6/2019 | Nolan |
| 2020/0157603 | A1 | 5/2020 | O'Huallachain et al. |
| 2020/0208197 | A1 | 7/2020 | Nolan |
| 2020/0362392 | A1 | 11/2020 | Nolan |
| 2021/0002733 | A1 | 1/2021 | Nolan |
| 2021/0040538 | A1 | 2/2021 | Nolan |
| 2022/0049286 | A1 | 2/2022 | Dallett et al. |
| 2022/0056515 | A1 | 2/2022 | Bava et al. |
| 2022/0364151 | A1 | 11/2022 | Nolan |

FOREIGN PATENT DOCUMENTS

| | | |
|---|---|---|
| DE | 10214395 | 10/2003 |
| DE | 10356937 | 7/2004 |
| DE | 10356837 | 6/2005 |
| DE | 102004009704 | 9/2005 |
| DE | 102004025744 | 12/2005 |
| DE | 102004025745 | 12/2005 |
| DE | 102004025746 | 12/2005 |
| DE | 102004025694 | 2/2006 |
| DE | 102004025695 | 2/2006 |
| DE | 102004025696 | 2/2006 |
| DE | 102006012317 | 1/2007 |
| EP | 0320308 | 6/1989 |
| EP | 0439182 | 7/1991 |
| EP | 1885876 | 2/2008 |
| JP | 2003-524419 | 8/2003 |
| JP | 2012-502625 | 2/2012 |
| JP | 2014-507141 | 3/2014 |
| JP | 2014-513916 | 6/2014 |
| WO | WO 90/01069 | 2/1990 |
| WO | WO 01/57268 | 8/2001 |
| WO | WO 01/61037 | 8/2001 |
| WO | WO 02/088382 | 11/2002 |
| WO | WO 03/020968 | 3/2003 |
| WO | WO 03/031947 | 4/2003 |

(56) References Cited

FOREIGN PATENT DOCUMENTS

| WO | WO 2005/010159 A2 | 2/2005 | |
|---|---|---|---|
| WO | WO 2005/044836 | 5/2005 | |
| WO | WO 2005/071110 | 8/2005 | |
| WO | WO 2005/123963 | 12/2005 | |
| WO | WO 2006/079049 | 7/2006 | |
| WO | WO 2007/076128 | 7/2007 | |
| WO | WO 2009/048530 | 4/2009 | |
| WO | WO 2010/032008 | 3/2010 | |
| WO | WO 2011/020247 A1 | 2/2011 | |
| WO | WO-2011020247 A1 * | 2/2011 | ......... C12N 15/1065 |
| WO | WO 2011/146942 A1 | 11/2011 | |
| WO | WO 2012/048341 | 4/2012 | |
| WO | WO 2012/083225 | 6/2012 | |
| WO | WO 2012/106385 | 8/2012 | |
| WO | WO 2012/108920 | 8/2012 | |
| WO | WO 2012/142242 | 10/2012 | |
| WO | WO 2013/137737 | 9/2013 | |
| WO | WO 2014026032 | 2/2014 | |
| WO | WO 2014/099744 | 6/2014 | |
| WO | WO 2018049926 | 3/2018 | |

OTHER PUBLICATIONS

Adams, et al. The genome sequence of *Drosophila melanogaster.* Science. Mar. 24, 2000;287(5461):2185-95.

Agasti, et al. Photocleavable DNA barcode-antibody conjugates allow sensitive and multiplexed protein analysis in single cells. J Amer Chem Soc ePub, Nov. 2, 2012, vol. 134, No. 45, pp. 18499-18502.

Boozer, et al. DNA directed protein immobilization on mixed ssDNA/oligo(ethylene glycol) self-assembled monolayers for sensitive biosensors. Anal Chem. Dec. 1, 2004;76(23):6967-72.

Casbon, et al. A method for counting PCR template molecules with application to next-generation sequencing. Nucleic Acids Res. Jul. 2011;39(12):e81. doi: 10.1093/nar/gkr217. Epub Apr. 13, 2011.

Chan, et al. Polytriazoles as copper(I)-stabilizing ligands in catalysis. Org Lett. Aug. 19, 2004;6(17):2853-5.

Constans, Beyond Sanger: Toward the $1,000 Genome—The Scientist—Magazine of the Life Sciences. The Scientist. Jun. 30, 2003; 17(13):36.

Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.

El-Sagheer, et al. Biocompatible artificial DNA linker that is read through by DNA polymerases and is functional in *Escherichia coli.* Proc Natl Acad Sci U S A. Jul. 12, 2011;108(28):11338-43. doi: 10.1073/pnas.1101519108. Epub Jun. 27, 2011.

El-Sagheer, et al. New strategy for the synthesis of chemically modified RNA constructs exemplified by hairpin and hammerhead ribozymes. Proc Natl Acad Sci U S A. Aug. 31, 2010;107(35):15329-34. doi: 10.1073/pnas.1006447107. Epub Aug. 16, 2010.

Fan, et al. Combinatorial labeling of single cells for gene expression cytometry. Science. Feb. 6, 2015;347(6222):1258367. doi: 10.1126/science.1258367.

Fredriksson, et al. Protein detection using proximity-dependent DNA ligation assays. Nature Biotechnology, Nature Publishing Group, New York, NY, US, vol. 20, May 1, 2002, pp. 473-477.

Garaj, et al. Graphene as a subnanometre trans-electrode membrane. Nature. Sep. 9, 2010;467(7312):190-3. doi: 10.1038/nature09379. Epub Aug. 18, 2010.

Gerrits, et al. Cellular barcoding tool for clonal analysis in the hematopoietic system. Blood. Apr. 1, 2010;115(13):2610-8. doi: 10.1182/blood-2009-06-229757. Epub Jan. 21, 2010.

Gierahn, et al. Seq-Well: portable, low-cost RNA sequencing of single cells at high throughput. Nature Methods 14.4 (2017): 395-398.

Gold. Oligonucleotides as research, diagnostic, and therapeutic agents. J Biol Chem. Jun. 9, 1995;270(23):13581-4.

Goldman, et al. Avidin: a natural bridge for quantum dot-antibody conjugates. J Am Chem Soc. 2002;124(22):6378-82.

Google Translation of WO-2018049926-A1 (English) (Year:2018).

Gullberg, et al. Cytokine detection by antibody-based proximity ligation. Proc Natl Acad Sci U S A. Jun. 1, 2004;101(22):8420-4. Epub May 21, 2004.

Herman, B. Resonance energy transfer microscopy. Methods Cell Biol 30 (1989): 219-243.

International search report and written opinion dated Jul. 14, 2016 for PCT Application No. PCTUS15/67147.

Jayasena. Aptamers: an emerging class of molecules that rival antibodies in diagnostics. Clin Chem. Sep. 1999;45(9):1628-50.

Jermutus, et al. Ligand binding of a ribosome-displayed protein detected in solution at the single molecule level by fluorescence correlation spectroscopy. Eur Biophys J. Jun. 2002;31(3): 179-84. Epub Jan. 30, 2002.

Klammer, et al. Modeling peptide fragmentation with dynamic Bayesian networks for peptide identification. Bioinformatics. Jul. 1, 2008;24(13):i348-56. doi: 10.1093/bioinformatics/btn189.

Klein et al., Droplet brocoding for signle-cell transcriptomics applied to embryonic stgem cells. Cell 161.5 (2015): 1187-1201.

Kopf, et al. Panorama ab microarray cell signaling kit: a unique tool for protein expression analysis. Proteomics, Wiley, vol. 5, No. 9, Jun. 1, 2005, pp. 2412-2416.

Kozlov, et al. Efficient strategies for the conjugation of oligonucleotides to antibodies enabling highly sensitive protein detection. Biopolymers. Apr. 5, 2004;73(5):621-30.

Lam et al., "The "One-Bead-One-Compound" Combinatorial Library Method", Chemical Reviews, 1997, 97(2): 411-448.

Lauring et al., Exploring the fitness landscape of an RNA virus by using a universal barcode microarray. Journal of Virology 85.8 (2011): 3780-3791.

Levene, et al. Zero-mode waveguides for single-molecule analysis at high concentrations. Science. Jan. 31, 2003;299(5607):682-6.

Macosko, et al. Highly paralled genome-wide expression profiling of individuals cells using nanoliter droplets. Cell 161.5 (2015): 1202-1214.

Mannocci, "DNA-Encoded Chemical Libraries", A dissertation submitted to the ETH Zurich for the degree of Doctor of Sciences, 2009, 171 pages.

Margulies, et al. Genome sequencing in microfabricated high-density picolitre reactors. Nature. Sep. 15, 2005;437(7057):376-80. Epub Jul. 31, 2005.

Maynard, et al. Antibody engineering. Annu Rev Biomed Eng. 2000;2:339-76.

Nam, et al. Nanoparticle-based bio-bar-codes for the ultrasensitive detection of p. Science, American Association for the Advancement of Science, US, vol. 301, Sep. 26, 2003, pp. 1884-1886.

Needels et al., "Generation and screening of an oligonucleotide-encoded synthetic peptide library", Proc. Natl. Acad. Sci. USA, 1993, 90: 10700-10704.

Nielsen et al., "Synthetic Methods for the Implementation of Encoded Combinatorial Chemistry", J. Am. Chem. Soc., 1993, 115: 9812-9813.

Nolan. Tadpoles by the tail. Nat Methods. Jan. 2005;2(1):11-2.

Nwe, et al. Growing applications of "click chemistry" for bioconjugation in contemporary biomedical research. Cancer Biotherapy and Radiopharmaceuticals 24.3 (2009): 289-302.

Office action dated Feb. 27, 2017 for U.S. Appl. No. 13/981,711.

Office action dated Jun. 12, 2017 for U.S. Appl. No. 14/420,345.

Office action dated Jun. 23, 2017 for U.S. Appl. No. 13/981,711.

Pai, et al., (2005) Proximity ligation assays with peptide conjugate 'burrs' for the sensitive dection of spores, Nucleic Acids Research, vol. 33, No. 18, e162, pp. 1-7.

Pathak, et al. Hydroxylated quantum dots as luminescent probes for in situ hybridization. J Am Chem Soc. 2001;123(17):4103-4.

Reece, et al. Characterization of differential gene expression profiles in diabetic embryopathy using DNA microarray analysis. American Journal of Obstetrics & Gynecology, Mosby, St. Louis, MO, US, vol. 195, No. 4, Oct. 1, 2006, pp. 1075-1080.

Remacle, et al. Architecture with designer atoms: simple theoretical considerations. Proc Natl Acad Sci U S A. Jan. 18, 2000;97(2):553-8.

(56) References Cited

OTHER PUBLICATIONS

Shagina, et al. Normalization of genomic DNA using duplex-specific nuclease. Biotechniques. Jun. 2010;48(6):455-9. doi: 10.2144/000113422.

Shin, et al. Chemistries for patterning robust DNA microbarcodes enable multiplex assays of cytoplasm proteins from single cancer cells. Chemphyschem. Oct. 4, 2010;11(14):3063-9. doi: 10.1002/cphc.201000528.

Sieber, et al. Selecting proteins with improved stability by a phage-based method. Nat Biotechnol. Oct. 1998;16(10):955-60.

Simon, et al. Peptoids: a modular approach to drug discovery. Proc Natl Acad Sci U S A. Oct. 15, 1992;89(20):9367-71.

Smith, et al. Highly-multiplexed barcode sequencing: an efficient method for parallel analysis of pooled samples. Nucleic Acids Res. Jul. 2010;38(13):e142. doi: 10.1093/nar/gkq368. Epub May 11, 2010.

Soares, et al. Expressed sequence tags: normalization and subtraction of cDNA libraries. Methods Mol Biol. 2009;533:109-22. doi: 10.1007/978-1-60327-136-3_6.

Soni, et al. Progress toward ultrafast DNA sequencing using solid-state nanopores. Clin Chem. Nov. 2007;53(11):1996-2001. Epub Sep. 21, 2007.

Spada, et al. Selectively infective phages (SIP). Biol Chem. Jun. 1997;378(6):445-56.

Spray, David C., Illuminating gap junctions, Nature Methods, Jan. 2005, pp. 12-14, vol. 2, No. 1.

Stoeckius, et al. Simultaneous epitope and transcriptome measurement in signle cells. Nature methods. Jul. 31, 2017.

Supplemental Search Report for EP13827091, dated Apr. 26, 2016, (2 pages).

Tabb, et al. Statistical characterization of ion trap tandem mass spectra from doubly charged tryptic peptides. Anal Chem. Mar. 1, 2003;75(5):1155-63.

Tabuchi et al., "Multi-line split DNA synthesis: a novel combinatorial method to make high quality peptide libraries", BMC Biotechnology, 2004, 4:19, 8 pages.

Tanner, et al. Multiplex bio-assay with inductively coupled plasma mass spectrometry: Towards a massively multivariate single-cell technology. Spectrochimia Acta Part B. 2007; 62(3):188-95.

Tanaka et al, Structure and Mechanisms of a Protein-Based Organelle in *Escherichia coli,* Science, Jan. 1, 2010, p. 81, vol. 327.

Turro, N.J. Modern Molecular Photochemistry, Menlo Park: Benjamin/Cummings Publishing Col, Inc. (1978), pp. 296-361.

Venter, et al. The sequence of the human genome. Science. Feb. 16, 2001;291(5507):1304-51.

Wilson, et al. In vitro selection of functional nucleic acids. Annu Rev Biochem. 1999;68:611-47.

Wlotzka, et al. In vivo properties of an anti-GnRH Spiegelmer: an example of an oligonucleotide-based therapeutic substance class. Proc Natl Acad Sci U S A. Jun. 25, 2002;99(13):8898-902. Epub Jun. 17, 2002.

Yang, et al. Construction and selection of bead-bound combinatorial oligonucleoside phosphorothioate and phosphorodithioate aptamer libraries designed for rapid PCR-based sequencing. Nucleic Acids Res Dec. 1, 2002, vol. 30, No. 23, pp. e1321-e13218.

Yuan et al, An automated microwell platform for large-scale single cell RNA Seq, Scientific reports 6 (2016): 33883.

* cited by examiner

Patchwork COB

METHODS OF IDENTIFYING MULTIPLE EPITOPES IN CELLS

CROSS-REFERENCE

This application is a continuation of U.S. application Ser. No. 17/951,008, filed on Sep. 22, 2022, which is a continuation of U.S. application Ser. No. 17/870,697, filed on Jul. 21, 2022, which is a continuation of U.S. application Ser. No. 16/795,203, filed on Feb. 19, 2020, which is a continuation of U.S. application Ser. No. 16/147,250, filed on Sep. 28, 2018, now issued as U.S. Pat. No. 10,982,256, which is a continuation of U.S. application Ser. No. 13/981,711, filed on Apr. 15, 2016, now issued as U.S. Pat. No. 10,144,950, which is a § 371 national phase of International Application No. PCT/US2012/023411, filed on Jan. 31, 2012, which claims priority to U.S. Application Ser. No. 61/437,854 filed on Jan. 31, 2011 and 61/444,067 filed on Feb. 17, 2011, all of which applications are incorporated herein by reference in their entireties.

BACKGROUND OF THE INVENTION

Although all cells in the human body contain the same genetic material, the same genes are not active in all of those cells. Alterations in gene expression patterns can have profound effects on biological functions. Furthermore, understanding the dynamics and the regulation of gene products (proteins), their variants, and interacting partners is essential in understanding, for example, the mechanisms behind genetic/and environmentally induced disorders or the influences of drug mediated therapies. This understanding can potentially become the underlying foundation for further clinical and diagnostic analyses. Therefore, identifying and quantifying the expression and regulation of genes and/or their products in cells can aid the discovery of new therapeutic and diagnostic targets.

Critical to these studies is the ability to qualitatively determine gene expression and specific variants of whole proteins (e.g., splice variants, point mutations, post-translationally modified versions, and environmentally/therapeutically-induced modifications) and the ability to view their quantitative modulation. Moreover, it is becoming increasing important to perform these analyses from not just one, but multiple target molecules in a cell. The methods available to date still require significant amounts of biological samples or will not provide cell specific information. Additionally, there are limited methods of multiplexed protein measurement technologies due to the additional challenges inherent in protein samples.

Thus, there exists a need for accurate and sensitive detection, identification and quantification of target molecules in every cell of a complex cell population and to retain cell specific information regarding that target molecule.

SUMMARY OF THE INVENTION

The invention relates generally to the field of detection, identification, and quantification of target molecules in a sample. The present invention relates in part to the detection, identification, and quantification of individual target molecules in single cells of a complex cell population while retaining cell specific information regarding that target molecule.

In some embodiments, the invention relates to methods for identifying whether a plurality of targets are in a plurality of cells comprising: binding to the targets a plurality of tags, wherein a tag comprises a code that represents a) the target identity and b) the identity of the cell in which tag is binding. In some embodiments, individual cell separation or isolation is unnecessary for the binding step. In some embodiments, tags comprise building blocks that are directly or indirectly associated with each other, for example through covalent binding or by association through affinity. In some embodiments, tags are formed through polymerization of building blocks in place. In some embodiments, multiple building blocks are added in a step. In some embodiment, a single building block is added at each step. In some embodiments, the cell is alive. In some embodiments, the cell is lysed or fixed.

In some embodiments, the invention relates to methods for identifying a single cell associated with a target comprising: binding to the target a tag, wherein the tag comprises a code that represents a) the target, and b) the single cell; wherein the during the binding the single cell is not isolated from a population of cells, and wherein the code that represents the single cell is unknown before the binding.

In some embodiments, the invention relates to methods for identifying a single cell associated with a target comprising: binding to the target a tag, wherein the tag comprises a code that represents a) the target, and b) the single cell; wherein the during the binding the single cell is isolated from a population of cells, and wherein the code that represents the single cell is unknown before the binding.

In some embodiments, the invention further comprises detecting the code, wherein individual cell separation or isolation is unnecessary for the detecting step. In some embodiments, each target is a protein or a nucleic acid. In some embodiments, the tag is a nucleic acid or a polypeptide. In some embodiments, the tag is comprises a series monomeric subunits that comprise a decipherable code. In some embodiments, the tag is a coded molecular constituent that can be decoded. In some embodiments, the tag comprises a combination of parts that can be decoded to determine the nature of the tag.

In some embodiments, the tag comprises a UBA. In some embodiments, the UBA is specific for one of the targets. In some embodiments, the tag comprises a UBA. In some embodiments, the UBA comprises an antibody. In some embodiments, the tag comprises a ESB. In some embodiments, the ESB comprises a common linker (CL). In some embodiments, the ESB codes the target identity. In some embodiments, the ESB comprises a nucleic acid. In some embodiments, the tag comprises an APS. In some embodiments, the APS is detectable a detectably distinct coding unit. In some embodiments, during the binding step multiple APSs are added to the tag in an ordered manner during successive rounds of split pool synthesis. In some embodiments, the tag comprises at least 10 APSs. In some embodiments, the APS comprises a nucleic acid. In some embodiments, the tag comprises multiple APSs, an ESB, and a UBA linked by ligation. In some embodiments, multiple APSs, the ESB, and/or the UBA is capable of being linked Click chemistry. In some embodiments, the APS or the ESB comprises an amplification primer binding region. In some embodiments, the UBA, ESB, or APS is templatable. In some embodiment, the UBA, ESB, or APS is of a different discernable constituent (GPN: meaning one part of the code can be a nucleic acid, another can be a polypeptide, another can be a small molecule, etc.).

In some embodiments, the invention relates to compositions comprising: a) a first target molecule, b) a first unique binding agent (UBA) specific for the first target molecule, c)

a first linkable UBA-dependent epitope specific barcode (ESB), and d) a plurality of ordered assayable polymer subunit (APS), wherein the order of APSs is detectable. In some embodiments, the target molecule is selected from the group consisting of a peptide, a polypeptide, an oligopeptide, a protein, a phosphoprotein, an antibody, a nucleic acid, a peptide nucleic acid, a synthetic small molecule, a disaccharide, a trisaccharide, an oligosaccharide, a polysaccharide, a lipid, a steroid, and a phospholipid.

In some embodiments, the invention relates to compositions comprising a population of particles each comprising at least a first target molecule, wherein the first target molecule is associated with: a) a first unique binding agent (UBA) specific for the first target molecule, b) a first linkable UBA-dependent epitope specific barcode (ESB), and c) a first plurality of ordered assayable polymer subunits (APS), wherein the plurality of ordered APSs associated with the first target molecule of a first particle in the population is detectably different than the plurality of ordered APSs associated with the first target molecule of a second particle in the population.

In some embodiments, the plurality of ordered APSs comprises 2, 3, 4, 5, 6, 7, 8, 9, 10, 11, 12, 13, 14, 15, 16, 17, 18, 19, or 20 APSs. In some embodiments, the plurality of ordered APSs comprises more than 20 APSs. In some embodiments, the APSs are templatable. In some embodiments, at least one discrete particle is selected from the group consisting of a cell, a liposome, an organelle, a micelle, a droplet and a bead. In some embodiments, the target molecule is selected from the group consisting of a peptide, a polypeptide, an oligopeptide, a protein, a phosphoprotein, an antibody, a nucleic acid, a peptide nucleic acid, a synthetic small molecule, a disaccharide, a trisaccharide, an oligosaccharide, a polysaccharide, a lipid, a steroid, and a phospholipid. In some embodiments, the first ESB comprises a first common linker (CL). In some embodiments, said first target molecule is directly bound to said first UBA and said first ESB is directly bound to said first UBA. In some embodiments, the plurality of ordered APS is formed by stepwise addition of APSs in separate rounds. In some embodiments, the APS added on each round is linked to the first complex. In some embodiments, the linking is in order of rounds. In some embodiments, the linking is performed through binding affinity. In some embodiments, the linking of an APS, an ESB, or a UBA is performed using chemical methods. In some embodiments, the chemical method comprises Click chemistry. In some embodiments, the linking is performed in the presence of $Cu^I$. In some embodiments, a UBA, an APS, or an ESB comprises nucleic acids. Some embodiments further comprise a first linking oligonucleotide comprising a first and a second complementary region to two components selected from a UBA, an APS, and an ESB. In some embodiments, a UBA, an APS, or an ESB is linked using a linking oligonucleotide comprising the first and the second complementary region to two components selected from a UBA, an APS, and an ESB. Some embodiments further comprise a second linking oligonucleotide comprising a third and a fourth complementary region to two components selected from a UBA, an APS, and an ESB. In some embodiments, a UBA, an APS, or an ESB is linked using a linking oligonucleotide comprising the third and the fourth complementary region to two components selected from a UBA, an APS, and an ESB. In some embodiments, the second and fourth complementary regions are identical. In some embodiments, the second and fourth complementary regions are identical. In some embodiments, the first or second complementary region is shared between two APSs within the plurality of APSs. In some embodiments, the linking is performed by ligation. In some embodiments, the linking oligonucleotide comprises a subcode encoding the origin of the APS or the ESB. In some embodiments, the APS has a subcode encoding the origin of the APS. In some embodiments, the ESB has a subcode encoding the origin of the ESB. In some embodiments, an individual APS, ESB, or linking oligonucleotide molecule comprises a unique counter tag. In some embodiments, unique counter tag is detectable. In some embodiments, the ESB is covalently linked to the linking oligonucleotide. In some embodiments, an APS or an ESB comprises an amplification primer binding region. In some embodiments, the APSs and ESB, when linked, are capable of encoding a secondary product. In some embodiments, the secondary product is an RNA or a peptide. In some embodiments, the APSs and ESB, when linked, comprises a polymerase start site. In some embodiments, the peptide comprises an affinity tag. In some embodiments, the affinity tag is a His-tag. In some embodiments, the UBA, ESB, or APS is templatable. In some embodiments, the composition further comprises a probe. In some embodiments, the probe is attached to a surface. In some embodiments, the surface comprises an array. In some embodiments, the surface comprises a bead. In some embodiments, the UBA is selected from the group consisting of antibody, peptide, aptamer, peptoid and nucleic acid. In some embodiments, the ESB is selected from the group consisting of nucleic acids, beads and chemical subunits. In some embodiments, said APS comprises a nucleic acid, a small molecule, or buildable complex molecules of deterministic weight.

In some embodiments, the invention relates to kits for labeling a target molecule of a cell in a population of cells with a cell origination barcode, comprising a) n sets of m assayable polymer subunits (APSs) each comprising a distinct package of information; wherein the packages of information are capable of being linked in an ordered fashion; b) a target molecule-specific unique binding agent (UBA).

In some embodiments, the invention relates to kits for labeling a target molecule of a cell in a population of cells with a cell origination barcode, comprising a) n sets of m assayable polymer subunits (APSs) each comprising a distinct package of information; wherein the packages of information are capable of being linked in an ordered fashion; b) a plurality of target molecule-specific unique binding agents (UBA) each linked with a UBA-specific epitope specific barcode (ESB).

In some embodiments, the invention relates to kits for labeling a target molecule of a cell in a population of cells with a cell origination barcode, comprising a) n sets of m assayable polymer subunits (APSs) each comprising a distinct package of information; wherein the packages of information are capable of being linked in an ordered fashion; b) a plurality of target molecule-specific unique binding agents (UBA); c) a plurality of UBA-specific epitope specific barcode (ESB), wherein each ESB is capable of linking with a designated UBA.

In some embodiments, n is 1, 2, 3, 4, 5, 6, 7, 8, 9, or 10. In some embodiments, m is 2, 3, 4, 5, 6, 7, 8, 9, 10, 11, 12, 13, 14, 15, 16, 17, 18, 19, or 20. In some embodiments, n is greater than 10. In some embodiments, m is greater than 20. In some embodiments, the first ESB comprises a first common linker (CL). In some embodiments, said ESB is capable of directly binding to said UBA. In some embodiments, said UBA is capable of directly binding to the target molecule. In some embodiments, at least two of the assayable polymer subunit (APS) sets are identical. In some embodiments, the APSs in a first set is linkable to the APSs in a second set. In some embodiments, the APSs in a first set is further linkable to the APSs in a second set in an ordered fashion. In some embodiments, an APS, an ESB, or a UBA is capable of being linked using chemical methods. In some embodiments, the chemical method comprises Click chemistry. In some embodiments, the presence of $Cu^I$ is required for linkage. In some embodiments, the kit components can assemble through affinity binding. In some embodiments, a UBA, an APS, or an ESB comprises nucleic acids. In some embodiments, the kits further comprise a first linking oligonucleotide comprising a first and a second complementary region to two components selected from a UBA, an APS, and an ESB. In some embodiments, the kits further comprise a second linking oligonucleotide comprising a third and a fourth complementary region to two components selected from a UBA, an APS, and an ESB. In some embodiments, the first and third complementary regions are identical. In some embodiments, the second and fourth complementary regions are identical. In some embodiments, an APS, an ESB, or a UBA is capable of being linked by ligation. In some embodiments, the linking oligonucleotide comprises a subcode encoding the original set of the APS or the ESB. In some embodiments, the APS has a subcode encoding the origin population of the APS. In some embodiments, the ESB has a subcode encoding the origin population of the ESB. In some embodiments, an individual APS, ESB, or linking oligonucleotide molecule comprises a unique counter tag. In some embodiments, the unique counter tag is detectable. In some embodiments, the ESB is covalently linked to the linking oligonucleotide. In some embodiments, an APS or an ESB comprises an amplification primer binding region. In some embodiments, the APSs and ESB, when linked, are capable of encoding a secondary product. In some embodiments, the secondary product is an RNA or a peptide. In some embodiments, the APSs and ESB, when linked, comprises a polymerase start site. In some embodiments, the peptide comprises an affinity tag. In some embodiments, the affinity tag is a His-tag. In some embodiments, the UBA, ESB, or APS is templatable. In some embodiments, the kit further comprises a probe. In some embodiments, the probe is attached to a surface. In some embodiments, the surface comprises an array. In some embodiments, the surface comprises a bead. In some embodiments, the plurality of UBAs comprises 2, 3, 4, 5, 10, 20, 30, 50, 100, 200, 300, 500, 600, 700, 800, 900, 1000 or more than 1000 UBAs. In some embodiments, the plurality of UBAs comprises up to 2000 UBAs. In some embodiments, the UBA is selected from the group consisting of antibody, peptide, aptamer, peptoid and nucleic acid. In some embodiments, the ESB is selected from the group consisting of nucleic acids, beads and chemical subunits. In some embodiments, said APS comprises a nucleic acid, a small molecule, or buildable complex molecules of deterministic weight.

In some embodiments, the invention relates to methods for identifying target molecules sharing a common particle origin, comprising labeling a first plurality of targets of a first particle in a population of x particles with a first origination barcode; and labeling a second plurality of targets of a second particle in a population of x particles with a second origination barcode; wherein each origination barcode comprises a set of n assayable polymer subunits (APS); wherein each of the n APSs in the first and second set of APSs is selected from a group comprising m different APSs; and wherein the first and second origination barcodes are detectably different from each other with a certainty of $c=1-[(1-1/x)^{(m^n)}]$. In some embodiments, x is greater than 1,000,000. In some embodiments, c is greater than 99.9%. In some embodiments, c is greater than 99.99%. In some embodiments, c is greater than 99.999%. In some embodiments, c is greater than 99.9999%. In some embodiments, c is greater than 99.99999%. In some embodiments, n is 2, 3, 4, 5, 6, 7, 8, 9, or 10. In some embodiments, m is 2, 3, 4, 5, 6, 7, 8, 9, 10, 11, 12, 13, 14, 15, 16, 17, 18, 19, or 20. In some embodiments, n is greater than 10. In some embodiments, m is greater than 20.

In some embodiments, at least one discrete particle is selected from the group consisting of a cell, a liposome, an organelle, a micelle, a droplet and a bead. In some embodiments, the target molecule is selected from the group consisting of a peptide, a polypeptide, an oligopeptide, a protein, a phosphoprotein, an antibody, a nucleic acid, a peptide nucleic acid, a synthetic small molecule, a disaccharide, a trisaccharide, an oligosaccharide, a polysaccharide, a lipid, a steroid, and a phospholipid. In some embodiments, at least two groups comprising m different APSs are identical.

In some embodiments, n APSs are added in separate rounds. In some embodiments, the APSs of separate rounds are linked. In some embodiments, the linking is in order of rounds. In some embodiments, an appropriate n and/or m is selected based in a desired certainty level given a number of cells, x.

In some embodiments, the invention relates to methods of imparting a particle specific code to a component of a particle of a population of particles, the method comprising: linking a first ordered set of assayable polymer subunits (APS) to a first component of a first particle of a population of particles, wherein the order of the APSs is detectable. In some embodiments, the method further comprises detecting the first ordered set of APSs linked with the first component, thereby determining a particle origin of the first component. In some embodiments, the method further comprises linking a second ordered set of assayable polymer subunits (APS) to a second component of the first particle of a population of particles, wherein the order of the APSs is detectable. In some embodiments, the method further comprises detecting the second ordered set of APSs linked with the second component, thereby determining the particle origin of the second component. In some embodiments, the first and the second ordered sets of APSs linked with the first and second components of the first particle are the same. In some embodiments, the method further comprises linking a third ordered set of assayable polymer subunits (APS) to a first component of second particle of a population of particles, wherein the order of the APSs is detectable. In some embodiments, the first ordered set of APSs linked with the first component of the first particle is different than the third ordered set of assayable polymer subunits linked with the first component of the second particle. In some embodiments, the method further comprises linking a component specific epitope specific barcode (ESB) to the first component. In some embodiments, the method further comprises linking a component specific ESB to the second component. In some embodiments, at least the particle is selected from the group consisting of a cell, a liposome, an organelle, a micelle, a droplet and a bead. In some embodiments, said at least one target molecule is directly bound to said first UBA and said ESB is directly bound to said UBA. In some embodiments, at least two of the assayable polymer subunit (APS) sets are identical. In some embodiments, each APS from the ordered set of APSs is linked to the first complex. In some embodiments, the linking is in order of rounds. In some embodiments, the UBA. ESB, or APS encodes a secondary product. In some embodiments, the secondary product is an RNA or a peptide. In some embodiments, the UBA, ESB, or APS is templatable. In some embodiments, the ESB further comprises a unique counter tag. In some embodiments, the quantity of the target molecule of the molecule is estimated using the counter tag. In some embodiments, the APS further comprises a round-specific subcode. In some embodiments, the detection further comprises determining the presence of an APS from a designated round. In some embodiments, detection is digital. In some embodiments, detection is indirect. In some embodiments, detecting comprises mass spectrometry. In some embodiments, detecting comprises nucleic acid sequencing. In some embodiments, detecting comprises peptide sequencing. In some embodiments, detecting comprises mass gel electrophoresis. In some embodiments, detecting comprises HPLC or other chromatographic separation. In some embodiments, detecting comprises detecting one or more signals associated with one or more individual APSs. In some embodiments, the signals are ordered. In some embodiments, detecting comprises using one or more probes. In some embodiments, the probe is attached to a surface. In some embodiments, the surface comprises an array. In some embodiments, the surface comprises a bead. In some embodiments, detecting comprises a separation. In some embodiments, the separation is multi-dimensional. In some embodiments, the separation resolves the first linkable UBA-dependent epitope specific barcode (ESB) from a second linkable UBA-dependent epitope specific barcode (ESB). In some embodiments, 3, 4, 5, 10, 20, 30, 50, 100, 200, 300, 500, 600, 700, 800, 900, 1000 or more than 1000 different target molecules are detected. In some embodiments, up to 2000 different target molecules are detected. In some embodiments, the UBA is selected from the group consisting of antibody, peptide, aptamer, peptoid and nucleic acid. In some embodiments, the ESB is selected from the group consisting of nucleic acids, beads and chemical subunits. In some embodiments, said APS comprises a nucleic acid, a small molecule, or buildable complex molecules of deterministic weight. In some embodiments, the APSs are linked to through ligation or extension via polymerization. In some embodiments, a cell origination barcode (COB) is generated with the APSs from the ordered set of APSs. In some embodiments, each COB in said plurality of complexes has a detectable signal or sequence that distinguishes it from other COBs in said population of cells. In some embodiments, an APS, an ESB, or a UBA is linked using chemical methods. In some embodiments, the chemical method comprises Click chemistry. In some embodiments, the linking is performed in the presence of $Cu^I$. In some embodiments, a UBA, an APS, or an ESB comprises nucleic acids. In some embodiments, the linking of a UBA, an APS, or an ESB is performed using a linking oligonucleotide that comprises a first and a second complementary region to two components to be linked. In some embodiments, the first or second complementary region is shared between APSs within a population of APSs. In some embodiments, the first or second complementary region is distinct for two different round-specific sets of APSs. In some embodiments, the method further comprises ligation. In some embodiments, the target molecule is selected from the group consisting of a peptide, a polypeptide, an oligopeptide, a protein, a phosphoprotein, an antibody, a nucleic acid, a peptide nucleic acid, a synthetic small molecule, a disaccharide, a trisaccharide, an oligosaccharide, a polysaccharide, a lipid, a steroid, and a phospholipid. In some embodiments, the first ESB comprises a first common linker (CL). In some embodiments, the first ESB comprises a first common linker (CL). In some embodiments, an individual APS, ESB, or linking oligonucleotide molecule comprises a unique counter tag. In some embodiments, detection comprises detecting the unique counter tag. In some embodiments, the number of unique counter tags associated with a specific ESB is determined. In some embodiments, the number of detected unique counter tags relate to the initial quantity of the specific ESB. In some embodiments, the ESB is covalently linked to the linking oligonucleotide. In some embodiments, an APS or an ESB comprises an amplification primer binding region. In some embodiments, a COB encodes a peptide sequence. In some embodiments, the COB comprises a polymerase start site. In some embodiments, the peptide comprises an affinity tag. In some embodiments, the affinity tag is a His-tag.

In some embodiments, the invention relates to methods for detecting plurality of properties originating from a plurality of discrete particles, the method comprising: a) providing: i) a population of particles comprising at least a first target molecule; ii) a first unique binding agent (UBA) specific for the first target molecule; iii) a first linkable UBA-dependent epitope specific barcode (ESB); iv) a plurality of round-specific assayable polymer subunit (APS) sets, each set containing a plurality of APSs that are detectably distinct from each other; b) forming at least a first complex comprising said at least first target molecule, said first UBA probe, and said first ESB; c) performing n rounds of split pool synthesis, each round comprising: i) splitting the population of particles into m reaction volumes; ii) contacting one or more reaction volumes with an APS from the APS set specific for the round; iii) pooling two or more reaction volumes; d) detecting a plurality of properties from at least one particle from the population of particles; wherein at least one of the properties relate to a quantity or an identity for a target molecule associated with the particle.

In some embodiments, the invention relates to methods for detecting a plurality of properties originating from a plurality of discrete particles, the method comprising: a) providing: i) a population of particles comprising at least a first target molecule; ii) a first unique binding agent (UBA) specific for the first target molecule; iii) a first linkable UBA-dependent epitope specific barcode (ESB); and iv) a plurality of round-specific assayable polymer subunit (APS) sets, each set containing a plurality of APSs that are detectably distinct from each other; b) forming at least a first complex comprising said at least first target molecule, said first UBA probe, and said first ESB; c) performing n rounds of split pool synthesis, each round comprising: i) splitting the population of particles into m reaction volumes; ii) contacting one or more reaction volumes with an APS from the APS set specific for the round; and iii) pooling two or more reaction volumes; d) performing another round of split pool synthesis comprising steps c) i) and c) ii); e) detecting a plurality of properties from at least one particle from the population of particles; wherein at least one of the properties relate to a quantity or an identity for a target molecule associated with the particle.

In some embodiments, the split pool method is replaced by separation of particles, for example in microwells, or in microfluidic devices. In some embodiments, separated cells are labeled with cell origination barcodes. In some embodiments, cell origination barcodes are built in place by stepwise addition of building blocks.

In some embodiments, n is 1, 2, 3, 4, 5, 6, 7, 8, 9, 10, 11, 12, 13, 14, 15, 16, 17, 18, 19, or 20. In some embodiments, n is more than 20. In some embodiments, m is different between at least two rounds. In some embodiments, m is 2, 3, 4, 5, 6, 7, 8, 9, 10, 11, 12, 13, 14, 15, 16, 17, 18, 19, or 20. In some embodiments, m is more than 20. In some embodiments, at least one discrete particle is selected from the group consisting of a cell, a liposome, an organelle, a micelle, a droplet and a bead. In some embodiments, the target molecule is selected from the group consisting of a peptide, a polypeptide, an oligopeptide, a protein, a phosphoprotein, an antibody, a nucleic acid, a peptide nucleic acid, a synthetic small molecule, a disaccharide, a trisaccharide, an oligosaccharide, a polysaccharide, a lipid, a steroid, and a phospholipid. In some embodiments, the first ESB comprises a first common linker (CL). In some embodiments, said at least one target molecule is directly bound to said first UBA and said ESB is directly bound to said UBA. In some embodiments, at least two of the assayable polymer subunit (APS) sets are identical. In some embodiments, the APS added on each round is linked to the first complex. In some embodiments, the linking is in order of rounds. In some embodiments, the UBA, ESB, or APS encodes a secondary product. In some embodiments, the secondary product is an RNA or a peptide. In some embodiments, the UBA, ESB, or APS is templatable. In some embodiments, the ESB further comprises a unique counter tag. In some embodiments, the quantity of the target molecule of the molecule is estimated using the counter tag. In some embodiments, the APS further comprises a round-specific subcode. In some embodiments, the detection further comprises determining the presence of an APS from a designated round. In some embodiments, detection is digital. In some embodiments, detection is indirect. In some embodiments, detecting comprises mass spectrometry. In some embodiments, detecting comprises nucleic acid sequencing. In some embodiments, detecting comprises peptide sequencing. In some embodiments, detecting comprises detecting one or more signals associated with one or more individual APSs. In some embodiments, the signals are ordered. In some embodiments, detecting comprises using one or more probes. In some embodiments, the probe is attached to a surface. In some embodiments, the surface comprises an array. In some embodiments, the surface comprises a bead. In some embodiments, detecting comprises a separation. In some embodiments, the separation is multi-dimensional. In some embodiments, the separation resolves the first linkable UBA-dependent epitope specific barcode (ESB) from a second linkable UBA-dependent epitope specific barcode (ESB). In some embodiments, 3, 4, 5, 10, 20, 30, 50, 100, 200, 300, 500, 600, 700, 800, 900, 1000 or more than 1000 different target molecules are detected. In some embodiments, up to 2000 different target molecules are detected. In some embodiments, the UBA is selected from the group consisting of antibody, peptide, aptamer, peptoid and nucleic acid. In some embodiments, the ESB is selected from the group consisting of nucleic acids, beads and chemical subunits. In some embodiments, said APS comprises a nucleic acid, a small molecule, or buildable complex molecules of deterministic weight. In some embodiments, the APSs are linked to through ligation or extension via polymerization. In some embodiments, a cell origination barcode (COB) is generated from APSs of round specific APS sets. In some embodiments, each COB in said plurality of complexes has a detectable signal or sequence that distinguishes it from other COBs in said population of cells. In some embodiments, an APS, an ESB, or a UBA is linked using chemical methods. In some embodiments, the chemical method comprises Click chemistry. In some embodiments, the linking is performed in the presence of $Cu^I$. In some embodiments, a UBA, an APS, or an ESB comprises nucleic acids. In some embodiments, the linking of a UBA, an APS, or an ESB is performed using a linking oligonucleotide that comprises a first and a second complementary region to two components to be linked. In some embodiments, the first or second complementary region is shared between APSs within a population of APSs. In some embodiments, the first or second complementary region is distinct for two different round-specific sets of APSs. Some embodiments further comprise ligation. In some embodiments, the linking oligonucleotide comprises a subcode encoding the origin population of the APS or the ESB. In some embodiments, the APS has a subcode encoding the round-specific set of the APS. In some embodiments, the ESB has a subcode encoding the origin presence of the ESB. In some embodiments, an individual APS, ESB, or linking oligonucleotide molecule comprises a unique counter tag. In some embodiments, detection comprises detecting the unique counter tag. In some embodiments, the number of unique counter tags associated with a specific ESB is determined. In some embodiments, the number of detected unique counter tags relate to the initial quantity of the specific ESB. In some embodiments, the ESB is covalently linked to the linking oligonucleotide. In some embodiments, an APS or an ESB comprises an amplification primer binding region. In some embodiments, a COB encodes a peptide sequence. In some embodiments, the COB comprises a polymerase start site. In some embodiments, the peptide comprises an affinity tag. In some embodiments, the affinity tag is a His-tag. In some embodiments, each of the reaction volumes created by the most recent splitting receives a different APS from the APS set.

In some embodiments, the invention provides methods for detecting at least one target molecule in a sample comprising the steps: (a) providing: (i) a population of cells potentially comprising at least one target molecule, (ii) a first UBA specific for a first target molecule, (iii) a first epitope specific barcode ESB specific for a region of the first UBA, where the ESB comprises a first common linker moiety, and (iv) a population of COB, where the population of COB comprises a second common linker moiety, where the second linker moiety is complementary to the first common linker moiety is the first ESB; (b) forming at least a first complex comprising the at least one target molecule, the first LBA probe, and the first ESB, where the at least one target molecule is bound to the first UBA and the ESB is bound to the UBA (c) adding the population of COBs, where a second complex is formed with the least one target molecule, the first UBA probe, the first ESB, and a first COB, and where the second common linker moiety from the first COB is bound to the first linker moiety from the first ESB, and where the COBs from the population of COBs is associated with a cell from the population of cells; and (d) detecting the second complex or at least part of the third complex.

In some embodiments the invention provides methods for detecting at least one target molecule in a sample comprising the steps: (a) providing: (i) a population of cells potentially comprising at least one target molecule, (ii) a first unique binding agent (UBA) specific for a first target molecule, (iii) a first epitope specific barcode (ESB) specific for a region of the first UBA, where the ESB comprises a first common linker moiety, and (iv) a population of assayable polymer subunits (APSs), where the APSs comprises a second common linker moiety and a third common linker moiety, where the second linker moiety is complementary to the first common linker moiety is the first ESB; (b) forming at least a first complex comprising the at least one target molecule, the first UBA probe, and the first ESB, where the at least one target molecule is bound to the first UBA and the ESB is bound to the UBA; (c) splitting the population into two or more samples; (d) adding one APS from the population of APSs per sample to the two or more samples from step (c), where a second complex is formed with the least one target molecule, the first UBA probe, the first ESB, and a first APS, and where the second common linker moiety from the first APS is bound to the first linker moiety from the first ESB; (e) pooling the two or more samples from step (c) into one sample; (f) splitting the sample from step (e) into two or more samples; (g) adding one APS from the population of APSs per sample to the two or more samples from step (e), where a third complex is formed with the least one target molecule, the first UBA probe, the first ESB, the first APS, and the second APS, where the second common linker moiety from the second APS is bound to the third linker moiety from the first APS, and where the first APS and the second APS form a cell origination barcode (COB); and (c) detecting the third complex or at least part of the third complex. In some embodiments, the methods further comprise repeating steps (e), through (g).

In some embodiments, the methods further comprise detecting of a plurality of target molecules by forming a plurality of complexes in step (b), each complex comprising (i) at least one target molecule (ii) a first UBA and (iii) a first epitope specific barcode (ESB) specific for a region of the first UBA, where the ESB comprises a first common linker moiety, where the at least one target molecule is bound to the first UBA and the ESB is bound to the UBA.

In some embodiments, each COB in the plurality of complexes has a detectable signal that distinguishes it from other COB in the population of cells.

In some embodiments, the complex is detected by sequencing or mass spectrometry. In some embodiments, the third complex is detected by a method comprising individually counting the presence of one or more molecules of the third complex where the presence of the one or more molecules of the third complex is indicative of the concentration of the target molecule in a cell. In some embodiments, the individually detecting further comprises detecting a digital signal.

In some embodiments, 3, 4, 5, 10, 20, 30, 50, 100, 200, 300, 500, 600, 700, 800, 900, 1000 or more than 1000 different target molecules are detected. In some embodiments, up to 2000 different target molecules are detected.

In some embodiments, the UBA is selected from the group consisting of antibody, peptide, aptamer, peptoid and nucleic acid. In some embodiments, the ESB is selected from the group consisting of nucleic acids, beads and chemical subunits.

In some embodiments, the APS is a nucleic acid, a small molecule, or buildable complex molecules of deterministic weight. In some embodiments, the APS comprises a single-stranded nucleic acid hybridized to a complementary polynucleotide sequence having attached thereto a detectable label.

In some embodiments, the first APS is attached to the first ESB through ligation or extension via polymerization. In some embodiments, the second APS is attached to the first APS through ligation or extension via polymerization.

In some embodiments, the common linker moiety is a nucleic acid. In some embodiments, the ESB is attached to the USB.

In some embodiments, said first COB comprises a plurality of APS.

Some embodiments, further comprise detecting of a plurality of target molecules by a method comprising: forming a plurality of complexes in step (b), each complex comprising (i) at least one target molecule (ii) a first UBA and (iii) a first epitope specific barcode (ESB) specific for a region of said first UBA, wherein said ESB comprises a first common linker moiety, wherein said at least one target molecule is associated with said first UBA and said ESB is associated with said UBA.

In some embodiments, each COB in said plurality of complexes has a detectable signal or sequence that distinguishes it from other COBs in said population of cells.

In some embodiments, the linking of an APS, an ESB, or a UBA is performed using chemical methods. In some embodiments, the chemical method comprises Click chemistry. In some embodiments, the linking is performed in the presence of $Cu^I$. In some embodiments, linking of an ABS, an ESB, or a UBA is performed using binding affinity. In some embodiments, a UBA, an APS, or an ESB comprises nucleic acids. In some embodiments, the linking of a UBA, an APS, or an ESB is performed using a linking oligonucleotide that comprises a first and a second complementary region to two components to be linked. In some embodiments, the first or second complementary region is shared between APSs within a population of APSs. In some embodiments, the first or second complementary region is distinct for different populations of APSs. Some embodiments further comprise ligation. In some embodiments, the linking oligonucleotide comprises a subcode encoding the origin population of the APS or the ESB. In some embodiments, the APS has a subcode encoding the origin population of the APS. In some embodiments, the ESB has a subcode encoding the origin population of the ESB. In some embodiments, an individual APS, ESB, or linking oligonucleotide molecule comprises a unique tag. In some embodiments, detection comprises detecting the unique tag. In some embodiments, the number of unique tags associated with a specific ESB is determined. In some embodiments, the number of detected unique tags relate to the initial quantity of the specific ESB. In some embodiments, the ESB is covalently linked to the linking oligonucleotide. In some embodiments, an APS or an ESB comprises an amplification primer binding region. In some embodiments, a COB encodes a peptide sequence. In some embodiments, the COB comprises a polymerase start site. In some embodiments, the peptide comprises an affinity tag. In some embodiments, the affinity tag is a His-tag. In some embodiments, the two or more samples comprise at least 5 samples. In some embodiments, the two or more samples comprise at least 10 samples. In some embodiments, the two or more samples comprise at least 20 samples. In some embodiments, each of the samples created by the most recent splitting receives a different APS.

In some embodiments, the invention relates to methods for labeling an ESB linked target molecule of a cell in a population of cells with a cell origination barcode (COB), comprising: separating each cell into an individual reaction volume; and adding the COB to the ESB via chemical or affinity means. In some embodiments, the reaction volume is selected from the group consisting of a microbubble, a microdroplet, a well, a microwell, and an enclosure in a microfluidics device.

In some embodiments, the invention relates to methods comprising disassociating a variety of types of components originating from a cell and placing the components on a particle, wherein the components are labeled on said particle. In some embodiments, the labeling comprises labeling according to cell origin. In some embodiments, the labeling comprises labeling according to component type.

In some embodiments, the signals in detection steps are ordered. In some embodiments, detecting comprises using one or more probes. In some embodiments, the probe is attached to a surface. In some embodiments, the surface comprises an array. In some embodiments, the surface comprises a bead. In some embodiments, detecting comprises a separation. In some embodiments, the separation is multi-dimensional.

In some embodiments, the invention provides methods for preparing at least one UBA, ESB and/or APS as described herein.

In some embodiments, the invention provides a population of UBAs, ESBs and/or APSs as described herein. In some embodiments, the invention provides kits comprising a population of UBAs, ESBs and APSs as described herein and instructions for its use.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
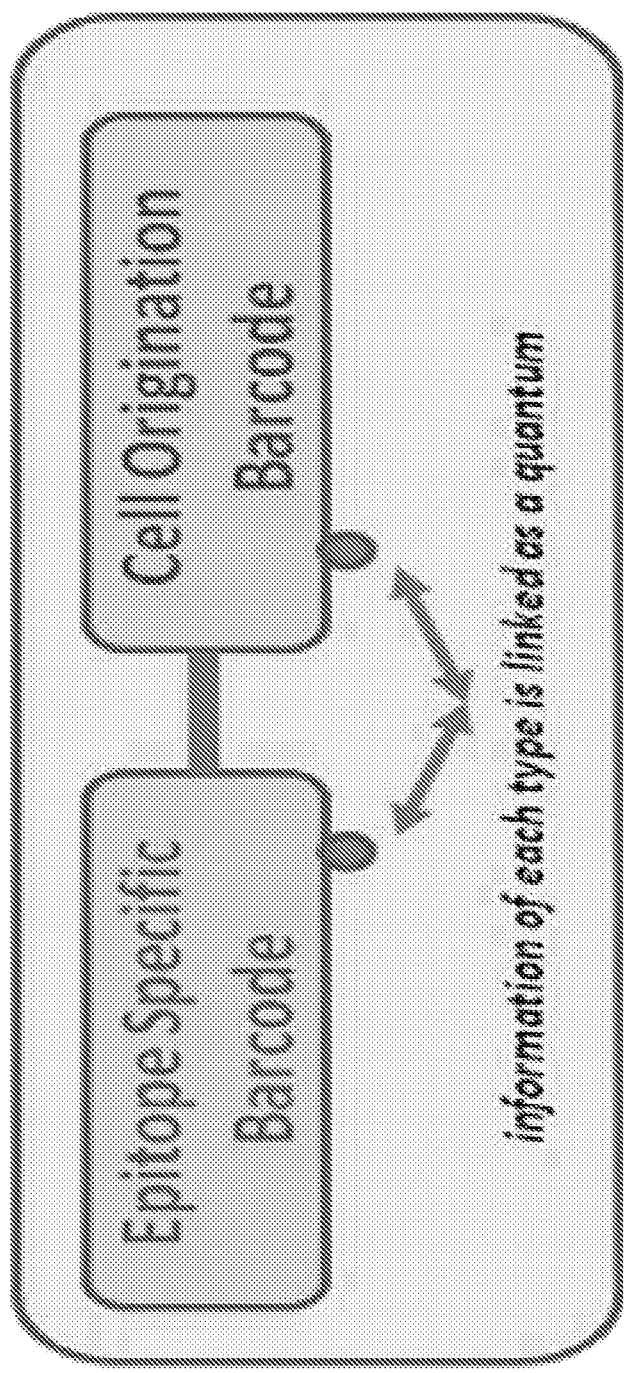
FIG. 1 depicts quantum of information representing a distinct signature (barcode) of the cell origin for each epitope.

The term "nucleic acid" refers to a nucleotide polymer, and unless otherwise limited, includes known analogs of natural nucleotides that can function in a similar manner (e.g., hybridize) to naturally occurring nucleotides.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (snRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component. Polynucleotide sequences, when provided, are listed in the 5' to 3' direction, unless stated otherwise.

The term nucleic acid encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing normucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S.

Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

A nucleic acid "probe" is an oligonucleotide capable of binding to a target nucleic acid of complementary sequence through one or more types of chemical bonds, generally through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-20 nucleotides in length).

A primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%, 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

Available binding interactions present in a mixture relying on affinity define specificity for two or more components' binding specificity. Generally, a high binding affinity for a first interaction in comparison to binding affinities of other available interactions that are available for one or more binding partners in the first interaction will lead to high specificity. Binding partners with high specificity form designated binding partners.

Reference will now be made in detail to particularly preferred embodiments of the invention. Examples of the preferred embodiments are illustrated in the following Examples section.

Unless defined otherwise, all technical and scientific terms used herein have the same meaning as is commonly understood by one of skill in the art to which this invention belongs. All patents and publications referred to herein are incorporated by reference in their entirety.

In some embodiments, the invention provides methods, compositions and kits for detection and quantification of individual target molecules in biomolecular samples. In some embodiments, the invention provides methods, compositions and kits for detection and quantification of individual target molecules in every cell of a complex cell population while retaining cell specific information regarding that target molecule. Thus in some embodiments, the invention provides methods, compositions and kits for detection and quantification of individual target molecules in a single cell basis in samples with complex cell populations. Thus in some embodiments, for each cell the amount of each target molecule associated with that cell is assayed. In particular the invention provides unique binding agents that are capable of binding individual target molecules. The invention also provides the use of epitope specific barcode to tag target molecules. The invention also provides the use of cell origination barcodes to indicate the cell of origin. Through epitope specific barcodes and cell origination barcodes, the binding of unique binding agents to target molecules results in the identification of the target molecules. Methods of making and using such unique binding agents and/or epitope specific barcodes and/or cell origination barcodes are also provided. The methods and compositions described herein can be used in a wide variety of applications such as diagnostic, prognostic, quality control and screening applications. Some embodiments of the invention relate to methods, compositions and kits for individually tagging cells.

The term "epitope" and "target molecule" are used interchangeably herein to refer to the molecule of interest (parts of it or the whole molecule) being detected and/or quantified by the methods described herein.

Certain aspects of the invention relate to the detection of multiple target molecules. The methods described herein provide potential benefits in the areas of detection of multiple target molecules, quantification, and sensitivity. In some embodiments, the invention provides methods and compositions for the study of multiple protein measurements and/or multiple nucleic acid measurements that are sensitive and reliable.

Multiplexing within one sample at a single cell level is a key advantage of this approach. Multiplexing within one sample saves significant labor, reduces sample quantity requirements proportional to the number of measurements, and improves accuracy by elimination of errors compounded by separate sample handling and measurement steps. Furthermore, obtaining measurement of multiple target molecules in single cells in a complex cell population provides a better understanding of the physiological processes within each individual cell. In some embodiments, the methods described herein allow for the pooling of different samples together during processing to be analyzed at once. This offers throughput advantages and can accelerate the analysis of different samples.

In some embodiments, the invention provides unique binding agents (UBA) for the analysis of target molecules. In some embodiments, the invention provides an UBA population for use in a multiplexed assay. Each UBA in the population is specific for a target molecule. Thus, the UBA provides the specificity for the target molecule recognized in a cell. The binding of the target molecules to the UBAs is then detected using epitope specific barcodes (ESB) and cell origination barcodes (COB). Each ESB comprises a unique code that can be associated to a specific target molecule. Each COB comprises a unique code that can be associated to a specific cell of origin.

In some embodiments, the ESB are attached, directly or indirectly, to the UBA. In other embodiments, the ESBs bind to the UBAs in a cell or sample, e.g., as part of the assay procedure. A unique COB is associated to the UBAs in a specific cell such that each COB can be associated to the target molecules bound to the UBAs in that cell. In some embodiments, the specific ESB/COB combination is referred as a quantum of information representing each target molecule or epitope (See FIG. 1).

In some embodiments, the COB is composed of one or more assayable polymer subunit (APS). Certain aspects of the present invention relate to the selection of a library or population of designed (e.g., synthetic sequences) APS. In some embodiments, the present invention provides a population of designed (e.g. synthetic) APS wherein said APS comprises an unique sequence and/or a detectable molecule, and wherein the combination of one or more different APS in each COB has a detectable signal or sequence that distinguishes it from other COBs in said population. In some embodiments, the invention provides APSs comprising unique sequences (e.g. synthetic) that hybridize to a unique complementary polynucleotide sequence having attached thereto a detectable label. In some embodiments, the APS are detected by sequencing. Accordingly, certain aspects of the present invention provide a population of unique COBs or ESB/COBs, each comprised of a unique APS-based combination, wherein each COBs or ESB/COBs in the population is distinct from the other COBs or ESB/COBs in the population. APSs generally are capable of forming a construct comprising the COBs. Any chemical structure allowing for such formation can be used for the APSs.

Unique Binding Agent (UBA)

UBAs are molecules or assemblies that are designed to bind with at least one target molecule, at least one target molecule surrogate, or both; and can, under appropriate conditions, form a molecular complex comprising the UBA and the target molecule. Examples of target molecules include, but are not limited to, proteins, nucleic acids, lipids, carbohydrates, ions, small molecules, organic monomers, and drugs. For convenience only, most of the embodiments described herein are explained in the context of UBAs that bind to a target protein or a target mRNA. However, these embodiments also can be applied to other target molecules. The terms "protein", "polypeptide", "peptide", and "amino acid sequence" are used interchangeably herein to refer to polymers of amino acids of any length. The polymer may be linear or branched, it may comprise modified amino acids, and it may be interrupted by non amino acids or synthetic amino acids. The terms also encompass an amino acid polymer that has been modified, for example, by disulfide bond formation, glycosylation, lipidation, acetylation, phosphorylation, or any other manipulation, such as conjugation with a labeling component. As used herein the term "amino acid" refers to either natural and/or unnatural or synthetic amino acids, including but not limited to glycine and both the D or L optical isomers, and amino acid analogs and peptidomimetics.

UBAs comprise at least one reaction portion that allow them to bind to or interact with at least one target molecule, at least one part of at least one target molecule, at least one target molecule surrogate, at least part of a target molecule surrogate, or combinations thereof; typically in a sequence-specific, a confirmation-specific manner, or both; for example but not limited to antigen-antibody binding, aptamer-target binding, and the like.

In certain embodiments, the UBAs comprise an identity portion or at least part of an identity portion, for example, an ESB, a COB, an ESB and/or a linker oligo. In certain embodiments, the UBAs comprise a capture region. In some embodiments, the capture region is used for the isolation of the UBA and/or immobilization of the UBA into a surface. The capture region can be an affinity tag, a bead, a slide, an array, a microdroplet, an enclosure in a microfluidic device or any other suitable capture region in the art. In some embodiments, the capture region is the ESB, for example the ESB can be a detectable bead such as a bead with a unique spectral signature (e.g. a bead that has been internally dyed with red and infrared fluorophores). Capture regions can define reaction volumes in which manipulation of compositions of the invention can take place.

In some embodiments, the UBA is an antibody. As used herein, the terms antibody and antibodies are used in a broad sense, to include not only intact antibody molecules, for example but not limited to immunoglobulin A, immunoglobulin G and immunoglobulin M, but also any immunoreactive component(s) of an antibody molecule that immunospecifically bind to at least one epitope. Such immunoreactive components include but are not limited to, FAb fragments, FAb' fragments. FAb'2 fragments, single chain antibody fragments (scFv), miniantibodies, diabodies, crosslinked antibody fragments, Affibody™, cyclotides, molecules, and the like. Immunoreactive products derived using antibody engineering or protein engineering techniques are also expressly within the meaning of the term antibodies. Detailed descriptions of antibody and/or protein engineering, including relevant protocols, can be found in, among other places, J. Maynard and G. Georgiou, Ann. Rev. Biomed. Eng. 2:339 76 (2000); Antibody Engineering, R. Kontermann and S. Dubel, eds., Springer Lab Manual, Springer Verlag (2001); U.S. Pat. No. 5,831,012; and S. Paul, Antibody Engineering Protocols, Humana Press (1995).

The skilled artisan will appreciate that antibody can be obtained from a variety of sources, including but not limited to polyclonal antibody, monoclonal antibody, monospecific antibody, recombinantly expressed antibody, humanized antibody, plantibodies, and the like; and can be obtained from a variety of animal species, including rabbit, mouse, goat, rat, human, horse, bovine, guinea pig, chicken, sheep, donkey, human, and the like. A wide variety of antibodies are commercially available and custom-made antibodies can be obtained from a number of contract labs. Detailed descriptions of antibodies, including relevant protocols, can be found in, among other places, Current Protocols in Immunology, Coligan et al., eds., John Wiley & Sons (1999, including updates through August 2003); The Electronic Notebook; Basic Methods in Antibody Production and Characterization, G. Howard and D. Bethel, eds., CRC Press (2000); J. Goding, Monoclonal Antibodies: Principles and Practice, 3d Ed., Academic Press (1996); E. Harlow and D. Lane, Using Antibodies, Cold Spring Harbor Lab Press (1999); P. Shepherd and C. Dean, Monoclonal Antibodies: A Practical Approach, Oxford University Press (2000); A. Johnstone and M. Turner, Immunochemistry 1 and 2, Oxford University Press (1997); C. Borrebaeck, Antibody Engineering, 2d ed., Oxford university Press (1995); A. Johnstone and R. Thorpe, Immunochemistry in Practice, Blackwell Science, Ltd. (1996); 11. Zola, Monoclonal Antibodies: Preparation and Use of Monoclonal Antibodies and Engineered Antibody Derivatives (Basics: From Background to Bench), Springer Verlag (2000); and S. Hockfield et al., Selected Methods for Antibody and Nucleic Acid Probes, Cold Spring Harbor Lab Press (1993). Additionally, a vast number of commercially available antibodies, including labeled or unlabeled; polyclonal, monoclonal, and monospecific antibodies, as well as immunoreactive components thereof; custom antibody suppliers and the like can be found on the World Wide Web at, among other places, the Antibody Search page at biocompare.com, the Antibody Resource Page at antibodyresource.com, and the Antibody Explorer page at sigmaaldrich.com.

In some embodiments, the antibodies described herein are attached to a nucleic acid, e.g., linker oligo or a nucleic acid ESB. Methods to attach nucleic acids to antibodies are known in the art. Any suitable method to attach nucleic acids to antibodies is encompassed in the methods of the invention. The antibodies described herein can be attached to a nucleic acid by the methods described in Gullberg et al., PNAS 101 (22): pages 228420-8424 (2004); and Boozer et al, Analytical Chemistry, 76(23): pages 6967-6972 (2004), both incorporated herein by reference. The antibodies described herein can be attached to a nucleic acid by random amine attachment. In some embodiments, the antibodies described herein can be attached to a nucleic acid by random amine attachment using a 10 to 1 ratio of nucleic acid to antibody. The antibodies described herein can be attached to a nucleic acid by the methods described in Kozlov et al., Biopolymers 5: 73 (5): pages 621-630 (2004) incorporated herein by reference. The antibodies described herein can be attached to a nucleic acid by hydrazine chemistry. The antibodies described herein can be attached to a nucleic acid using tadpoles as described in Nolan, Nature Methods 2, 11-12 (2005), incorporated herein by reference. The antibodies described herein can be attached to a nucleic acid by any suitable methods known in the art to generate engineered antibodies including the ones described herein.

In some embodiments, the UBA is an aptamer. Aptamers include nucleic acid aptamers (i.e., single-stranded DNA molecules or single-stranded RNA molecules) and peptide aptamers. Aptamers bind target molecules in a highly specific, conformation-dependent manner, typically with very high affinity, although aptamers with lower binding affinity can be selected if desired. Aptamers have been shown to distinguish between targets based on very small structural differences such as the presence or absence of a methyl or hydroxyl group and certain aptamers can distinguish between D- and L-enantiomers. Aptamers have been obtained that bind small molecular targets, including drugs, metal ions, and organic dyes, peptides, biotin, and proteins, including but not limited to streptavidin, VEGF, and viral proteins. Aptamers have been shown to retain functional activity after biotinylation, fluorescein labeling, and when attached to glass surfaces and microspheres.

Nucleic acid aptamers, including speigelmers, are identified by an in vitro selection process known as systematic evolution of ligands by exponential amplification (SELEX). In the SELEX process very large combinatorial libraries of oligonucleotides, for example 1014 to 1015 individual sequences, often as large as 60-100 nucleotides long, are routinely screened by an iterative process of in vitro selection and amplification. Most targets are affinity enriched within 8-15 cycles and the process has been automated allowing for faster aptamer isolation. Peptide aptamers are typically identified by several different protein engineering techniques known in the art, including but not limited to, phage display, ribosome display, mRNA display, selectively infected phage technology (SIP), and the like. The skilled artisan will understand that nucleic acid aptamers and peptide aptamers can be obtained following conventional procedures and without undue experimentation. Detailed descriptions of aptamers, including relevant protocols, can be found in, among other places, L. Gold, J. Biol. Chem., 270(23):13581 84 (1995); S. Jayasena, Clin. Chem. 45:1628-50 (1999); V. Sieber et al., Nat Biotechnol. 16 (10):955-60 (1998); D. Wilson and J. Szostak, Ann. Rev. Biochem. 68:611-47 (1999); L. Jermutus et al., Eur. Biophys. J., 31:179-84 (2002); S S. Spada et al., Biol. Chem., 378:445-56 (1997); B. Wlotzka et al., Proc. Natl. Acad. Sci., 99:8898-8902 (2002).

In some embodiments the aptamer will be ligated or hybridized to nucleic acid such as a linker oligo or a nucleic acid ESB. The hybridization or ligation of aptamers can be done by any suitable method known in art. For example ligation can be performed enzymatically by at least one DNA ligase or at least one RNA ligase, for example but not limited to, T4 DNA ligase, T4 RNA ligase, *Thermus thermophilus* (Tth) ligase, *Thermus aquaticus* (Taq) DNA ligase, or *Pyrococcus furiosus* (Pfu) ligase. Ligation can also be performed by chemical ligation can, using activating and reducing agents such as carbodiimide, cyanogen bromide (Brynn), imidazole, 1-methylimidazole/carbodiimide/cystamine, N-cyanoimidazole, dithiothreitol (DTTP) and ultraviolet light.

In some embodiments, the UBA is a peptoid. Peptoids are short sequences of N-substituted glycines synthetic peptides that bind proteins. In some embodiments, small size peptoids improve diffusion and kinetics of the methods described herein. Any suitable method known in the art to generate peptoids is encompassed in the methods described herein. See Simon et al., PNAS 15; 89(20): 9367-9371 (1992), incorporated herein by reference.

In some embodiments, the UBA is a nucleic acid sequence, e.g. an antisense DNA for a target mRNA. The nucleic acid sequence is preferably at least 15 nucleotides in length, and more preferably is at least 20 nucleotides in length. In specific embodiments, the target-specific sequence is about 10 to 500, 20 to 400, 30 to 300, 40 to 200, or 50 to 100 nucleotides in length. In other embodiments, the target-specific sequence is about 30 to 70, 40 to 80, 50 to 90, or 60 to 100, 30 to 120, 40 to 140, or 50 to 150 nucleotides in length.

Epitope Specific Barcode (ESB)

In some embodiments, the invention provides an epitope specific barcode (ESB). Each ESB comprises a unique code that can be associated to a specific target molecule. ESBs are molecules or assemblies that are designed to bind with at least one UBA or part of an UBA; and can, under appropriate conditions, form a molecular complex comprising the ESB, the UBA and the target molecule.

ESBs can comprise at least one identity identification portion that allow them to bind to or interact with at least one UBA; typically in a sequence-specific, a confirmation-specific manner, or both; for example but not limited to UBA-antibody binding, aptamer-target binding, and the like. In some embodiments, the ESB are attached, directly or indirectly, to the UBA. In other embodiments, the ESBs bind to the UBAs in a cell or sample, e.g., as part of the assay procedure.

In certain embodiments, the ESB is a solid surface or a capture region, for example, the ESB can be a detectable bead such as a bead with a unique spectral signature (e.g. a bead that has been internally dyed with red and infrared fluorophores). In some embodiments, the UBA is directly or indirectly attached to the capture region.

In certain embodiments, the ESBs comprise common linker moiety, for example, a linker oligo. In certain embodiments, the common linker oligo is complementary to a common linker oligo in the assayable polymer subunits (APSs) that form the cell origination barcode (COB).

In certain embodiments, the ESBs comprise a capture region. In some embodiments, the capture region is used for the isolation of the ESB and/or immobilization of the ESB into a surface. The capture region can be an affinity tag, a bead, a slide or an array. In some embodiments, the capture region is a detectable bead such as a bead with a unique spectral signature (e.g. a bead that has been internally dyed with red and infrared fluorophores In some embodiments, the ESB is an antibody or fragment thereof, an aptamer, a nucleic acid, or peptoid, as described above.

In some embodiments, the ESB is a nucleic acid. In some embodiments, a part of the nucleic acid is amplified with branch chain or rolling circle approaches as known in the art.

In some embodiments, the ESB is a peptoid. Peptoids are short sequences of N-substituted glycines synthetic peptides that bind proteins. In some embodiments, small size peptoids improve diffusion and kinetics of the methods described herein. Any suitable method known in the art to generate peptoids is encompassed in the methods described herein. See Simon et al., PNAS 15; 89(20): 9367-9371 (1992), incorporated herein by reference.

In some embodiments, the ESB is a nucleic acid sequence, e.g. an antisense nucleic acid for a complementary target nucleic acid sequence. The nucleic acid sequence is preferably at least 15 nucleotides in length, and more preferably is at least 20 nucleotides in length. In specific embodiments, the target-specific sequence is about 10 to 500, 20 to 400, 30 to 300, 40 to 200, or 50 to 100 nucleotides in length. In other embodiments, the target-specific sequence is about 30 to 70, 40 to 80, 50 to 90, or 60 to 100, 30 to 120, 40 to 140, or 50 to 150 nucleotides in length.

Cell Origination Barcode (COB)

In some embodiments, the invention provides a cell origination barcode (COB). Each COB provides a unique code that can be associated to a specific cell of origin. In some embodiments, upon binding of the COB to a common linker moiety (e.g. common linker oligo) associated with an ESB, the COB code identifies the cells of origin of the target molecule to which the UBA/ESB complex is bound. Thus, in some embodiments the COBs of the invention comprise two main portions: (i) a sequence specific for a common linker moiety (e.g. common linker oligo) associated with a UBA/ESB probe; and (ii) an unique code that can be associated to a specific cell of origin.

In some embodiments, COBs are modular structures. In some embodiments, the COB comprises a plurality of different assayable polymer subunits (APS). In some embodiments, the COBs comprise a plurality of APSs attached in linear combination. In some embodiments, a COB is a molecular entity containing certain basic elements: (i) a plurality of APSs comprising label attachment regions attached in linear combination to form a backbone, and (ii) complementary polynucleotide sequences, comprising a label, which are complementary and are attached to the label attachment regions of the backbone. The term label attachment region includes a region of defined polynucleotide sequence within a given backbone that may serve as an individual attachment point for a detectable molecule. In some embodiments, the COBs comprise a plurality of different APSs attached in linear combination, wherein the APSs comprise small molecules of deterministic weight. In some embodiments, the COB comprises 2, 3, 4, 5, 6, 7, 8, 9, 10 or more unique APSs attached in a linear combination. In some embodiments, the COB comprises 4 or more APSs attached in linear combination.

In some embodiments, the plurality of APSs attached in linear combination can comprise uniquely designed nucleic acid sequences. In addition, the plurality of APSs attached in linear combination in the COBs can comprise at least one template, for example but not limited to, at least one nucleic acid sequence, such as at least part of a linear or linearizable viral genome, such as the genomes of adenovirus, hepatitis virus, herpes virus, rotavirus, and the like, or bacteriophages such as lambda, M13, φX-174, T-series bacteriophages, and the like, including derivatives thereof comprising cloning cassettes, polylinkers, and the like; plasmids, such as pBR322 and pUC series plasmids, etc., including derivatives thereof comprising cloning cassettes, polylinkers, and the like; synthetic templates; templates comprising artificial sequences; and the like. The skilled artisan will understand that virtually any piece of nucleic acid can serve as a template for fabricating a COB provided that it is large enough to include at least two APSs, or it can be combined with at least one other nucleic acid sequence so that the combined sequence is large enough to include at least two APSs. In some embodiments, ESBs, APSs, or COBs of the invention relate to templatable building blocks. In some embodiments, UBAs of the invention relate to templatable molecules.

In some embodiments, the COB also comprises one or more APSs containing a common linker moiety (e.g. common linker oligo). The common linker moiety can be directly or indirectly attached to the APSs. Thus, the common linker moiety can be covalently attached to a COB or the common linker moiety can be bound to the COB later in the assay. The term common linker moiety includes tandemly-repeated sequences of about 10 to about 25 nucleotides. The common linker moiety can be attached at either the 5' region or the 3' region of a COB, and may be utilized for capture and immobilization of a COB for imaging or detection, such as by attaching to a solid substrate a sequence that is complementary to the common linker moiety.

The elements of a COB can be found in a single molecular entity (a singular COB), or two distinct molecular entities (a dual COB). Each molecular entity may be composed of one molecule or more than one molecule attached to one another by covalent or non-covalent means. In some embodiments, each component of a dual COB has a target molecule-specific UBA/ESB that binds to a different site on the same target molecule. When using a dual COB system one of the COBs may be unlabeled. In some embodiments, the unlabeled COB may comprise a capture region.

In various embodiments of the invention a COB is constructed from individual APS building blocks. In some embodiments, the APSs are combined linearly. In some embodiments, the COB constructed from the APSs maintains the order of the APS. In some embodiments, COBs comprise branched structures. In some embodiments, the branched COB structures comprise information about the order of APS addition. In various embodiments, the individual APS forming a COB can be decoded. In some embodiments, the order or order of addition of the APSs forming the COB can be decoded. Without being bound by theory, platforms allowing the APS addition order to be protected and decoded lend for a higher number of different COBs to be generated from equivalent number of APS building blocks. With a higher number of total COB molecule types, the likelihood of two cells/particles in a population being labeled with the same COB decreases. Thus, the methods of various embodiments of the invention allow for a higher statistical significance for the determination of cell/particle identity.

In some embodiments, the complementary polynucleotide sequences attached to an APS serve to attach detectable molecules, or label monomers, to the APS. The complementary polynucleotide sequences may be directly labeled, for example, by covalent incorporation of one or more detectable molecules into the complementary polynucleotide sequence. Alternatively, the complementary polynucleotide sequences may be indirectly labeled, such as by incorporation of biotin or other molecule capable of a specific ligand interaction into the complementary polynucleotide sequence. In such instances, the ligand (e.g., streptavidin in the case of biotin incorporation into the complementary polynucleotide sequence) may be covalently attached to the detectable molecule. Where the detectable molecules attached to an APS are not directly incorporated into the complementary polynucleotide sequence, this sequence serves as a bridge between the detectable molecule and the APS, and may be referred to as a bridging molecule, e.g., a bridging nucleic acid.

In some embodiments, the nucleic-acid based COBs, COB-ESB complexes, or COB/ESB/UBA complexes of the present invention comprise nucleic acids, which may be affinity-purified or immobilized using a nucleic acid, such as an oligonucleotide, that is complementary to a constant region of the COB (e.g. common linker moiety, capture region or affinity tag). As noted above, in some embodiments the COBs comprise at least one common linker moiety, which may serve as an affinity tag for purification and/or for immobilization (for example to a solid surface). The common linker moiety can comprises two or more tandemly-repeated regions of repeat nucleotides, such as a series of 15-base repeats. In such exemplary embodiments, the COB, whether complexed to an ESB, ESB/UBA, a target molecule/UBA/ESB or otherwise, can be purified or immobilized by an affinity reagent coated with a 15-base oligonucleotide which is the reverse complement of the repeat unit.

COBs, COB-ESB complexes, or COB/ESB/UBA complexes can be purified in two or more affinity selection steps. For example, in the embodiments in which the COB is attached to an ESB/UBA complex, the COB can comprise an affinity tag. In other embodiments when a dual COB is used, one COB can comprise a first affinity tag and the other COB can comprise a second (different) affinity tag. The COBs are mixed with the target molecules, and complexes comprising the two probes of the dual COBs are separated from unbound materials by affinity purification against one or both individual affinity tags.

In the first step, the mixture can be bound to an affinity reagent for the first affinity tag, so that only probes comprising the first affinity tag and the desired complexes are purified. The bound materials are released from the first affinity reagent and optionally bound to an affinity reagent for the second affinity tag, allowing the separation of complexes from COBs comprising the first affinity tag. At this point only full complexes would be bound. The complexes are finally released from the affinity reagent for the second affinity tag and then analyzed by the methods described herein. The affinity reagent can be any solid surface coated with a binding partner for the affinity tag, such as a column, bead (e.g., latex or magnetic bead) or slide coated with the binding partner. A variety of affinity tags known in the art may be used, e.g., to purify and/or immobilize COBs, COB-ESB complexes, or COB/ESB/UBA complexes. In some embodiments, a biotin anchor is attached to the COB, ESB and/or UBA, allowing immobilization of the COBs, COB-ESB complexes, or COB/ESB/UBA complexes on a streptavidin surface (e.g. coated slide or bead). In some embodiments, an affinity tag is attached to a UBA, e.g., to purify and/or immobilize the UBA. An affinity tag can be used for attachment to beads or other matrixes for a variety of useful applications including but not limited to purification. Examples of affinity tags and methods of making and/or attaching them to the nucleic acids are described in U.S. Pat. No. 7,473,767; U.S. application Ser. Nos. 10/542,458; 12/324,357; 11/645,270 and 12/541,131, incorporated herein by reference in their entirety. In some embodiments, at least two of ESB, UBAs, APSs, and COBs comprise different chemical compositions described herein or any other suitable composition known in the art. For example, an ESB can comprise a peptide and/or a nucleic acid, while an APS comprises a peptide or a peptoid. Any combination of described chemistries are envisioned within the scope of the invention.

In various embodiments, ESBs, APSs and/or COBs can be template, ordered, and or decoded. In some embodiments, the order of any of these subunits in a construct can be detected. ESBs, APSs and/or COBs can provide templates for the addition of any of another one of ESBs, APSs and/or COBs, for example via nucleic acid or any other suitable chemical complementarity known in the art. ESBs, APSs and/or COBs may encode secondary products, such as a nucleic acid encoding for another nucleic acid or a peptide. In some embodiments, the detection of the ESBs, APSs and/or COBs comprises decoding the same, for example generating an amplicon or expressing a peptide from the ESBs, APSs and/or COBs and sequencing or otherwise detecting the products.

The sequences, the weights or the signals provided by the label monomers associated with the various APS of the COB of a given cell allow for the unique identification of the COB. For example, when using nucleic acid sequences, a COB having a unique identity or unique sequence signature is associated with a UBA that recognizes a specific target molecule or a portion thereof. Detection of the COB sequence allows for the detection of the presence of the target molecule in the mixture (qualitative analysis). In another example, when using fluorescent labels, a COB having a unique identity or unique spectral signature is associated with a UBA that recognizes a specific target molecule or a portion thereof. Detection of the COB signal, such as the spectral code of a fluorescently labeled COB allows detection of the presence of the target molecule in the mixture (qualitative analysis). In yet another example, when using small molecules as per combinatorial synthesis procedure, a COB having a unique deterministic weight is associated with a UBA that recognizes a specific target molecule or a portion thereof. Detection of the COB deterministic weight (e.g., via mass spectrometry) allows detection of the presence of the target molecule in the mixture (qualitative analysis). Counting and or quantifying the codes (e.g. sequences, label monomers, or deterministic weights) associated with a given signature (e.g. spectral code, unique sequence, or unique deterministic weight) allow the counting or quantitation of all the molecules in the mixture associated the UBA coupled to the COB (quantitative analysis). UBA/ESB/COB complexes are thus useful for the diagnosis or prognosis of different biological states (e.g., disease vs. healthy) by quantitative analysis of known biological markers.

Moreover, the exquisite sensitivity of single molecule detection and quantification provided by the COBs of the invention allows for the identification of new diagnostic and prognostic markers, including those whose fluctuations among the different biological states is too slight to detect a correlation with a particular biological state using traditional molecular methods. The sensitivity of COB-based molecular detection permits detailed pharmacokinetic analysis of therapeutic and diagnostic agents in small biological samples.

COB syntheses can be performed by any suitable methods known in the art, including the one described herein.

In various embodiments, the invention relates to a COB to be synthesized by stepwise addition of assayable polymer subunits (APSs) comprising oligonucleotides. The COB can be attached to the UBA via a common linker (CL). The CL can also be part of an oligonucleotide. In some embodiments, an epitope specific barcode is also provided as an oligonucleotide. In some instances, the epitope specific barcode can be included in the oligonucleotide that comprises the common linker. In some embodiments, CL, ESB and APSs all comprise oligonucleotide sequences. Accordingly, an oligonucleotide CL may be ligated to an oligonucleotide ESB or APS. Substantially complementary or exact complementary annealing regions may be utilized for hybridization. An annealing region may be provided on both ends of an oligonucleotide ESB or APS. In some embodiments, the APSs are added in various steps of a split pool synthesis or any other suitable stepwise synthesis known in the art. An annealing region specific to each step of a stepwise synthesis maybe incorporated into the oligonucleotides. Without being bound by theory, if an oligonucleotide addition is skipped during a step, the step-specific annealing region of the next oligonucleotide will not hybridize efficiently to the step-specific annealing region of the previous oligonucleotide that is available. Thus, the some embodiments of the invention provide methods to stall the synthesis of COBs missing one or more APSs.

Figure 6:
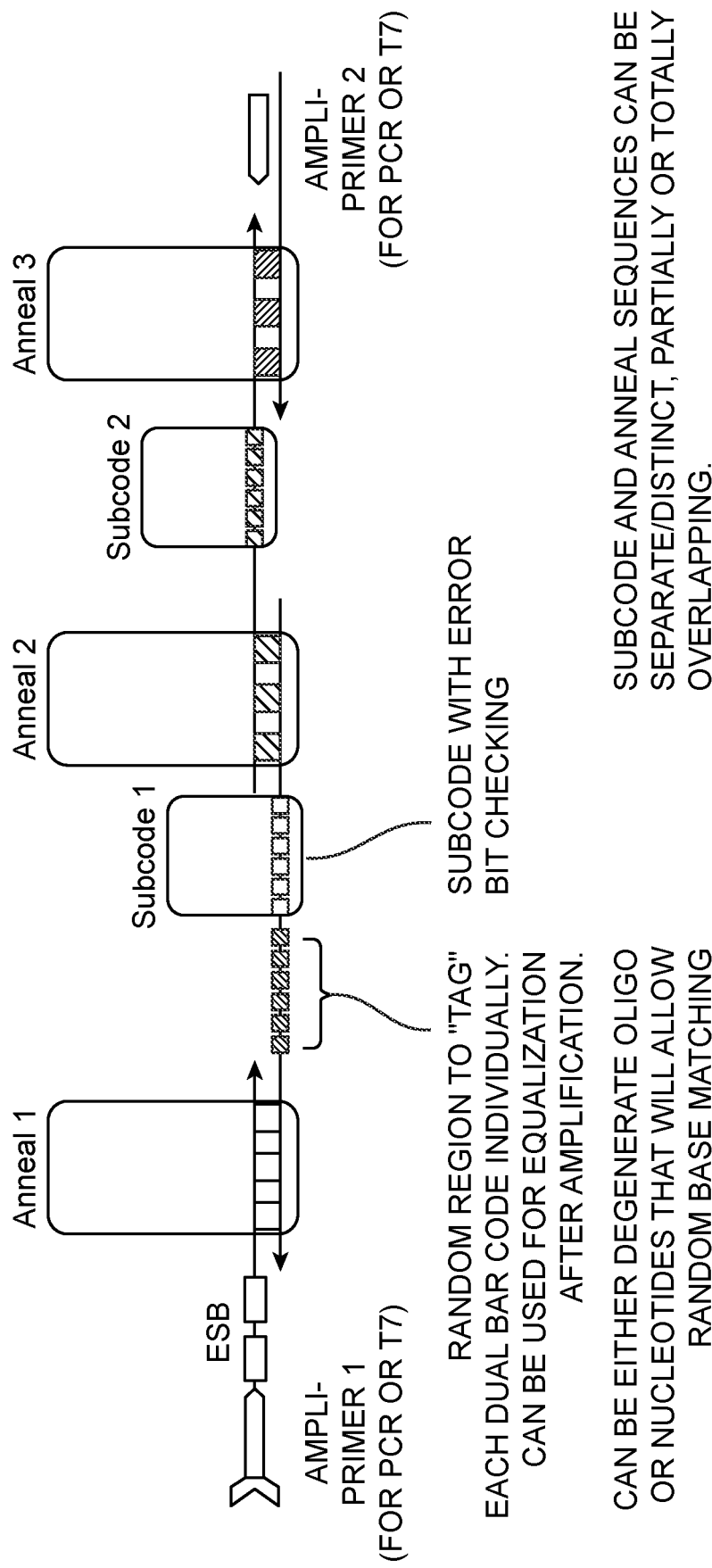
FIG. 6 depicts ESB-COB assembly according to one embodiment of the invention.

In some embodiments, UBAs are labeled with different CL oligonucleotides, each with a unique ESB sequence specific to the UBA and a common annealing region. In many cases, the APSs are assembled into COBs during the rounds of split pool synthesis. In these cases, in each round, the sample is split into n different containers. A different oligonucleotide APS can be added to each container, totaling m different APSs. In some embodiments n and m are the same. In other embodiments, n is greater than m or m is greater than n. Each APS can be designed so that it will selectively hybridize an annealing region added during the round before (FIG. 6). In various embodiments, a pair of round-specific annealing regions is incorporated in each APS. The annealing regions can be incorporated to each end of the APS. The annealing regions incorporated to each end of an APS can be different. Accordingly, an annealing region of an added APS can be complementary to an available annealing region from a previous round facilitating assembly.

Figure 7:
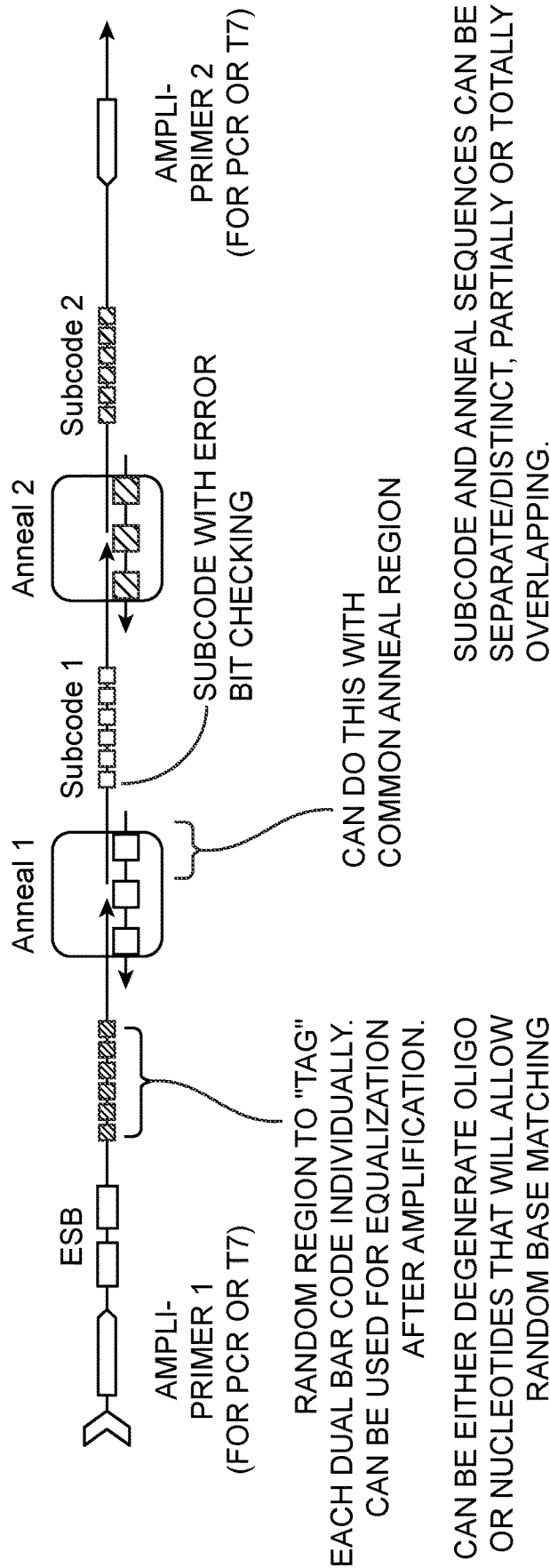
FIG. 7 depicts ESB-COB assembly according to another embodiment of the invention.
Figure 8:
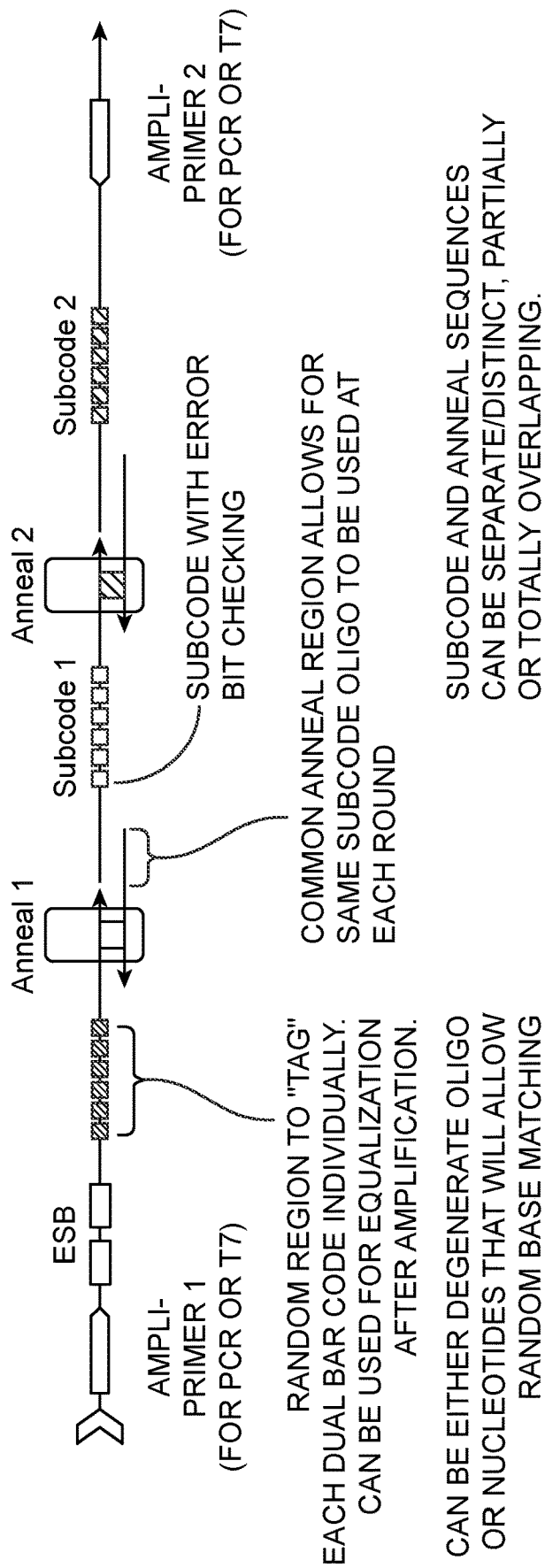
FIG. 8 depicts ESB-COB assembly according to another embodiment of the invention.

In some embodiments, the APSs are stitched together and/or to a CL using an annealing primer (FIGS. 7 and 8). The annealing primer may comprise a first complementary region to the CL or an APS added during the previous round of a stepwise synthesis. The annealing primer may also comprise a second complementary region to the APS being added during a current round. Thus, the annealing primer can hybridize to two oligonucleotide subunits of subsequent rounds stitching them together. In some embodiments, the first complementary regions of annealing primers of each round are different from the first complementary regions of annealing primers of other rounds (FIG. 7). In some embodiments, the second complementary regions of annealing primers of each round are different from the second complementary regions of annealing primers of other rounds. In some embodiments, the first or second complementary regions of annealing primers of different rounds are shared between rounds (FIG. 8).

Figure 9:
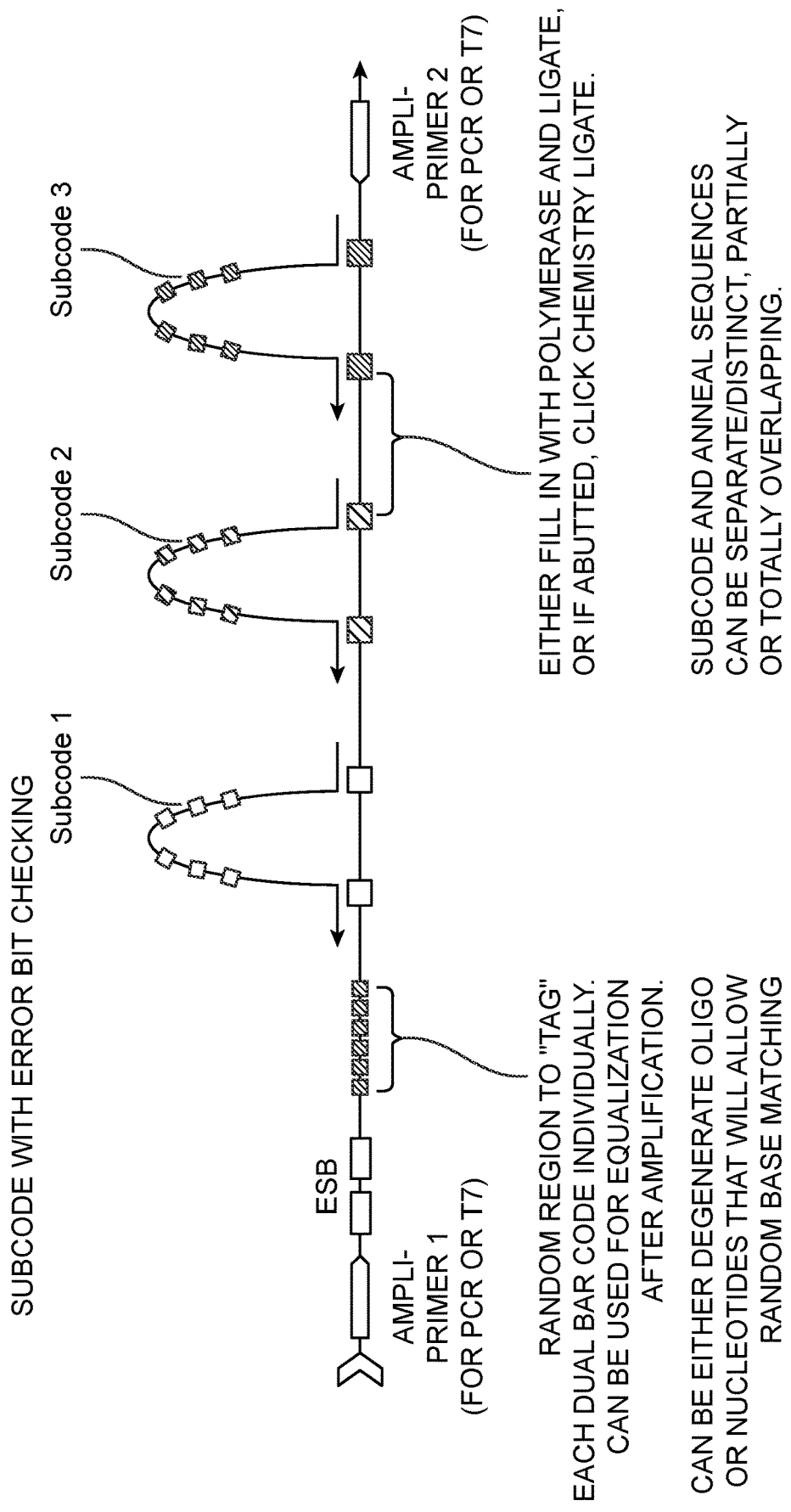
FIG. 9 depicts ESB-COB assembly according to another embodiment of the invention.
Figure 10:
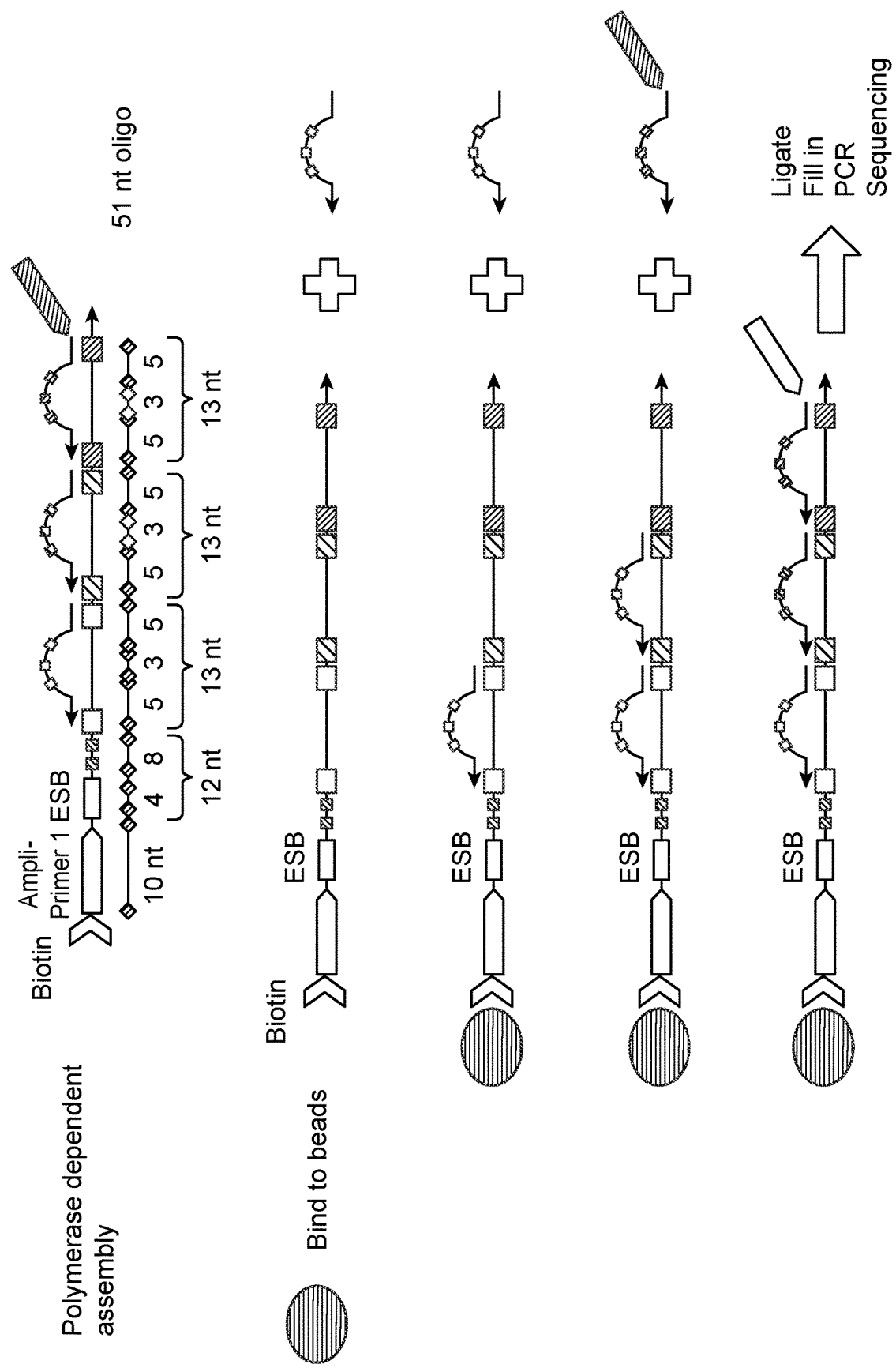
FIG. 10 depicts ESB-COB assembly according to another embodiment of the invention.
Figure 10:
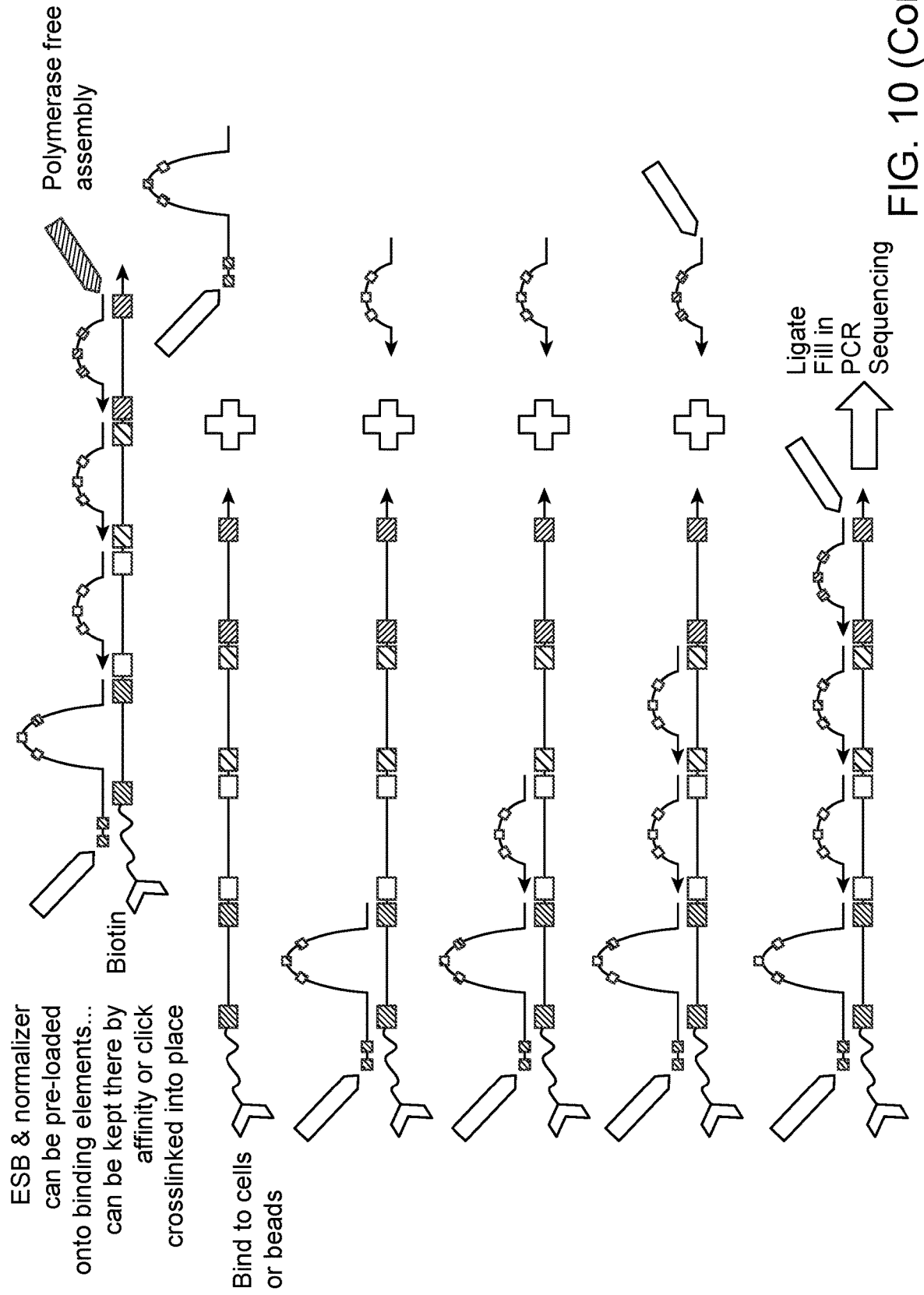

In some embodiments, a CL oligonucleotide comprises pairs of loop annealing regions (FIGS. 9 and 10). Accordingly, APSs can be designed to hybridize to the CL in a loop geometry, hybridizing on each end to the CL along the loop annealing regions. The loop annealing regions can be specific to the round. The hybridization can populate the APSs along the CL. The APSs can be linked together using any method described herein or other common methods known in the art. The APSs can be designed such that they do not efficiently hybridize to the CL along the loop annealing regions specific to other rounds. Consequently, if an APS from a particular round is missing, the APSs may not be linked together successfully, depending on the linking process. Alternatively, a COB may be synthesized with a missing APS, the location of which is flanked by a pair of loop annealing regions. The resulting COB can then be analyzed accordingly and can either be discarded or the retrieved information can be alternatively processed.

Each APS in a given round can comprise a unique subcode sequence that is different from the rest of the APSs in that round (FIGS. 6-11). The subcode may comprise a unique nucleotide sequence.

A CL, or one or more APSs may further comprise a random tag region allowing for subsequent normalization of the detected COBs (FIGS. 6-11). Variations of suitable methods making use of such random tag regions are known in the art, e.g., see Casbon et al. (Nucleic Acids Research, 2011, 39:12, c81). In some cases, the random tag region can function as a molecular counter to estimate the number of template molecules associated with each sequence variant. In some cases, a molecular counter is incorporated into a CL, ESB, APS or an assembled COB prior to an amplification reaction, e.g. PCR. A library of molecular counters comprising degenerate base regions (DBR) may be incorporated into CLs, ESBs, APSs or assembled COBs. The number of unique DBRs in a library generally is limited by the length and base composition of the DBR. For example, a single nucleotide in a DBR would allow for four different possible counters, one for each base. Longer DBRs can produce higher numbers of unique counter sequences. A molecular counter from a library of sequences can each be incorporated in a CL, ESB, APS or an assembled COB. The molecular counter can be used to determine whether a sequence variant is associated with a single template molecule, or alternatively, multiple template molecules. The number of different DBR sequences associated with one sequence variant can serve as a direct measure of the number of initial template molecules. This information can supplement or replace the information provided by read numbers of each sequence variant, including, for example, read numbers after an amplification reaction, e.g. PCR. DBRs can also be used to determine the probability that a sequence variant derives from a polymerase error during an amplification reaction or is a true original variant prior to an amplification reaction, e.g. PCR. In some embodiments, unique binding agents (UBAs) are fixed to their targets prior to or concurrent with the assembly of COBs.

Various embodiments of the invention relate to the assembly of COBs on the surface of cells. COBs can, for example, be assembled associated with UBAs targeting cell surface components. In some embodiments, UBAs are fixed to cell surface components prior to or concurrent with the assembly of COBs. In some embodiments, UBAs are delivered into cells or into cellular compartments. In some embodiments, COBs are assembled associated with UBAs within cells or cellular compartments. Cells may be fixed prior to the addition of UBAs, ESBs or prior to COB assembly. Suitable cell permeabilization methods are known in the art and can be used to deliver components of the assay into cells and cellular components.

In some embodiments, the assay is performed on bodies that are not cells. Suitable support materials known in the art, such as beads or surface coatings, can act in the same manner a cell would act to provide an original binding surface. Support materials can be decorated with binding targets. In some embodiments, support materials spatially resolve binding targets from each other.

In some embodiments, the assay may comprise primary binding targets and one or more secondary binding targets that are capable of binding to the primary target. A support material, can for example, be coated with one or more primary targets. A library of secondary targets can be provided to bind the primary targets. UBAs can be provided to bind epitopes of primary and/or secondary targets. COBs can be assembled associated with these UBAs as described for other types of targets. Inter-dependent binding of secondary targets to primary targets can be monitored by analyzing the COBs.

In some embodiments, multiple COBs are assembled on the same UBA molecule.

In some embodiments, the ESBs or assembled COBs encode a derivative sequence. In some embodiments, the ESBs and/or COBs comprise a polynucleotide sequence. In some cases, the ESB and/or COB can encode an RNA sequence. In some cases, the ESB and/or the COB encode a peptide sequence. The ESB and/or the COB can encode for the peptide sequence directly. Alternatively, the COB can encode for a peptide sequence indirectly, for example, through an intermediary RNA sequence. For example, a polynucleotide ESB or COB can encode an open reading frame. In some cases, the peptide sequence is translated after introducing the ESB or COB into a construct enabling peptide expression. In some embodiments, the construct is a vector.

In some embodiments, the ESBs and COBs are assembled from oligonucleotides. The linking agent can be a ligase. In some embodiments the ligase is T4 DNA ligase, using well known procedures (Maniatis, T. in Molecular Cloning, Cold Spring Harbor Laboratory (1982)). Other DNA ligases may also be used. With regard to ligation, other ligases, such as those derived from thermophilic organisms may be used thus permitting ligation at higher temperatures allowing the use of longer oligonucleotides (with increased specificity) as ESBs, CLs or APSs, which could be annealed and ligated simultaneously under the higher temperatures normally permissible for annealing such oligonucleotides. The ligation, however, need not be by an enzyme and, accordingly, the linking agent may be a chemical agent which will cause the ESB and APSs to link unless there is a nucleotide base pair mismatching at the annealing region. For simplicity, some embodiments of the invention will be described using T4 DNA ligase as the linking agent. This enzyme requires the presence of a phosphate group on the 5' end that is to be joined to a 3' OH group on a neighboring oligonucleotide.

When oligos are stacking together to bind to an annealing region with a perfect match at the junction at their ends, it results in a specific binding to the annealing region. The CLs, ESBs and APSs can be ligated to form an ESB linked COB. The ESB linked COBs, in turn, can be used for detection.

In some embodiments, the ESB and/or COB assembly comprises the use of CLICK chemistry. Suitable methods to link various molecules using CLICK chemistry are known in the art (for CLICK chemistry linkage of oligonucleotides, see, e.g. El-Sagheer et al. (PNAS, 108:28, 11338-11343, 2011).

In some embodiments, the ESB and/or COB assembly takes place inside a cell. In some embodiments, the ESBs and/or APSs are first assembled inside a cell. In some embodiments, the ESBs and/or APSs are linked inside a cell. In some embodiments, the ESBs and/or APSs are linked outside a cell.

In some embodiments, the assembled products are amplified and, optionally, the results are compared with amplification of similar target nucleic acids from a reference sample. In some embodiments, the ligated products of APSs are amplified and, optionally, results are compared with amplification of a similar COB from a reference sample. Amplification can be performed by any means known in the art. In some cases, the ligated products are amplified by polymerase chain reaction (PCR). Examples of PCR techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988, 617; and 6,582,938. In some embodiments, the amplification is performed inside a cell.

In any of the embodiments, amplification of ligated products may occur on a support, such as a bead or a surface. In any of the embodiments herein, COBs may be assembled on targets from a single cell.

The uniqueness of each UBA/ESB probe in a population of probes allows for the multiplexed analysis of a plurality of target molecules. Furthermore the uniqueness of each COB probe in a population of probes allows for the multiplexed analysis of a plurality of target molecules in single cells.

For example, in some embodiments, each COB contains six APSs. If the APSs are going to be sequenced and there are 20 possible unique sequences for the APS. There will be $3.84 \times 10^8$ possible COBs in this example. Thus, $3.84 \times 10^8$ cells and their corresponding UBA/ESB probes can be analyzed in this example. Given that in sequencing you don't have the color constraints present in some fluorescent methods, one can analyze multiple UBA/ESB probes per cells. In some embodiments, 10, 15, 20, 25, 30, 40, 50, 60, 65, 70, 90, 100 different UBA/ESBs are analyzed per cell. In some embodiments, up to 100 different UBA/ESBs are analyzed per cell. In some embodiments, up to 1000 different UBA/ESBs are analyzed per cell. In some embodiments, up to 2000 different UBA/ESBs are analyzed per cell.

In certain embodiments, the methods of detection are performed in multiplex assays, whereby a plurality of target molecules is detected in the same assay (a single reaction mixture). In a preferred embodiment, the assay is a hybridization assay or an affinity binding assay in which the plurality of target molecules is detected simultaneously. In a preferred embodiment, the assay is hybridization assay or an affinity binding assay in which the plurality of target molecules is detected simultaneously in single cells. In certain embodiments, the plurality of target molecules detected in the same assay is, at least 2, at least 5 different target molecules, at least 10 different target molecules, at least 20 different target molecules, at least 50 different target molecules, at least 75 different target molecules, at least 100 different target molecules, at least 200 different target molecules, at least 500 different target molecules, or at least 750 different target molecules, or at least 1000 different target molecules. In other embodiments, the plurality of target molecules detected in the same assay is up to 50 different target molecules, up to 100 different target molecules, up to 150 different target molecules, up to 200 different target molecules, up to 300 different target molecules, up to 500 different target molecules, up to 750 different target molecules, up to 1000 different target molecules, up to 2000 target molecules, or up to 5000 target molecules. In yet other embodiments, the plurality of target molecules detected is any range in between the foregoing numbers of different target molecules, such as, but not limited to, from 20 to 50 different target molecules, from 50 to 200 different target molecules, from 100 to 1000 different target molecules, from 500 to 5000 different target molecules, and so on and so forth.

In some embodiments, the detection is digital detection. In some embodiments, the detection is direct, i.e. the method acquires a signal that is directly generated by the detected entity. In some embodiments, the detection is indirect, i.e. manipulation of an entity to be detected takes place before a signal is acquired. In some embodiments, a plurality of components of an entity to be detected give risk to detection signals directly or indirectly. In some embodiments, the order of the plurality of the components can be determined through the detection methods described herein. Such detection methods are also described as ordered detection methods or detection methods with ordered signals.

In any of the embodiments, the detection or quantification analysis of the COBs can be accomplished by sequencing. The APS subunits or entire COBs can be detected via full sequencing of all DNA tags by any suitable methods known in the art. e.g., Illumina HiSeq 2000, including the sequencing methods described herein.

Sequencing can be accomplished through classic Sanger sequencing methods which are well known in the art. Sequencing can also be accomplished using high-throughput systems some of which allow detection of a sequenced nucleotide immediately after or upon its incorporation into a growing strand, i.e., detection of sequence in red time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read.

In some embodiments, high-throughput sequencing involves the use of technology available by Illumina's HiSeq 2000 machine. This machine uses reversible terminator-based sequencing by synthesis chemistry. This machine can do 200 billion DNA reads in eight days.

In some embodiments, high-throughput sequencing involves the use of technology available by ABI Solid System. This genetic analysis platform that enables massively parallel sequencing of clonally-amplified DNA fragments linked to beads. The sequencing methodology is based on sequential ligation with dye-labeled oligonucleotides.

In some embodiments, high-throughput sequencing involves the use of technology available by Ion Torrent Personal Genome Machine (PMG). The PGM can do 10 million reads in two hours.

In some embodiments, high-throughput sequencing involves the use of technology available by Helicos BioSciences Corporation (Cambridge, Massachusetts) such as the Single Molecule Sequencing by Synthesis (SMSS) method. SMSS is unique because it allows for sequencing the entire human genome in up to 24 hours. This fast sequencing method also allows for detection of a SNP nucleotide in a sequence in substantially real time or real time. Finally, SMSS is powerful because, like the MIP technology, it does not require a pre amplification step prior to hybridization. In fact, SMSS does not require any amplification. SMSS is described in part in US Publication Application Nos. 2006002471 I; 20060024678; 20060012793; 20060012784; and 20050100932.

In some embodiments, high-throughput sequencing involves the use of technology available by 454 Lifesciences, Inc. (Branford, Connecticut) such as the Pico Titer Plate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density pricolitre reactors", Nature, doi: 10.1038/nature03959; and well as in US Publication Application Nos. 20020012930; 20030058629; 20030100102; 20030148344; 20040248161; 20050079510, 20050124022; and 20060078909.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106130; 20030064398; 20030022207; and Constans, A., The Scientist 2003, 17(13):36.

In some embodiments, high-throughput sequencing of RNA or DNA can take place using AnyDot.chjps (Genovoxx, Germany). In particular, the AnyDot-chips allow for 10×-50× enhancement of nucleotide fluorescence signal detection. AnyDot.chips and methods for using them are described in part in International Publication Application Nos. WO02/088382, WO03/020968, WO03/031947, WO2005/044836, PCT/EP05/105657, PCT/EP05/105655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 102005 012 301.

Other high-throughput sequencing systems include those disclosed in Venter, J., et al. Science 16 Feb. 2001; Adams, M. et al, Science 24 Mar. 2000; and M. J, Levene, et al. Science 299:682-686, January 2003; as well as US Publication Application No. 20030044781 and 2006/0078937. Overall such systems involve sequencing a target nucleic acid molecule having a plurality of bases by the temporal addition of bases via a polymerization reaction that is measured on a molecule of nucleic acid, i e., the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishably type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In various embodiments, oligonucleotide ESB or COBs are identified directly. The direct identification can comprise nucleic acid sequencing described supra. In some embodiments, the APS sequences encode for derivative sequences that are in turn identified. For example, a polynucleotide ESB and COB can be translated into a peptide sequence. The peptide sequence can then be identified using suitable methods known in the art.

In some embodiments, a sequence representing a COB or ESB is identified using mass spectrometric analysis. Sequencing methods comprising mass spectrometry are known in the art. In various embodiments, a derivative sequence, such as a peptide, is sequenced using mass spectrometric methods. In some embodiments, the mass spectrometric methods comprise fragmentation. In some embodiments, the mass spectrometric methods comprise N-terminal sequencing. In some embodiments, the mass spectrometric methods comprise C-terminal sequencing. In some embodiments, the mass spectrometric methods comprise Edman degradation. In various embodiments, the derivative sequence is subjected to a separation process prior to identification. In some embodiments, the separation process comprises chromatography. In some embodiments, the separation process comprises HPLC. Suitable separation methods for the separation process comprise, for example, ion-exchange chromatography or hydrophobic interaction chromatography. Ion-exchange chromatography can use any matrix material comprising functional groups that are strongly acidic (typically, sulfonic acid groups, e.g. sodium polystyrene sulfonate or polyAMPS), strongly basic, (quaternary amino groups, for example, trimethylammonium groups, e.g. polyAPTAC), weakly acidic (mostly, carboxylic acid groups), or weakly basic (primary, secondary, and/or ternary amino groups, e.g. polyethylene amine). The separation method can, for example, use sulfonated polystyrene as a matrix, adding the amino acids in acid solution and passing a buffer of steadily increasing pH through the column. Amino acids are be eluted when the pH reaches their respective isoelectric points. Hydrophobic interaction chromatography may be employed through the use of reversed phase chromatography. Many commercially available C8 and C18 silica columns have demonstrated successful separation of peptides in solution through the use of an elution gradient.

In some embodiments, peptide sequences representing ESBs, APSs and the resulting COBs are designed to improve the ease of detection. In some cases, peptide sequences can be designed to improve fragmentation patterns in a mass spectrometer. It is well known in the art that the fragmentation efficiency of a bond in a peptide sequence is sequence dependent (see, e.g. Tabb et al. *Anal Chem.* 2003 Mar. 1; 75(5): 1155 and Klammer et al. *Bioinformatics* 2008, 24: 348-356). The sequence-dependent fragmentation efficiencies can be employed to design representative peptide sequences with desired fragmentation patterns.

In some embodiments, peptide sequences representing ESBs, APSs and the resulting COBs are designed to confer certain physical and chemical characteristics to the peptide molecules. For example, representative peptide sequences can be designed to result in peptide molecules with solubilities in aqueous solutions within a desired range. For another example, representative peptide sequences can be designed to result in peptide molecules with a desired degree of secondary or tertiary structure or lack thereof. For yet another example, representative peptide sequences can be designed to result in peptide molecules with disulfide bonds or lack thereof. For a yet further example, representative peptide sequences can be designed to result in peptide molecules with desired binding characteristics to chosen targets. The sequences of the ESBs, CLs, APSs and the resulting COBs can further be designed to exploit specially loaded tRNAs in a protein expression system. Accordingly, incorporation of non-natural amino acids to the resulting peptide molecules can be accomplished.

Various embodiments relate to separating the ESB-linked COBs or derivative sequences, such as a peptide sequence, prior to detection. In some embodiments, the separation is based on a suitable physiochemical property of the molecules. These types of separations are particularly useful to direct the molecules to the detectors sequentially thereby increasing their relative abundance and the complexity of the signal at the time of the detection. Various embodiments comprise separation of the molecules in a sequence-targeted manner. For example, all molecules comprising a particular ESB can be isolated by hybridizing the ESB sequence to a sufficiently complementary sequence, affinity purifying using an ESB-specific linked tag, affinity purifying using a derivative sequence encoded by the ESB sequence or any other suitable method known in the art. Separation methods may also target a cell-specific COB or a portion thereof.

In some embodiments, constructs comprising ESBs and COBs are subjected to separation. For example, the constructs can be subjected to gradient or affinity purification sorting according to the ESBs. In some embodiments, the separation may comprise multiple dimensions, for example 2, 3, 4, 5, 6, 7, or more dimensions. For example, the constructs can be separated sorting according to the first APSs on one dimensions and sorting the according to the second APSs on another dimension and optionally sorting according to the ESBs on a third dimension.

In some embodiments, the separation method comprises separation by gradient, on a gel, using an electromagnetic field and/or any other suitable separation method known in the art. In some embodiments, constructs comprising ESBs and/or COBs can be separated prior to detection. For example, the constructs can be separated according to ESBs and the ESBs and/or COBs in the constructs can be detected following the separation. The detection can be molar ratio detection, enzymatic detection, sequencing, differential affinity in a gradient or gel, electromagnetic field, e.g. UV, fluorescence or chemiluminescence, any detection method described herein, or any other suitable detection method known in the art. In some embodiments, the separation comprises immobilizing the constructs. For example, the constructs can be immobilized on an array surface or on a bead. A portion of the ESB and/or COB can be used to immobilize the constructs. The ESB and/or the COB can be detected from immobilization positions. In one example, ESBs and/or COBs comprising oligonucleotide can be immobilized on a bead or microarray that is coated with complementary oligonucleotides.

a. Detectable Molecules or Label Monomers

The COBs of the present invention can be labeled with any of a variety of label monomers, such as a radioisotope, fluorochrome, dye, enzyme, nanoparticle, chemiluminescent marker, biotin, or other monomer known in the art that can be detected directly (e.g., by light emission) or indirectly (e.g., by binding of a fluorescently-labeled antibody). Generally, one or more of the labeled APSs in the COB is labeled with one or more label monomers, and the signals provided by the label monomers attached to the APS of a COB constitute a detectable code that identifies the target to which the UBA the COB binds. In certain embodiments, the lack of a given signal from the APS (e.g., a dark spot) can also constitute part of the COB's code.

Example of label monomers that can be used with the COBs described herein and methods to incorporate the labels monomers into the COBs are described in U.S. Pat. No. 7,473,767; U.S. application Ser. Nos. 10/542,458; 12/324,357; 11/645,270 and 12/541,131, incorporated herein by reference in their entirety.

When adding detectable molecules or label monomers to the COBs, in addition to the qualitative analytical capabilities provided by the COB of the invention and the analytical techniques based thereon, the COB of the invention are uniquely suitable for conducting quantitative analyses. By providing a one to one binding between the COB of the invention and their target molecules in a biomolecular sample, all or a representative portion of the target molecules present in the sample can be identified and counted. This individual counting of the various molecular species provides an accurate and direct method for determining the absolute or relative concentration of the target molecule in the biomolecular sample. Moreover, the ability to address each molecule in a mixture individually leverages benefits of miniaturization including high sensitivity, minimal sample quantity requirements, high reaction rates which are afforded by solution phase kinetics in a small volume, and ultimately very low reagent costs.

Target Molecules

Target molecules or epitopes are the molecules detected or measured by binding of a UBA whose target-specific region(s) recognize thereto. Examples of target molecules include, but are not limited to, proteins, nucleic acids, lipids, carbohydrates, small molecules, organic monomers, or drugs. Nucleic acids that can be analyzed by the methods herein include: double-stranded DNA, single-stranded DNA, single-stranded DNA hairpins, DNA/RNA hybrids, RNA (e.g. mRNA or miRNA) and RNA hairpins. For convenience only, the methods described herein are explained mostly in the context of analyzing proteins or mRNA. However, the embodiments described herein also can be used to detect non-protein or non-mRNA targets. In some embodiments, the target molecule is selected from the group consisting of a peptide, a polypeptide, an oligopeptide, a protein, a phosphoprotein, an antibody, a nucleic acid, a peptide nucleic acid, a synthetic small molecule, a disaccharide, a trisaccharide, an oligosaccharide, a polysaccharide, a lipid, a steroid, and a phospholipid.

A target molecule can be part of a biomolecular sample that contains other components or can be the sole or major component of the sample. A target molecule can be a component of a whole cell or tissue, a cell or tissue extract, a fractionated lysate thereof or a substantially purified molecule. The target molecule can be attached in solution or solid-phase, including, for example, to a solid surface such as a chip, microarray or bead. Also the target molecule can have either a known or unknown structure or sequence.

The compositions, methods, and kits disclosed herein can also be used in a wide variety of applications to determine the presence of target molecules in a sample. For example but without limitation, the compositions, methods, and kits are useful for, pharmacokinetic studies, including but not limited to, drug metabolism, ADME profiling, and toxicity studies; target validation for drug discovery; gene expression profiling, protein expression profiling; proteome analyses; metabolomic studies; post-translation modification studies, including but not limited to glycosylation, phosphorylation, acetylation, and amino acid modification, such as modification of glutamate to form gamma-carboxy glutamate and hydroxylation of proline to form hydroxylation; analyses of specific serum or mucosal antibody levels, evaluation of non-nucleic acid diagnostic indicators; foreign antigen detection; and the like.

In certain embodiment, at least one UBA, at least one ESB, or both the UBA and the ESB comprise at least one antibody, aptamer or peptoid that reacts specifically with at least one target molecule. In certain embodiments, at least one LBA, at least ESB, or both the LBA and the ESB comprise binding proteins that specifically interact with at least one target molecule. In some embodiments, the ESB comprise a common linker moiety.

The skilled artisan will appreciate that the molecular complexes and the at least part of the molecular complexes described herein can be individually detected while tethered or attached to a substrate or while in solution, depending on, among other things, the nature of the specific molecular complex or cleavable component and the SMD technique and detection apparatus employed.

Methods

Figure 2:
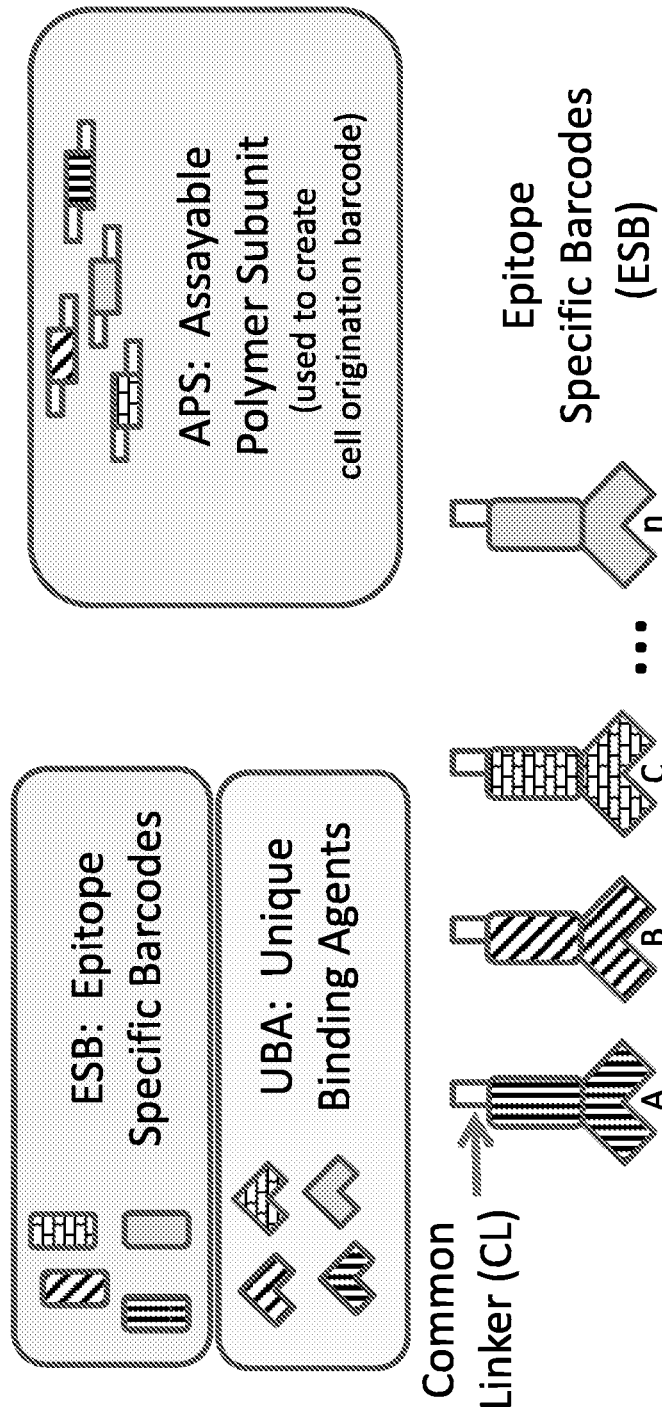
FIG. 2 shows a graphical representation of one embodiment of the components of the epitope specific barcode and cells origin barcodes of the invention and their assembly.
Figure 2:
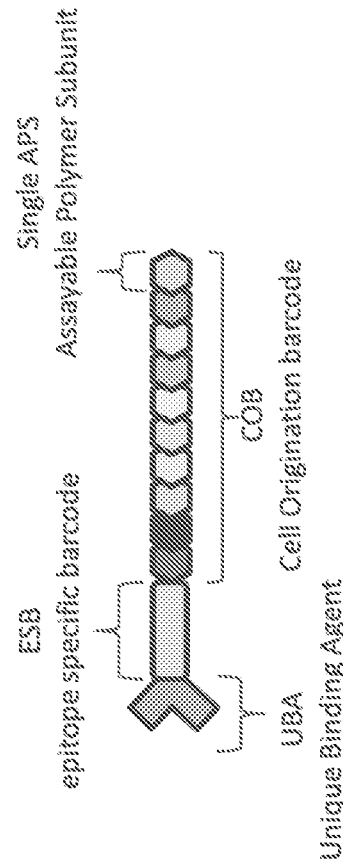

The present invention provides methods for detection and quantification of target molecules in biomolecular samples. In particular, the invention provides UBAs that are capable of binding individual target molecules. The invention also provides the use of ESBs and COBs (See FIG. 2). Through the ESBs' and COBs' codes, the binding of the UBAs to target molecules results in the identification of the target molecules in single cells. In some embodiments, the ESB/COB complex represents a quantum of information that represents the target molecule and the cell of origin (See FIG. 1). Methods of making and using such UBAs and/or ESBs and COBs are also provided.

In one aspect, the invention provides methods to identify, multiple target molecules in every cell of a complex cell population and to retain cell specific information regarding that target molecule. Therefore, for each cell the amount of each target molecule associated with that cell is assayed. In some embodiments, multiple quanta of information are determined to identify multiple target molecules in every cell of a complex cell population.

In some embodiments, the invention provides methods for detecting at least one target molecule in a sample comprising the steps: (a) providing: (i) a population of cells potentially comprising at least one target molecule, (ii) a first UBA specific for a first target molecule, (iii) a first epitope specific barcode ESB specific for a region of the first UBA, where the ESB comprises a first common linker moiety, and (iv) a population of COB, where the population of COB comprises a second common linker moiety, where the second linker moiety is complementary to the first common linker moiety is the first ESB; (b) forming at least a first complex comprising the at least one target molecule, the first UBA probe, and the first ESB, where the at least one target molecule is bound to the first UBA and the ESB is bound to the UBA (c) adding the population of COBs, where a second complex is formed with the least one target molecule, the first UBA probe, the first ESB, and a first COB, and where the second common linker moiety from the first COB is bound to the first linker moiety from the first ESB, and where the COBs from the population of COBs is associated with a cell from the population of cells; and (d) detecting the second complex or at least part of the third complex.

In some embodiments, the invention provides methods for detection and/or quantification of a target molecule by binding a UBA to a target molecule. A UBA comprises at least one reaction portion that allow the UBA to bind to or interact with the target molecule; typically in a sequence-specific, a confirmation-specific manner, or both; for example but not limited to antigen-antibody binding, aptamer-target binding, and the like (See FIGS. 2 and 3).

In some embodiments, UBAs can be part of at least one probe set, comprising at least one first probe and at least one second probe. Thus, in some embodiments the invention provides methods for detection and/or quantification of a target molecule by binding a UBA probe set to a target molecule, where the UBA probe set comprises a first UBA probe and a second UBA probe. The first UBA probe and the second UBA probe comprise at least one reaction portion that allow the probes to bind to or interact with different regions of the target molecule, e.g., in a sequence-specific manner, a confirmation-specific manner, or both. In some embodiments, the UBA probe and/or a second UBA probe contain a capture region as described herein.

In certain embodiments, the UBAs comprise an identity portion or at least part of an identity portion, for example, an ESB, a COB, an ESB and/or a linker oligo. The identity portion allows for the identification of the presence or absence of the UBAs bound to the target molecule in the detection step of the methods described herein. Thus, in some embodiments the invention provides methods for detection and/or quantification of a target molecule by binding the UBA to a target molecule, wherein UBA contains an identity portion (e.g., ESB, a COB, an ESB and/or a linker oligo).

In some embodiments, the target molecule is tagged within cells indirectly with an epitope specific barcode (ESB). Each ESB comprises a unique code that can be associated to a specific target molecule. ESBs are molecules or assemblies that are designed to bind with at least one UBA or part of an UBA; and can, under appropriate conditions, form a molecular complex comprising the ESB, the UBA and the target molecule. ESBs comprise at least one identity identification portion that allow them to bind to or interact with at least one UBA; typically in a sequence-specific, a confirmation-specific manner, or both; for example but not limited to UBA-antibody binding, aptamer-target binding, and the like. In some embodiments, the ESB are attached, directly or indirectly, to the UBA. In other embodiments, the ESBs bind to the UBAs in a cell or sample, e.g., as part of the assay procedure. In certain embodiments, the UBAs and/or ESBs comprise a capture region. In some embodiments, the capture region is used for the isolation of the UBA/ESB and/or immobilization of the UBA/ESB into a surface. The capture region can be an affinity tag, a bead, a slide or an array. In certain embodiments, the ESBs comprise common linker moiety, for example, a linker oligo. In certain embodiments, the common linker oligo is complementary to a common linker oligo in the assayable polymer subunits (APSs) that form the cell origination barcode (COB).

Figure 3:
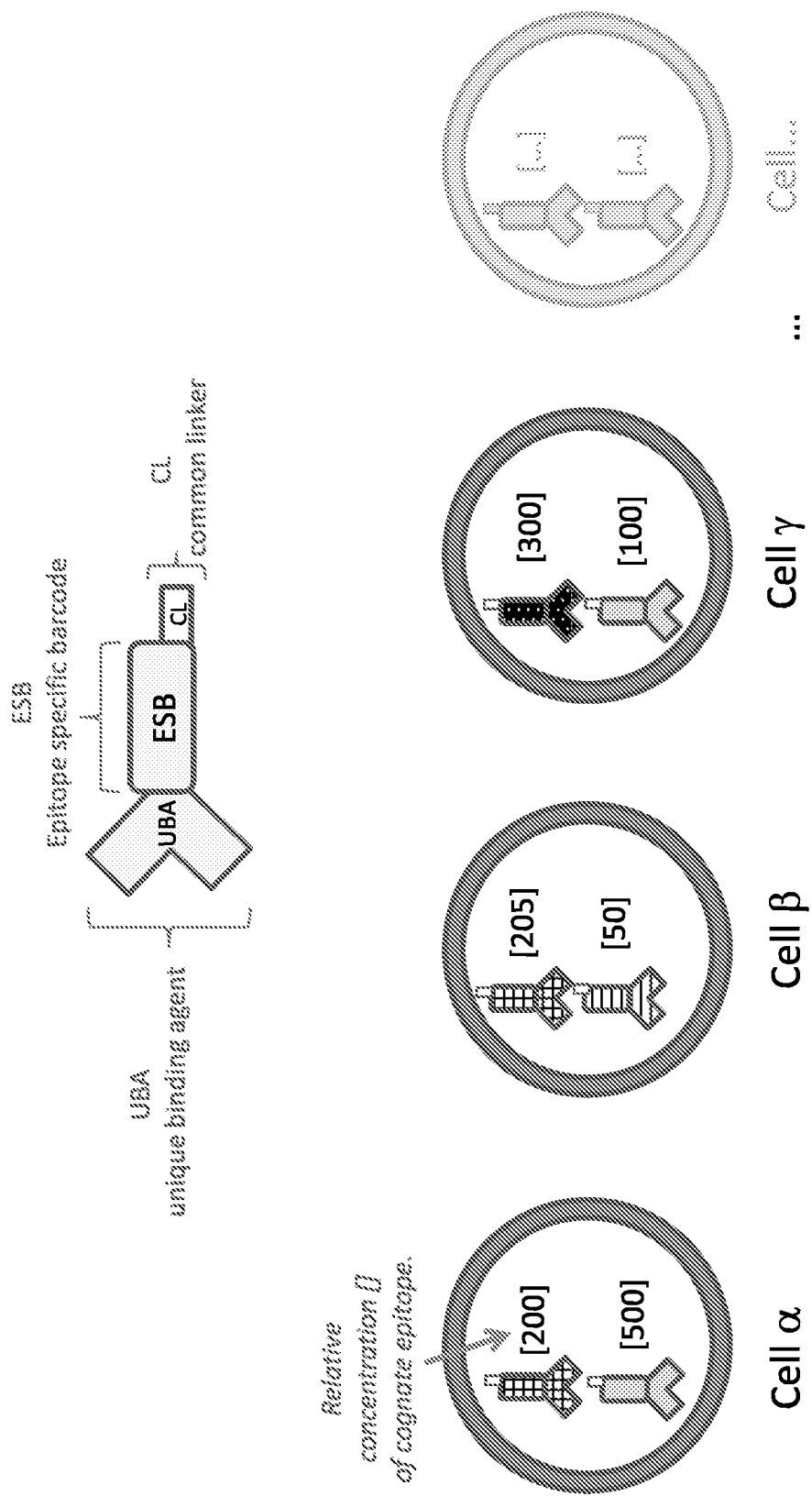
FIG. 3 shows UBA-ESB-CL reagents of one embodiment of the invention.
Figure 4:
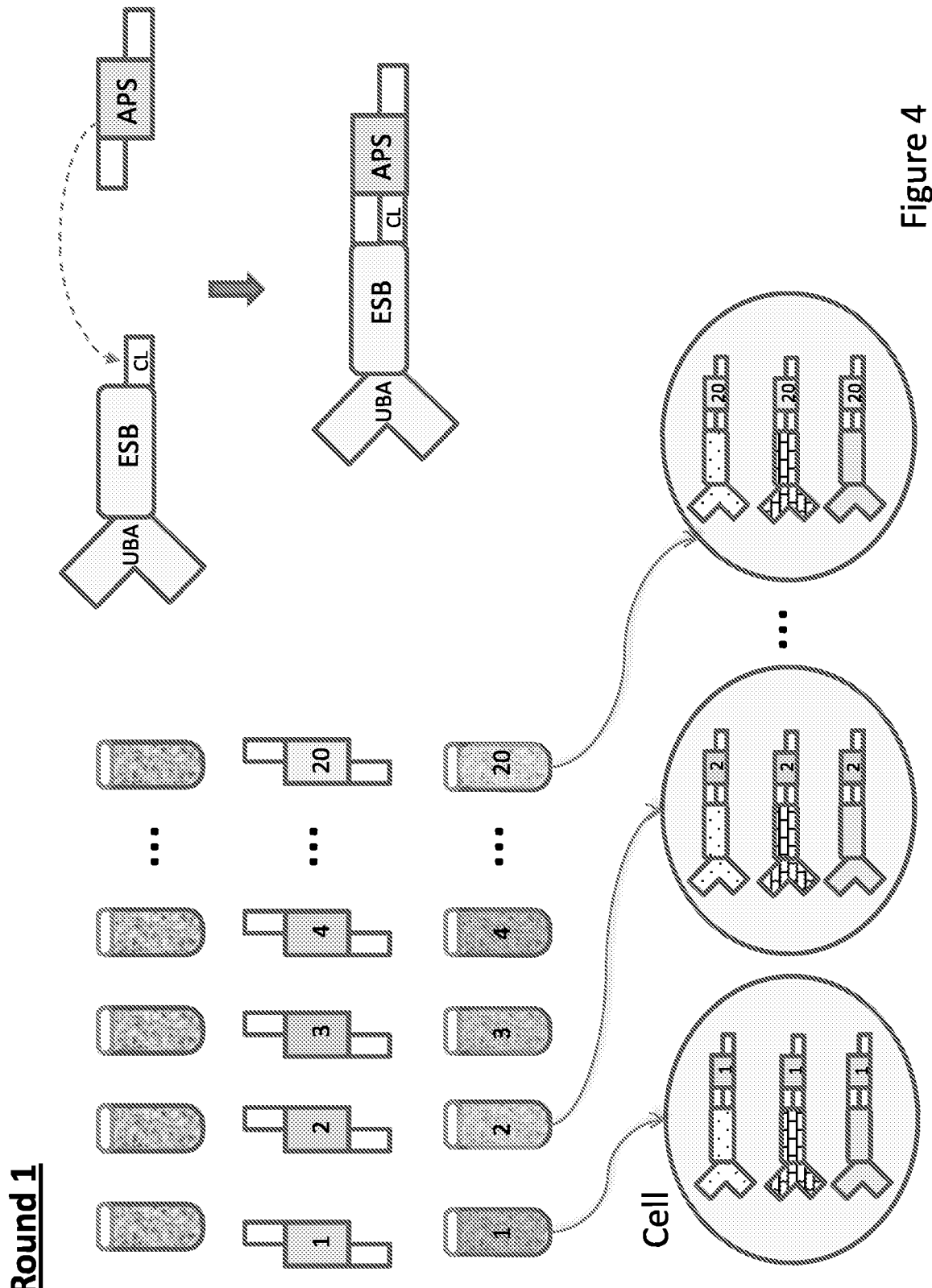
FIG. 4 depicts labeling of cells in one embodiment of the invention with UBA-ESB-CL reagents.
Figure 4:
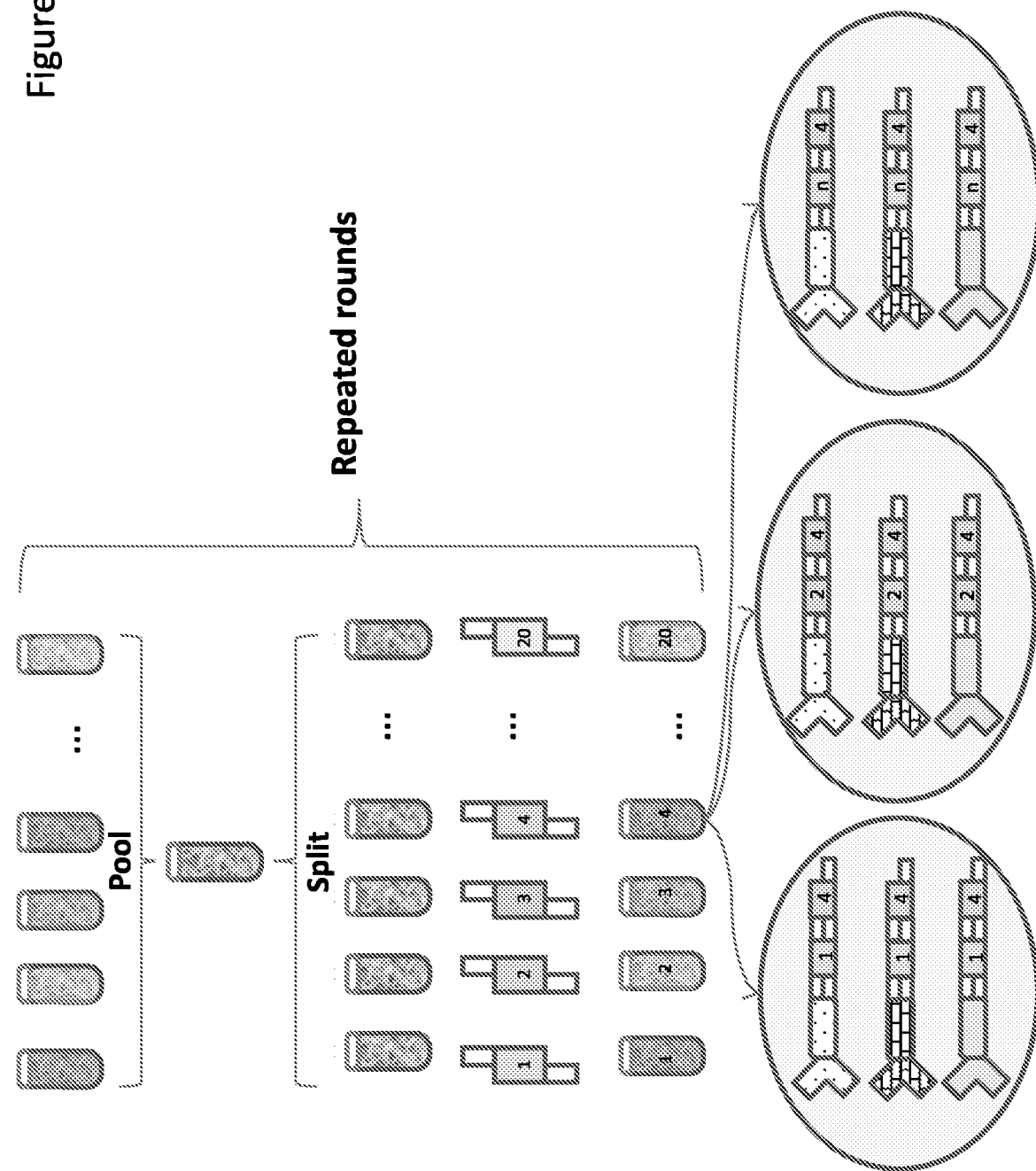

FIGS. 3 and 4 show a schematic representation of one of the embodiments of the invention in which a split pool synthesis approach is used to append the COB to the target molecule/UBA/ESB complex. FIG. 3 in Step 1 shows the labeling of cells with UBA-ESB-CL reagents. The UBA provides the specificity for the target molecule to be recognized in a cell. In some embodiments, the UBA can be an antibody specific for a surface marker like CD8, or an intracellular epitope like a phospho-epitope on a kinase such as Stat-3. In some embodiments, the UBA could be an antisense DNA for a target mRNA in a fixed cell. The UBA is identified with an ESB that has a CL moiety, the latter for later addition of cell specific tagging information. FIG. 4 is Step 2 shows the start of the split pool synthesis. In this example, the cell population is split into 20 tubes. Cell populations can be split into wells, bead or any suitable surfaces known in the art. In Step 3 an APS unit is added to each tube. The APS binds the UBA/ESB complex via the complementary CLs in the APS and the ESB. In Step 4, each cell in a given tube now has appended to each UBA-ESB pair the same subunit as defined by the tube contents (one of 1-20 APS in this example). Each split population from Step 3 now has a DAPS "tag" polymer subunit added to all DBAAs in that cell. In Step 5, the cells from the 20 tubes are pulled into one tube. ½₀ of the cells have the same APS subunit. In Step 6, steps 2-4 are repeated to add a second APS to the prior APS. In this example, cells in one tube will have a mixture of cells all of which have the APS subunit from the round 2 and one of the 20 APSs used in round 1 in a statistically equal distribution. Thus, in round two within each individual tube mixture all polymers are extended by the addition of the same APS. The process is repeated as needed. The epitope/barcode along with linked cell origin signature is read by any methods known in the art including the ones described herein.

The number of split pool rounds required is defined by the number of cells in an assay and a statistical estimate of what would give an over-representation of the number of tags that ensure unique COB for each cell. This is given by the following equation:

Number of tags required is $\ln(1-C)/\ln(1-1/N)$ where
$C$=certainty of over-representation and where
$N$=number of cells Thus, if you have 1 million cells, and you want 99.9% certainty of tag uniqueness, you need:

$$\ln(0.001)/\ln(1-1/10^6)=6,907,751$$

Or approximately 7 million tags. In various embodiments, a high certainty of tag uniqueness ensures a high statistical significance for identification of cells/particles as distinct entities. Without being bound by theory, a high certainty of tag uniqueness provides for a high likelihood that two identical COB labels originated from the same cell/particle.

However, for $10^6$ cells, 7 million tags means 1000 cell pairs could be labeled as the "same" cell. Therefore, to have only a 1 in 10 chance there is a SINGLE pair of duplicate cells, the equation should be set to 99.99999%

$$\ln(1-0.9999999)/\ln(1-1/10^6)=16{,}118{,}087$$

Thus requiring 16-fold more tags than cells.

To determine the number of rounds given a given number of subunits for barcode creation:

$$x^y=T \text{ gives } y=\ln(T)/\ln(x)$$

If you had 20 subunits, for $1.7 \times 10^7$ tags you need the following APS addition cycles:

$$\ln(17{,}000{,}000)/\ln(20)=5.557$$

This can be round up to 6 APS addition cycles.

If you had 100 subunit %, you would need only 3.6 rounds, or round-up to 4 APS addition cycles. Thus, in some embodiments, the invention provides methods for tagging target molecules within cells indirectly with an ESB. The cell population is treated in a split pool synthesis approach that appends to the epitope specific barcode a second signature that indicates the cell of origin, or a cell origin barcode. UBAs can be antibodies, diabodies, etc. for proteins, or anti-sense DNA tags for RNA and DNA for nucleic acids. ESB can be nucleic acids readable by high throughput sequencing approaches or chemical subunits assayable by mass spectrometry approaches. COBs can be nucleic acids readable by high throughput sequencing approaches or chemical subunits assayable by mass spectrometry approaches.

The APS can be specific strands of DNA or DNA-mimics. The APSs can be linked via ligase. Example of enzymes that can be used for ligation include but are not limited to DNA ligase, and RNA ligase such as T4 DNA ligase, T4 RNA ligase, *Thermus thermophilus* (Tth) ligase, *Thermus aquaticus* (Taq) DNA ligase, or *Pyrococcus furiosus* (Pfu) ligase. Chemical ligation can be performed using activating and reducing agents such as carbodiimide, cyanogen bromide (BrCN), imidazole, 1-methylimidazole/carbodiimide/cystamine, N-cyanoimidazole, dithiothreitol (DTf) and ultraviolet light. Also within the scope of the invention are ligation techniques such as gap-filling ligation, including, without limitation, gap-filling OLA and LCR, bridging oligonucleotide ligation, and correction ligation. Descriptions of these techniques can be found, among other places, in U.S. Pat. No. 5,185,243, published European Patent Applications EP 320308 and EP 439182, and PCT Publication Nos. WO 90/01069 and WO 01/57268. The APSs can be extended via polymerases.

These APS subunits can be detected via full sequencing of all DNA tags by any suitable methods known in the art, e.g., Illumina HiSeq 2000, including the sequencing methods described herein.

Figure 5:
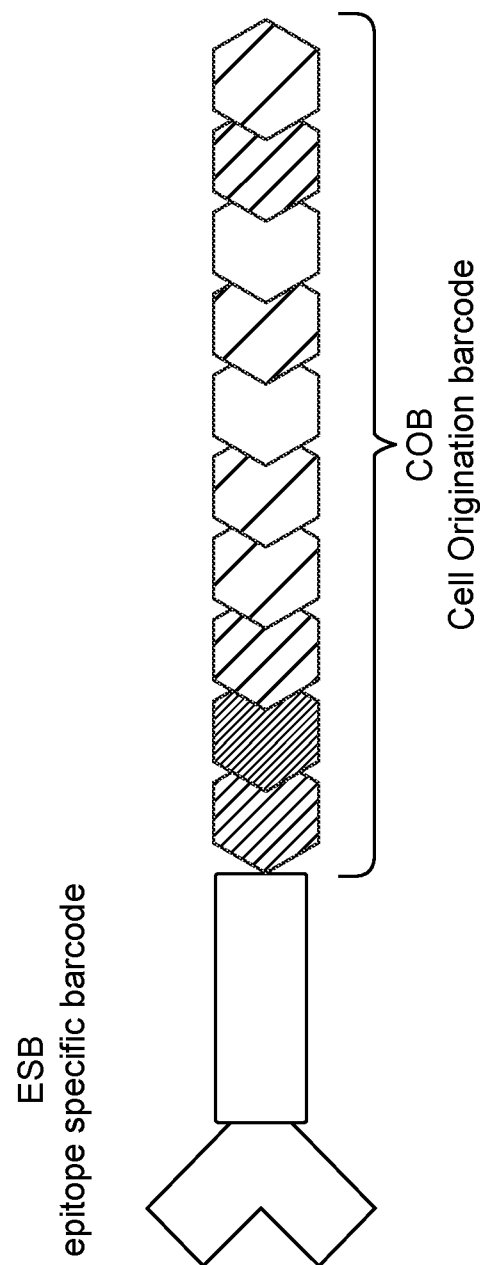
FIG. 5 depicts ESB-COB reagents of one embodiment of the invention.

The APS can be small molecules as per combinatorial synthesis procedures or buildable complex molecules of deterministic weights. These subunits can be detected via mass spectrometry Thus in some embodiments, the cell-specific information is assembled via a UBA (barcode for the epitope to be recognized) as linked to its associated COB (from which cell the information originated) (See FIG. 5).

In some embodiments, the UBA/ESB/COB complexes are isolated via a capture region as described herein. In some embodiments, the capture region is uses for the immobilization of the UBA/ESB/COB complexes into a surface.

In some embodiments, the information on UBAs can be amplified prior to the then COB procedure (split pool) with any suitable amplification technique known in the art, including the ones described herein such branch chain or rolling circle approaches.

In some embodiments, error correction & detection can be encoded into subunits. The general idea for achieving error detection and correction is to add some redundancy (i.e., some extra data) to a message, which receivers can use to check consistency of the delivered message, and to recover data determined to be erroneous. Error-detection and correction schemes can be either systematic or non-systematic: In a systematic scheme, the transmitter sends the original data, and attaches a fixed number of check bits (or parity data), which are derived from the data bits by some deterministic algorithm. If only error detection is required, a receiver can simply apply the same algorithm to the received data bits and compare its output with the received check bits; if the values do not match, an error has occurred at some point during the transmission. In a system that uses a non-systematic code, the original message is transformed into an encoded message that has at least as many bits as the original message. Error detection and correction schemes include repetition codes, parity bits, checksums, cyclic redundancy checks (CRCs), cryptographic hash functions, error-correcting codes, automatic repeat request, Hybrid ARQ, error-correcting code, convolutional codes, block codes such as hamming codes, multidimensional parity-check codes, Reed-Solomon codes, turbo codes and low-density parity-check codes (LDPC).

In some embodiments, the chains at each round are blocked from further addition if polymers did not add. This could be accomplished with DNA as polymer units if each round one uses different overhangs for complementary additions.

In some embodiments, the epitope/barcode along with linked cell origin signature is read by sequencing using methods known in the art, including the ones described herein. The sensitivity for the sequencing approach assuming that each 100 bp read represents an ESB-COB pair is as follows for target proteins. The protein copy numbers of molecules of interest range from 100 to 100,000. Assuming that one will want to read 100 proteins with the following rough distribution:

|  | Test 1 proteins | Test 1 reads | Test 2 proteins | Test 2 reads |
| --- | --- | --- | --- | --- |
| 100 copies | 20 | $2 \times 10^3$ | 20 | $2 \times 10^3$ |
| 500 copies | 20 | $1 \times 10^4$ | 20 | $1 \times 10^4$ |
| 1000 copies | 20 | $2 \times 10^4$ | 20 | $2 \times 10^4$ |
| 10000 copies | 20 | $2 \times 10^5$ | 40 | $4 \times 10^5$ |
| 100000 copies | 20 | $2 \times 10^6$ | 0 | |

In Test 1 one will need to be able to read 2,232,000 sequences per cell then to access all 100 proteins in a cell. Using a sequencing technique that can do $2 \times 10^9$ reads such as Illumina HiSeq 2000, this means the approach can read 100 proteins in ~1000 cells. However, if one limits the high copy number proteins by avoiding them altogether or "capping" their representation by normalization (several approaches can work for this), we can increase the cell number accessible. Say one therefore normalize and cap the 100,000 copies to a 10,000 copy limit (Test 2), then the total number of reads is 432,000. That is one can read 100 proteins in ~5000 cells.

For mRNA the numbers are different, since RNAs are typically expressed much lower. The RNA copy numbers of molecules of interest range from 5 to 1000 (based on Lewin's Essential Genes numbers); not counting specialized mRNAs for high protein production like actin or Ig. Thus, assuming one wants to read 100 mRNAs with the following rough distribution:

|  | Test 1 mRNAs | Test 1 reads |
| --- | --- | --- |
| 5 copies | 60 | 300 |
| 50 copies | 20 | 1000 |
| 100 copies | 10 | 1000 |
| 1000 copies | 10 | 10000 |

In Test 1 one needs to be able to read 12,300 sequences per cell to access all 100 mRNAs in a cell. Using a sequencing technique that can do $2 \times 10^9$ reads such as Illumina HiSeq 2000, this means the approach can read 100 mRNAs in ~162,000 cells. This is equivalent to a high parameter flow cytometry run. 200 mRNAs with the same distribution could scale linearly to be read on ~80,000 cells.

As it will be evident to those skilled in the art increasing the number of reads will increase the cell number and parameters accessible (e.g., mRNAs or proteins).

Any of the embodiments described herein can be used in the detection of multiple target molecules. In some embodiments, the invention provides methods comprising UBA for the analysis of target molecules. In some embodiments, the invention provides a UBA population for use in a multiplexed assay. Each UBA in the population is specific for a target molecule. The binding of the target molecules to the UBAs is then detected using ESB-COB pairs. Each ESB-COB pair comprises a unique label code that can be associated to a specific target molecule and the cell of origin as described herein.

In some embodiments, the detection of the ESB-COB as described below is digital in nature in that one molecule at a time is counted. While fluorescence is used to read the code, the signals are high and the spot is either present of not, thus the digital detection. Using digital detection rather than an analogue fluorescent signal used to quantify signal leads to more accurate quantification. Thus the methods described herein allows for multiplexing to levels beyond currently possible, for more accurate quantification, and possibly higher sensitivity.

Biomolecular Samples

The UBA and ESB/COB systems of the invention can be used to detect target molecules in any biomolecular sample. As will be appreciated by those in the art, the sample may comprise any number of things, including, but not limited to: biological samples, such as cells (including both primary cells and cultured cell lines), cell lysates, or extracts, tissues and tissue extracts; bodily fluids (including, but not limited to, blood, urine, serum, lymph, bile, cerebrospinal fluid, interstitial fluid, aqueous or vitreous humor, colostrum, sputum, amniotic fluid, saliva, anal and vaginal secretions, perspiration and semen, a transudate, an exudate (e.g., fluid obtained from an abscess or any other site of infection or inflammation) or fluid obtained from a joint (e.g., a normal joint or a joint affected by disease such as rheumatoid arthritis, osteoarthritis, gout or septic arthritis) of virtually any organism, with mammalian samples being preferred and human samples being particularly preferred; environmental samples (including, but not limited to, air, agricultural, water and soil samples); biological warfare agent samples; research samples including extracellular fluids, extracellular supernatants from cell cultures, inclusion bodies in bacteria, cellular compartments, cellular periplasm, mitochondria compartment, etc.

The biomolecular samples can be indirectly derived from biological specimens. For example, where the target molecule of interest is a protein kinase the biomolecular sample of the invention can be a sample containing isolated proteins from a cell lysate. In another example, the biomolecular sample of the invention is generated by subjecting a biological specimen to fractionation, e.g., size fractionation or membrane fractionation.

Protein isolation techniques are also well known in the art and kits employing at least some of these techniques are commercially available. Protein isolation techniques typically employ one or more of the following: maceration and cell lysis, including physical, chemical and enzymatic methods; centrifugation; separations by molecular weight, such as size exclusion chromatography and preparative electrophoresis; selective precipitation, for example, salting-in and salting-out procedures; various chromatographic methods; and the like. Detailed descriptions of and relevant protocols for protein purification techniques can be found in, among other places, Marchak et al., Strategies for Protein Purification and Characterization: A Laboratory Course Manual, Cold Spring Harbor Press (1996); Essentials from Cells: A Laboratory Manual, D. Spector and R. Goldman, eds., Cold Spring Harbor Press (2003); R. Simpson, Proteins and Proteomics: A Laboratory Manual, Cold Spring Harbor Press (2003); and D. Liebler, Introduction to Proteomics, Humana Press (2002). Commercially available kits can also be used, for example but not limited to, ProteoExtract™ Partial Proteome Extraction Kits (P-PEK) and ProteoExtract™ Complete Proteome Extraction Kits (C-PEK), available from CALBIOCHEM®, La Jolla, Calif. The skilled artisan will appreciate that non-nucleic acid analytes for use with the inventive compositions, methods, and kits can be readily obtained without undue experimentation using such purification techniques and commercial kits The biomolecular samples of the invention may be either native, e.g., not subject to manipulation or treatment, or treated, which can include any number of treatments, including exposure to candidate agents including drugs, genetic engineering (e.g., the addition or deletion of a gene), etc.

Biomolecular samples may also include environmental samples, such as those containing bacteria or other organisms, such as diatoms, dinoflagellates, algae, among others, such as in certain marine or earth-based samples.

Detection of COBs

COBs/ESB complexes are detected by any means available in the art that is capable of detecting the specific sequences or signals on a given COBs/ESB complex.

In some embodiments, the information on the UBA, ESB, COB, UBA/ESB complexes, UBA/ESB/COB complexes COB/ESB complexes and/or a combination thereof can be amplified. Amplification can be performed by any means known in the art. In some cases, the information on the UBA, ESB, COB, UBA/ESB complexes, UBA/ESB/COB complexes COB/ESB complexes and/or a combination thereof are amplified by polymerase chain reaction (PCR). Examples of PCR techniques that can be used include, but are not limited to, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In any of the embodiments, amplification of the information on the UBA, ESB, COB, UBA/ESB complexes, UBA/ESB/COB complexes COB/ESB complexes and/or a combination thereof may occur on a bead. In any of the embodiments herein, target nucleic acids may be obtained from a single cell.

In any of the embodiments herein, the information on the UBA, ESB, COB, UBA/ESB complexes, UBA/ESB/COB complexes COB/ESB complexes and/or a combination thereof can be pre-amplified prior to the amplification step (e.g., PCR).

In some embodiments the UBA. ESB, COB, UBA/ESB complexes, UBA/ESB/COB complexes COB/ESB complexes and/or a combination thereof are quantified. Methods for quantifying nucleic acids are known in the art and include, but are not limited to, gas chromatography, supercritical fluid chromatography, liquid chromatography (including partition chromatography, adsorption chromatography, ion exchange chromatography, size-exclusion chromatography, thin-layer chromatography, and affinity chromatography), electrophoresis (including capillary electrophoresis, capillary zone electrophoresis, capillary isoelectric focusing, capillary electrochromatography, micellar electrokinetic capillary chromatography, isotachophoresis, transient isotachophoresis and capillary gel electrophoresis), comparative genomic hybridization (CGH), microarrays, bead arrays, and high-throughput genotyping such as with the use of molecular inversion probe (MIP).

Quantification of the UBA, ESB, COB, UBA/ESB complexes, UBA/ESB/COB complexes COB/ESB complexes and/or a combination thereof can be used to determine gene/or allele copy number, gene or exon-level expression, methylation-state analysis, or detect a novel transcript in order to diagnose or condition, i.e. fetal abnormality or cancer.

In some embodiments the UBA, ESB, COB, UBA/ESB complexes, UBA/ESB/COB complexes COB/ESB complexes and/or a combination thereof are sequenced. Sequencing can be accomplished through classic Sanger sequencing methods which are well known in the art. Sequence can also be accomplished using high-throughput systems some of which allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read.

In some embodiments, high-throughput sequencing involves the use of technology available by Illumina's HiSeq 2000 machine. This machine uses reversible terminator-based sequencing by synthesis chemistry. This machine can do 200 billion DNA reads in eight days.

In some embodiments, high-throughput sequencing involves the use of technology available by ABI Solid System. This genetic analysis platform that enables massively parallel sequencing of clonally-amplified DNA fragments linked to beads. The sequencing methodology is based on sequential ligation with dye-labeled oligonucleotides.

In some embodiments, high-throughput sequencing involves the use of technology available by Ion Torrent Personal Genome Machine (PMG). The PGM can do 10 million reads in two hours.

In some embodiments, high-throughput sequencing involves the use of technology available by Helicos BioSciences Corporation (Cambridge. Massachusetts) such as the Single Molecule Sequencing by Synthesis (SMSS) method. SMSS is unique because it allows for sequencing the entire human genome in up to 24 hours. Finally, SMSS is described in part in US Publication Application Nos. 20060024711; 20060024678; 20060012793; 20060012784; and 20050100932.

In some embodiments, high-throughput sequencing involves the use of technology available by 454 Lifesciences, Inc. (Branford, Connecticut) such as the PicoTiterPlate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density pricolitre reactors", Nature, doi:10.1038/nature03959; and well as in US Publication Application Nos. 20020012930; 20030068629; 20030100102; 20030148344; 20040248161; 20050079510, 20050124022; and 20060078909.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13):36.

In some embodiments, high-throughput sequencing can take place using AnyDot.chips (Genovoxx, Germany). In particular, the AnyDot.chips allow for 10×-50× enhancement of nucleotide fluorescence signal detection. AnyDot.chips and methods for using them are described in part in International Publication Application Nos. WO 02088382, WO 03020968, WO 03031947, WO 2005044836, PCT/EP 05/05657, PCT/EP 05/05655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al. Science 24 Mar. 2000; and M. J. Levene, et al. Science 299:682-686, January 2003; as well as US Publication Application No. 20030044781 and 2006/0078937. Overall such system involve sequencing a target nucleic acid molecule having a plurality of bases by the temporal addition of bases via a polymerization reaction that is measured on a molecule of nucleic acid, i.e. the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In some embodiments, sequence analysis of the UBA, ESB, COB, UBA/ESB complexes, UBA/ESB/COB complexes COB/ESB complexes and/or a combination thereof may include a four-color sequencing by ligation scheme (degenerate ligation), which involves hybridizing an anchor primer to one of four positions. Then an enzymatic ligation reaction of the anchor primer to a population of degenerate nonamers that are labeled with fluorescent dyes is performed. At any given cycle, the population of nonamers that is used is structure such that the identity of one of its positions is correlated with the identity of the fluorophore attached to that nonamer. To the extent that the ligase discriminates for complementarity at that queried position, the fluorescent signal allows the inference of the identity of the base. After performing the ligation and four-color imaging, the anchor primer:nonamer complexes are stripped and a new cycle begins. Methods to image sequence information after performing ligation are known in the art.

One or more UBA, ESB, COB, UBA/ESB complexes, UBA/ESB/COB complexes COB/ESB complexes and/or a combination thereof complexes can be detected and/or quantified by any method that detects and/or quantifies the presence of the assembled detection complex of interest. Such methods may include radioimmunoassay (RIA) or enzyme linked immunoabsorbance assay (ELISA), immunohistochemistry, immunofluorescent histochemistry with or without confocal microscopy, Raman spectroscopy, X-ray autoradiography, X-ray radiography, luminescence spectrometry, reversed phase assays, homogeneous enzyme immunoassays, and related non-enzymatic techniques, Western blots, whole cell staining, immunoelectron microscopy, nucleic acid amplification, gene array, protein array, mass spectrometry, patch clamp, 2-dimensional gel electrophoresis, differential display gel electrophoresis, microsphere-based multiplex protein assays, label-free cellular assays and flow cytometry, etc. U.S. Pat. No. 4,568,649 describes ligand detection systems, which employ scintillation counting. These techniques are particularly useful for modified protein parameters. Cell readouts for proteins and other cell determinants can be obtained using fluorescent or otherwise tagged reporter molecules. Microscopy methods are useful for measuring parameters in a morphological context. Flow cytometry methods are useful for measuring intracellular parameters.

When using fluorescent labeled components in the methods and compositions of the present invention, it will recognized that different types of fluorescent monitoring systems, e.g., Cytometric measurement device systems, can be used to practice the invention. In some embodiments, flow cytometric systems are used or systems dedicated to high throughput screening, e.g. 96 well or greater microtiter plates, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B. Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361. Where the COBs/ESB complex is fluorescently labeled, suitable consideration of appropriate excitation sources may be investigated. Possible sources may include but are not limited to arc lamp, xenon lamp, lasers, light emitting diodes or some combination thereof. The appropriate excitation source is used in conjunction with an appropriate optical detection system, for example an inverted fluorescent microscope, an epi-fluorescent microscope or a confocal microscope. Preferably, a microscope is used that can allow for detection with enough spatial resolution to determine the sequence of the spots on the COB/ESB complexes. If for example, the COB/ESB complexes are labeled with three different colors, Alexa 488, Cy3 and Alexa 647 (labeled 1, 2 and 3, respectively). Colors 1, 2 and 3 are each acquired in different channels and the first and second registers, which can be seen as rows of spots, are shifted up by several pixels to be able to show each register individually. Examples of methods for detection of multiple colors that can be used in the methods of the invention are described in U.S. Pat. No. 7,473,767, US patent publication no. 2007/0166708, U.S. application Ser. No. 11/645,270, and PCT application no U.S. Ser. No. 06/049,274, incorporated by reference herein in its entirety.

Fluorescence in a sample can be measured using a fluorimeter. Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci. USA (2000) 18:553-8, each expressly incorporated herein by reference) as well as confocal microscopy.

In some embodiments, a FACS cell sorter (e.g. a FACSVantage™, LSRII, or Canto Cell Sorter, Becton Dickinson Immunocytometry Systems, San Jose, Calif.) is used to sort and collect cells based on the presence or absence of an COB/ESB complex. By imparting an electromagnetic charge to droplets containing the positive cells, the cells can be separated from other cells. The positively selected cells can then be harvested in sterile collection vessels. These cell-sorting procedures are described in detail, for example, in the FACSVantage™. Training Manual, with particular reference to sections 3-11 to 3-28 and 10-1 to 10-17, which is hereby incorporated by reference in its entirety for the above instruments.

In another embodiment, positive cells can be sorted using magnetic separation of cells based on the presence of a COB/ESB complex. In such separation techniques, cells to be positively selected are first contacted with a COB/ESB complex comprising retrievable particles (e.g., magnetically responsive particles). The cell can then be physically separated from non-positive or non-labeled cells, for example, using a magnetic field. When using magnetically responsive particles, the positive or labeled cells can be retained in a container using a magnetic field while the negative cells are removed. These and similar separation procedures are described, for example, in the Baxter Immunotherapy Isolex training manual which is hereby incorporated in its entirety.

In some embodiments, one or more cells are contained in a well of a 96 well plate or other commercially available multi-well plate. In an alternate embodiment, the reaction mixture or cells are in a cytometric measurement device. Other multi-well plates useful in the present invention include, but are not limited to 384 well plates and 1536 well plates. Still other vessels for containing the reaction mixture or cells and useful in the present invention will be apparent to the skilled artisan.

In some embodiments, the abundance of a COB/ESB complex is measured using Inductively Coupled Plasma Mass Spectrometer (ICP-MS). A UBA that has been labeled with a specific element binds to the COB/ESB complex. When the cell is introduced into the ICP, it is atomized and ionized. The elemental composition of the cell, including the COB/ESB complex, is measured. The presence and intensity of the signals corresponding to the labels on the COB/ESB complex indicates the abundance of the COB/ESB complexes on that cell (Tanner et al. Spectrochimica Acta Part B: Atomic Spectroscopy, (2007), 62(3):188-195.).

In some embodiments the 'flow cytometer' is a microfluidic device where the cell measurements, or some of the measurements of the cell's contents, are carried out in channels devised to direct cells past detection devices in parallel sets of multiple channels. See U.S. Pat. Nos. 7,378,280; 7,294,503; 7,294,298; and 6,830,936.

In some embodiments the cells, or some portion of their contents, are sonically encapsulated within individual droplets of liquid and interrogated with detection devices designed to measure each individual droplet's characteristics and the materials within such droplets.

Flexible hardware and software allows instrument adaptability for multiple applications. The software program modules allow creation, modification, and running of methods. The system diagnostic modules allow instrument alignment, correct connections, and motor operations. Customized tools, labware, and liquid, particle, cell and organism transfer patterns allow different applications to be performed. Databases allow method and parameter storage. Robotic and computer interfaces allow communication between instruments.

In some embodiments, the methods of the invention include the use of liquid handling components. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In some embodiments, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In some embodiments, platforms for multi-well plates, multi-tubes, holders, cartridges, minitubes, sonic levitation and encapsulation, deep-well plates, microfuge tubes, cryovials, square well plates, filters, chips, microchannel chips, microfluidics chips, optic fibers, beads, and other solid-phase matrices or platform with various volumes are accommodated on an upgradeable modular platform for additional capacity. This modular platform includes a variable speed orbital shaker, and multi-position work decks for source samples, sample and reagent dilution, assay plates, sample and reagent reservoirs, pipette tips, and an active wash station. In some embodiments, the methods of the invention include the use of a plate reader.

In some embodiments, thermocycler and thermoregulating systems are used for stabilizing the temperature of heat exchangers such as controlled blocks or platforms to provide accurate temperature control of incubating samples from 0° C. to 100° C.

In some embodiments, interchangeable pipet heads (single or multi-channel) with single or multiple magnetic probes, affinity probes, or pipettors robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In some embodiments, useful detectors include a microscope(s) with multiple channels of fluorescence; plate readers to provide fluorescent, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; and a computer workstation.

In some embodiments, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

Applications for Target Molecule Detection

The compositions and methods of the invention can be used for diagnostic, prognostic, therapeutic, patient stratification, drug development, treatment selection, and screening purposes. The present invention provides the advantage that many different target molecules can be analyzed at one time from a single biomolecular sample using the methods of the invention. This allows, for example, for several diagnostic tests to be performed on one sample.

The composition and methods of the invention can be used in proteomics. The methods described herein will typically provide an answer rapidly which is very desirable for this application. The methods and composition described herein can be used in the process of finding biomarkers that may be used for diagnostics or prognostics and as indicators of health and disease. The methods and composition described herein can be used to screen for drugs, e.g., drug development, selection of treatment, determination of treatment efficacy and/or identify targets for pharmaceutical development. The ability to test protein expression on screening assays involving drugs is very important because proteins are the final gene product in the body. In some embodiments, the methods and compositions described herein will measure both protein and gene expression simultaneously which will provide the most information regarding the particular screening being performed.

The composition and methods of the invention can be used in gene expression analysis. The methods described herein discriminate between nucleotide sequences. The difference between the target nucleotide sequences can be, for example, a single nucleic acid base difference, a nucleic acid deletion, a nucleic acid insertion, or rearrangement. Such sequence differences involving more than one base can also be detected. In some embodiments, the UBAs, e.g., oligonucleotide probe, have substantially the same length so that they hybridize to target nucleotide sequences at substantially similar hybridization conditions. As a result, the process of the present invention is able to detect infectious diseases, genetic diseases, and cancer. It is also useful in environmental monitoring, forensics, and food science. Examples of genetic analyses that can be performed on nucleic acids include e-g., SNP detection, STR detection. RNA expression analysis, promoter methylation, gene expression, virus detection, viral subtyping and drug resistance.

The present methods can be applied to the analysis of biomolecular samples obtained or derived from a patient so as to determine whether a diseased cell type is present in the sample, the stage of the disease, the prognosis for the patient, the ability to the patient to respond to a particular treatment, or the best treatment for the patient. The present methods can also be applied to identify biomarkers for a particular disease.

In some embodiments, the methods described herein are used in the diagnosis of a condition. As used herein the term "diagnose" or "diagnosis" of a condition includes predicting or diagnosing the condition, determining predisposition to the condition, monitoring treatment of the condition, diagnosing a therapeutic response of the disease, and prognosis of the condition, condition progression, and response to particular treatment of the condition. For example, a blood sample can be assayed according to any of the methods described herein to determine the presence and/or quantity of markers of a disease or malignant cell type in the sample, thereby diagnosing or staging the a disease or a cancer.

In some embodiments, the methods and composition described herein are used for the diagnosis and prognosis of a condition.

Numerous immunologic, proliferative and malignant diseases and disorders are especially amenable to the methods described herein. Immunologic diseases and disorders include allergic diseases and disorders, disorders of immune function, and autoimmune diseases and conditions. Allergic diseases and disorders include but are not limited to allergic rhinitis, allergic conjunctivitis, allergic asthma, atopic eczema, atopic dermatitis, and food allergy. Immunodeficiencies include but are not limited to severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects. Autoimmune and immune dysregulation disorders include but are not limited to rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia areata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens.

Proliferative diseases and disorders that may be evaluated by the methods of the invention include, but are not limited to, hemangiomatosis in newborns; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

Malignant diseases and disorders that may be evaluated by the methods of the invention include both hematologic malignancies and solid tumors.

Hematologic malignancies are especially amenable to the methods of the invention when the sample is a blood sample, because such malignancies involve changes in blood-borne cells. Such malignancies include non-Hodgkin's lymphoma, Hodgkin's lymphoma, non-B cell lymphomas, and other lymphomas, acute or chronic leukemias, polycythemias, thrombocythemias, multiple myeloma, myelodysplastic disorders, myeloproliferative disorders, myelofibroses, atypical immune lymphoproliferations and plasma cell disorders.

Plasma cell disorders that may be evaluated by the methods of the invention include multiple myeloma, amyloidosis and Waldenstrom's macroglobulinemia.

Example of solid tumors include, but are not limited to, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

The methods described herein can be used to diagnose pathogen infections, for example infections by intracellular bacteria and viruses, by determining the presence and/or quantity of markers of bacterium or virus, respectively, in the sample.

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli. Salmonella, Shigella, Klebsiella, Pseudomonas, Listeria monocytogenes, Mycobacterium tuberculosis, Mycobacterium aviumintracellulare, Yersinia, Francisella, Pasteurella, Brucella,* Clostridia, *Bordetella pertussis, Bacteroides, Staphylococcus aureus, Streptococcus pneumonia,* B-Hemolytic strep, Corynebacteria, *Legionella, Mycoplasma, Ureaplasma, Chlamydia, Neisseria* gonorrhea, *Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia,* and Acitnomycetes.

Fungal infectious agents which can be detected by the present invention include *Cryptococcus neoformans, Blastomyces dermatitidis, Histoplasma capsulatum, Coccidioides immitis, Paracoccidioides brasiliensis, Candida albicans, Aspergillus fumigautus,* Phycomycetes (*Rhizopus*), *Sporothrix schenckii,* Chromomycosis, and Maduromycosis.

Viral infectious agents which can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis,* trematodes, *Diphyllobothrium latum, Taenia* spp., *Pneumocystis carinii,* and *Necator americanis.*

The present invention is also useful for detection of drug resistance by infectious agents. For example, vancomycin-resistant *Enterococcus faecium,* methicillin-resistant *Staphylococcus aureus,* penicillin-resistant *Streptococcus pneumoniae,* multi-drug resistant *Mycobacterium tuberculosis,* and AZT-resistant human immunodeficiency virus can all be identified with the present invention Thus, the target molecules detected using the compositions and methods of the invention can be either patient markers (such as a cancer marker) or markers of infection with a foreign agent, such as bacterial or viral markers.

Because of the quantitative nature of UBA/ESB/COBs, the compositions and methods of the invention can be used to quantify target molecule whose abundance is indicative of a biological state or disease condition, for example, blood markers that are upregulated or downregulated as a result of a disease state.

In some embodiments, the methods and compositions of the present invention can be used for cytokine detection. The low sensitivity of the methods described herein would be helpful for early detection of cytokines, e.g., as biomarkers of a condition, diagnosis or prognosis of a disease such as cancer, and the identification of subclinical conditions.

Kits

The invention further provides kits comprising one or more components of the invention. The kits can comprise, for example, one or more UBAs, one or more ESBs, and/or one or more APSs. The kits can be used for any purpose apparent to those of skill in the art, including those described above.

In certain embodiments, the present invention also provides kits useful for the extension and selective immobilization of COBs, UBAs. ESBs and/or a combination thereof. The kits can comprise a substrate for immobilization and one or more binding partners to facilitate extension or immobilization of a COB, UBA, ESB and/or a combination thereof. The binding partners could, in certain embodiments, comprise a moiety useful for extension of the COB, UBA, ESB and/or a combination thereof, in an appropriate force. In certain embodiments, the binding partners could facilitate immobilization or selective immobilization of the COB, UBA, ESB and/or a combination thereof, to the surface. In further embodiments, the kits could comprise a device capable of extending the COB, UBA, ESB and/or a combination thereof.

The kits can contain a population of COBs, APSs, UBAs. ESBs and/or a combination thereof as described herein.

The kits can contain pre-labeled APSs, or unlabeled APSs with one or more components for labeling the APSs. Moreover, the ESBs and/or APSs provided in a kit may or may not have UBAs pre-attached. In one embodiment, the UBAs are provided in the kit unattached to the ESBs and/or APSs.

The kits can comprise other reagents such as linker oligos and bridging oligos. In some embodiments, the kits can separate the UBAs into different premixes.

The kits can include other reagents as well, for example, buffers for performing hybridization reactions, linkers, restriction endonucleases, and DNA I ligases.

The kits also will include instructions for using the components of the kit, and/or for making and/or using the APSs, COBs, UBAs, and/or ESBs.

EXAMPLES

Prophetic Example 1—Oligonucleotide Preparation

Oligonucleotides can be synthesized according to standard techniques known in the art. For instance, oligonucleotides can be synthesized on a 394A DNA Synthesizer (Applied Biosystems Division of Perkin-Elmer Corp., Foster City, Calif.).

The oligonucleotides are purified by ethanol precipitation after overnight deprotection at 55° C. The primer-specific portions of the oligonucleotides used for PCR amplification are purified by polyacrylamide gel electrophoresis on 10% acrylamide/7M urea gels.

Oligonucleotides are visualized after electrophoresis by UV shadowing against a lightening screen and excised from the gel (Applied Biosystems Inc., 1992). They are then eluted overnight at 64° C. in TNE (i.e. Tris-sodium EDTA) buffer (100 mM Tris/HCl pH 8.0 containing 500 mM NaCl and 5 mM EDTA) and recovered from the eluate using Sep Pak cartridges (Millipore Corp, Milford, Mass.) following the manufacturer's instructions.

Oligonucleotides are resuspended in 100 µl TE (i.e. 10 mM Tri-HCl pH 8.0 containing 1 mM EDTA). Typical concentrations of these original oligonucleotide solutions are about 1 µg/µl or approximately 74 pm/µl.

As a prerequisite for ligation reactions, the oligonucleotides are phosphorylated with T4 polynucleotide kinase at the 5'-end. Aliquots of the oligonucleotides equivalent to 200 pm are combined with 10 µl of 10× kinase buffer (500 mM Tris/HCl pH 8.0, 100 mM MgCl$_2$), 10 µl of 10 mM ATP, 20 U T4 kinase, and sufficient water-ME to give a final volume of 100 µl. Phosphorylation is carried out at 37° C. for 30 min followed by incubation for 10 min at 85° C. to inactivate the T4 enzyme.

The solutions of the oligonucleotides are adjusted to convenient concentrations. The kinased oligonucleotide solution is diluted fourfold in water to yield a concentration of 1000 fm/µl. A solution of the oligonucleotides is made by combining volumes of the oligonucleotides equivalent to 200 pm with sufficient water to give a final volume of 400 µl. This created a solution 1000 fm/µl in each of the oligonucleotides. Aliquots (20 µl) of the kinased and unkinased oligonucleotides are frozen for subsequent use.

General Method for Oligonucleotide Synthesis and Purification for Click Chemistry Oligonucleotides are synthesized as described in El-Sagheer et al. (PNAS, 108:28, 11338-11343, 2011). Briefly, standard DNA phosphoramidites, solid supports and additional reagents are purchased from Link Technologies and Applied Biosystems. Oligonucleotides are synthesized on an Applied Biosystems 394 automated DNA/RNA synthesizer using a standard 0.2 or 1.0 µmole phosphoramidite cycle of acid-catalyzed detritylation, coupling, capping, and iodine oxidation. All β-cyanoethyl phosphoramidite monomers are dissolved in anhydrous acetonitrile to a concentration of 0.1 M immediately prior to use. The coupling time for normal A, G, C, and T monomers is 35 see, whereas the coupling time for the reverse amidites is 180 sec. Alkyne phosphoramidite monomer (2c in FIG. 2, El-Sagheer et al., PNAS, 108:28, 11338-11343, 2011) and other non-standard monomers are coupled for 360 sec. Cleavage of oligonucleotides from the solid support and deprotection is achieved by exposure to concentrated aqueous ammonia solution for 60 min at room temperature followed by heating in a sealed tube for 5 hr at 55° C. The oligonucleotides are purified by reversed-phase HPLC on a Gilson system using an XBridge™ BEH300 Prep C18 10 IM 10×250 mm column (Waters) with a gradient of acetonitrile in ammonium acetate (0% to 50% buffer B over 30 min, flow rate 4 mL/min), buffer A: 0.1 M ammonium acetate, pH 7.0, buffer B: 0.1 M ammonium acetate, pH 7.0, with 50% acetonitrile. Elution is monitored by UV absorption at 305 or 295 nm. After HPLC purification, oligonucleotides are desalted using NAP-10 columns and analyzed by gel electrophoresis.

i) Synthesis of 3'-Alkyne Oligonucleotides

Synthesis of 3'-alkyne oligonucleotides is performed as described in El-Sagheer et al. (PNAS, 108:28, 11338-11343, 2011). Briefly, 3'-Alkyne oligonucleotides are synthesized using the 3'-propargylthymidine phosphoramidite monomer 2c and assembling the required sequence in the 5' to 3'-direction using the 3'-O-(4,4'-dimethoxytrityl)deoxyribonucleoside-5'-phosphor-amidites of A, G, C and T (reverse phosphoramidites, Link Technologies) or by the attachment of 5'-O-(4,4'-dimethoxytrityl)-3'-O-propargyl-5-methyl-deoxycytidine to solid support (33 µmol/g loading, AM polystyrene, Applied Biosystems) according to El-Sagheer et al. (Proc. Natl. Acad. Sci. U.S.A. 107(35):15329-15334.). The resin is packed into a twist column (Glen Research), then used to assemble the required sequence in the 3'- to 5'-direction by standard phosphoramidite oligonucleotide synthesis. The oligonucleotides are then cleaved, deprotected and purified as described above.

ii) Synthesis of 5'-Azide Oligonucleotides

Synthesis of 5'-azide oligonucleotides is performed as described in El-Sagheer et al. (PNAS, 108:28, 11338-11343, 2011). Briefly, oligonucleotides are assembled on the 0.2 or 1.0 µmol scale (trityl-off) as described in the general method (above) with normal 5'-HO-dC, 5'-HO-dT (or with 5'-iodo-dT using the commercially available 5'-iodo dT monomer from Glen Research). To convert the 5'-hydroxyl group to 5'-iodo, the protected oligomers attached to the synthesis column are treated with a 0.5 M solution of methyltriphenoxyphosphonium iodide in DMF (1.0 mL), which is periodically passed through the column via two 1 mL syringes over 15 min at room temperature. The column is then washed several times with dry DMF. To convert the 5'-iodo (dT or dC) to 5'-azido (dT or dC), sodium azide (50 mg) is suspended in dry DMF (I mL), heated for 10 min at 70° C. then cooled down and the supernatant taken up into a 1 mL syringe, passed back and forth through the column then left at room temperature overnight (or for 5 hr at 55° C.). The column is then washed with DMF and acetonitrile and dried by the passage of a stream of argon gas. The resultant 5'-azide oligonucleotide is cleaved from the solid support, deprotected and purified as described above.

iii) Synthesis of 3'-Alkyne-5'-Azide Oligonucleotides

Synthesis of 3'-alkyne-5'azide oligonucleotides is performed as described in El-Sagheer et al. (PNAS, 108:28, 11338-11343, 2011). Briefly, 5'-O-(4,4'-Dimethoxytrityl)-3'-O-propargyl-5-methyldeoxycytidine on polystyrene solid support is packed into a twist column (Glen Research) and used to assemble the required sequence in the 3'- to 5'-direction (standard phosphoramidite oligonucleotide synthesis) with 5'-iodo dT, 5'-HO-dT or 5'-HO-dC at the 5'-end. The 5'-hydroxyl or iodo groups are then converted to azide using the conditions described above for the synthesis of the 5'-azide oligonucleotides.

Prophetic Example 2. Click Chemistry Ligation

Oligonucleotide APSs are annealed to a template and kept overnight at 4° C. A solution of Cu$^I$ click catalyst is prepared from tris-hydroxypropyltriazole ligand as described in Chan et al. (Chan T R, Hilgraf R, Sharpless K B, & Fokin V V (2004) Polytriazoles as copper(I)-stabilizing ligands in catalysis. Org. Lett. 6(17):2853-2855; 2.8 µmol in 0.2 M NaCl, 38.0 µL), sodium ascorbate (4.0 µmol in 0.2 M NaCl, 8.0 µL) and CuSO4·5H2O (0.4 µmol in 0.2 M NaCl, 4.0 µL). This solution is added to the annealed oligonucleotides and the reaction mixture is kept at 0° C. for 1 hr, then at room temperature for a further 1 hr. Reagents are removed using a NAP-25 gel-filtration column.

Prophetic Example 3. Split-Pool Synthesis of COBs on Beads

In this Example COBs are synthesized attached to beads. 4 different methods are used for the assembly of APSs into COBs:

Patchwork COB (FIG. 6)

Aminomethyl macroporous polystyrene (MPPS) beads are labeled with ten different CL oligonucleotides, each with an optional first amplification primer complementary region, one of 10 different ESB sequences and a common annealing region. Six rounds of split pool synthesis are performed. In each round, beads are split into 20 different containers. A different oligonucleotide APS is added to each container, totaling 20 different APSs. Each APS in a given round further comprises a unique subcode sequence that is different from the rest of the APSs in that round.

In the first round, each APS comprises an annealing region 1 that is complementary to the annealing region of the CL oligonucleotide on one end and an annealing region 2 on the other end. Upon addition, the oligonucleotide APS hybridizes to the CL oligonucleotide along the complementary annealing region 1. The annealing region 2 remains single stranded and available to hybridization with an APS added in the subsequent round. In subsequent rounds, each APS comprises an annealing region complementary to the available annealing region of the APS from the previous round on one end and an additional annealing region on the other end. The added APS hybridizes to the APS added in the previous round along the complementary annealing region.

The last subunit optionally comprises a second amplification primer complimentary region for hybridization of PCR or sequencing primers.

A CL, or one or more APSs further comprise a random tag region, which acts as a molecular counter as described supra, allowing for subsequent normalization of the detected COBs.

Upon the addition of an APS in each round, the beads are pooled and divided into new 20 pools initiating the subsequent round. A new set of 20 APSs are added in each round with a pair of round specific annealing region as described above. After the addition of 6 APSs, the hybridized APSs on the beads are patched together using a polymerase/ligase. The COBs are optionally PCR amplified for sequencing using primers targeting the amplification primer complementary regions on the CL and the last APS subunit Stitch COB Using Specific Annealing of Primers (FIG. 7)

Aminomethyl macroporous polystyrene (MPPS) beads are labeled with ten different CL oligonucleotides, each with an optional first amplification primer complementary region, a one of 10 different ESB sequences and a common annealing region. Six rounds of split pool synthesis are performed. In each round, beads are split into 20 different containers. A different oligonucleotide APS is added to each container, totaling 20 different APSs. Each APS in a given round further comprises a unique subcode sequence that is different from the rest of the APSs in that round.

An annealing primer is also added. In the first round, the annealing primer has a complementary region to the CL oligonucleotide and a complementary region to the APS. The annealing primer hybridizes to both, stitching them together. In subsequent rounds, the annealing primer has a complementary region to the APS added during the previous round and a complementary region to the APS being added in the current round. Similarly, the annealing primer hybridizes to APSs from subsequent rounds stitching them together. The complementary regions of the annealing primer are specific to each round allowing efficient hybridization of subunits only from the previous and current rounds. Accordingly, the annealing primer does not hybridize to subunits of earlier rounds, which would not have complementary regions to the annealing primer of a current round, thus blocking the further synthesis of COBs missing subunits of particular rounds.

The last subunit optionally comprises a second amplification primer complimentary region for hybridization of PCR or sequencing primers.

A CL, or one or more APSs further comprise a random tag region, which acts as a molecular counter as described supra, allowing for subsequent normalization of the detected COBs.

Upon the addition of an APS and an annealing primer in each round, the beads are pooled and divided into new 20 pools initiating the subsequent round. A new set of 20 APSs are added in each round with a pair of round specific annealing region as described above. After the addition of 6 APSs, the hybridized APSs on the beads are permanently stitched together using a polymerase/ligase or using Click chemistry as described in Example 2. The COBs are optionally PCR amplified for sequencing using primers targeting the amplification primer complementary regions on the CL and the last APS subunit.

Stitch COB Using Annealing of Primers with Common Complementary Regions (FIG. 8)

Aminomethyl macroporous polystyrene (MPPS) beads are labeled with ten different CL oligonucleotides, each with an optional first amplification primer complementary region, a one of 10 different ESB sequences and a common annealing region. Six rounds of split pool synthesis are performed. In each round, beads are split into 20 different containers. A different oligonucleotide APS is added to each container, totaling 20 different APSs. Each APS in a given round further comprises a unique subcode sequence that is different from the rest of the APSs in that round.

An annealing primer is also added. In the first round, the annealing primer has a first complementary region to the CL oligonucleotide and a second complementary region to the APS being added in the current round. The annealing primer hybridizes to both, stitching them together. In subsequent rounds, the annealing primer has a first complementary region to the APS added during the previous round and a second complementary region to the APS being added in the current round. Similarly, the annealing primer hybridizes to APSs from subsequent rounds stitching them together. Of the two complementary regions of the annealing primer, the first complementary regions are specific to each round allowing efficient hybridization to subunits only from the previous round. Accordingly, the annealing primer does not hybridize to subunits of earlier rounds, which would not have complementary regions to the annealing primer of a current round, thus blocking the further synthesis of COBs missing subunits of particular rounds.

The last subunit optionally comprises a second amplification primer complimentary region for hybridization of PCR or sequencing primers.

A CL, or one or more APSs further comprise a random tag region, which acts as a molecular counter as described supra, allowing for subsequent normalization of the detected COBs.

Upon the addition of an APS and an annealing primer in each round, the beads are pooled and divided into new 20 pools initiating the subsequent round. A new set of 20 APSs are added in each round with a pair of round specific annealing region as described above. After the addition of 6 APSs, the hybridized APSs on the beads are permanently stitched together using a polymerase/ligase or using Click chemistry as described in Example 2. The COBs are optionally PCR amplified for sequencing using primers targeting the amplification primer complementary regions on the CL and the last APS subunit.

Loop COB (FIG. 9)

Aminomethyl macroporous polystyrene (MPPS) beads are labeled with ten different CL oligonucleotides, each with an optional first amplification primer complementary region, one of 10 different ESB sequences, six pairs of APS-specific loop annealing regions and an optional second amplification primer complementary region. Six rounds of split pool synthesis are performed. In each round, beads are split into 20 different containers. A different oligonucleotide APS is added to each container, totaling 20 different APSs. Each APS in a given round further comprises a unique subcode sequence that is different from the rest of the APSs in that round.

The APSs are designed to hybridize to the CL in a loop geometry, hybridizing on each end to the CL along the loop annealing regions specific to the round. The hybridization populates the APSs along the CL, which are then linked together. The APSs are designed such that they do not efficiently hybridize to the CL along the loop annealing regions specific to other rounds. Consequently, if an APS from a particular round is missing, the APSs may not be linked together successfully, depending on the linking process. Alternatively, a COB is synthesized with a missing APS, the location of which is flanked by a pair of loop annealing regions. The resulting COB can then be analyzed accordingly and can either be discarded or the retrieved information can be alternatively processed.

A CL, or one or more APSs further comprise a random tag region, which acts as a molecular counter as described supra, allowing for subsequent normalization of the detected COBs.

Upon the addition of an APS and an annealing primer in each round, the beads are pooled and divided into new 20 pools initiating the subsequent round. A new set of 20 APSs are added in each round with a pair of round specific annealing region as described above. After the addition of 6 APSs, the hybridized APSs on the beads are permanently stitched together using a polymerase/ligase or using Click chemistry as described in Example 1. The COBs are optionally PCR amplified for sequencing using primers targeting the amplification primer complementary regions on the CL.

Polymerase Free COB-ESB Linkage (FIG. 10)

Aminomethyl macroporous polystyrene (MPPS) beads are labeled with ten different CL oligonucleotides, each with a pair of loop annealing region specific for one of the 10 different loop ESB sequences, and six pairs of APS-specific loop annealing regions. All 10 loop ESB sequences are added to anneal to the loop ESB specific portion of the CL in a loop geometry. Loop ESB sequences are designed to minimize non-specific annealing to the remainder of the loop ESB specific regions of the CLs. Loop ESB sequences comprise an optional first amplification primer complementary region, an ESB sequence, and a pair of annealing regions sufficiently complementary to the loop ESB-specific loop annealing regions in the CL. Six rounds of split pool synthesis are performed. In each round, beads are split into 20 different containers. A different oligonucleotide APS is added to each container, totaling 20 different APSs. Each APS in a given round further comprises a unique subcode sequence that is different from the rest of the APSs in that round. The APSs in the final round optionally further comprise a second amplification primer complementary region.

The APSs are designed to hybridize to the CL in a loop geometry, hybridizing on each end to the CL along the loop annealing regions specific to the round. The hybridization populates the APSs along the CL, which are then linked together. The APSs are designed such that they do not efficiently hybridize to the CL along the loop annealing regions specific to other rounds. Consequently, if an APS from a particular round is missing, the APSs may not be linked together successfully, depending on the linking process. Alternatively, a COB is synthesized with a missing APS, the location of which is flanked by a pair of loop annealing regions. The resulting COB can then be analyzed accordingly and can either be discarded or the retrieved information can be alternatively processed.

A CL, or one or more APSs further comprise a random tag region, which acts as a molecular counter as described supra, allowing for subsequent normalization of the detected COBs.

Upon the addition of an APS and an annealing primer in each round, the beads are pooled and divided into new 20 pools initiating the subsequent round. A new set of 20 APSs are added in each round with a pair of round specific annealing region as described above. After the addition of 6 APSs, the hybridized APSs on the beads are permanently stitched together using a using Click chemistry as described in Example 2. The COBs are optionally PCR amplified for sequencing using primers targeting the amplification primer complementary regions on the CL and the last APS subunit.

Prophetic Example 4. Detection by Nucleic Acid Sequencing

The assembled ESB-linked COBs resulting from any of the methods in Example 3 are sequenced by Illumina's HiSeq 2000 machine. The resulting sequences comprise at least one of 10 different ESB sequences, a random tag region, and a combination of 6 subcodes originating from APSs added to that particular bead during the 6 rounds of split pool synthesis.

Figure 11:
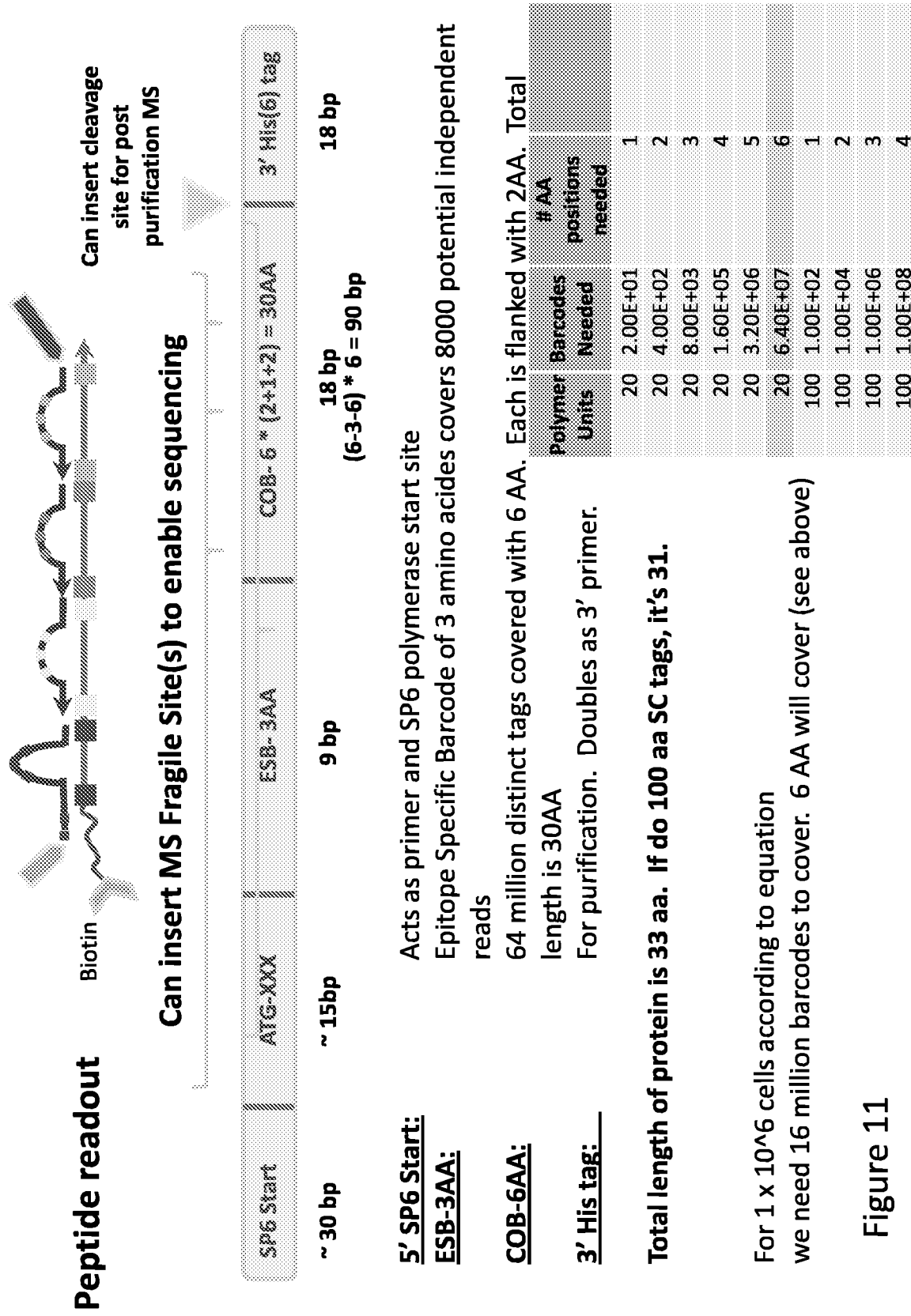
FIG. 11 depicts a peptide based ESB-COB readout according to one embodiment of the invention.

Prophetic Example 5. Detection by Peptide Sequencing (FIG. 11)

ESB-linked COBs are synthesized using any of the methods in Example 3. The resulting sequences comprise a T7 promoter an SP6 start site, a start codon, an ESB, a COB and optionally a region encoding a His(6) tag (FIG. 11). The T7 promoter and SP6 start site can be incorporated into the sequence linked to the ESB, using the same method that is used to incorporated the ESB. Alternatively, these sequences can be incorporated withing the last APS. Optionally, a His(6) tag encoding region can be incorporated linked to the final APS or to the ESB.

The assembled ESB-linked COBs are transcribed and translated into peptide sequences using the Expressway™ Maxi Cell-Free *E. coli* Expression System (Invitrogen). The peptide sequences are isolated using affinity chromatography and/or HPLC prior to being sequenced using a tandem mass spectrometer.

Prophetic Example 6. Split-Pool Synthesis of COBs on Cell Surfaces

Cell surface receptors on leukocyte cell lines (HL60, JY and U937) are detected and quantified using split-pool synthesis of COBs on cell surfaces. Using Antibody-Oligonucleotide All-in-One Conjugation Kit (Solulink), antibodies against CD1, CD3, CD8 and CD4 are conjugated with amine modified CL oligonucleotides described in Example 3. The singly-labeled antibodies are isolated using affinity chromatography using complementary oligonucleotides targeting a sequence in CL oligonucleotides and the number of labels on each antibody is verified using mass spectrometry. A cell suspension of $10^7$ cells are incubated with the combination of the antibodies under suitable conditions followed by 6 rounds of split-pool synthesis. The resulting ESB-linked COBs are detected as described in Example 3 or Example 4. The detected signals related to COB-linked ESBs are quantified for each COB combination. Co-expression of each of the CD1, CD3, CD8, and CD4 antigens on the cells are plotted pairwise. Principle component analysis is used to identify the strongest correlations in expression profiles.

Prophetic Example 7. Split-Pool Synthesis of COBs in Cells

Methanol is cooled to $-20°$ C. A cell culture comprising $10^7$ HeLa cells is grown using suitable tissue culture conditions known in the art. The growth medium is removed by aspiration. The cells are immediately fixed and permeabilized by adding 50 mL cold methanol. The cells are allowed to incubate at ambient temperature for 10 minutes with gentle shaking. Methanol is carefully removed by aspiration. The cells are rinsed with 100 mL of 1×PBS, three times.

The cells are blocked with 150 ml of 0.1% Casein solution in 0.2% PBS for 1.5 hrs at room temperature by gentle shaking. Rabbit anti-cleaved caspase-3, rabbit anti phos-p38, rabbit anti-phos-ERK2, mouse anti-ERK2, and mouse anti-β-tubulin (clone AA2) are CL-conjugated as described in Example 5. Cells are incubated with CL-conjugated antibodies overnight at 4° C., gently shaking. The cells are washed 5 times with 1×PBS+0.1% Tween-20 for 5 minutes at room temperature, followed by 6 rounds of split-pool synthesis.

The resulting ESB-linked COBs are detected as described in Example 3 or Example 4. The detected signals related to COB-linked ESBs are quantified for each COB combination. Co-expression of each of the Phospho-p53, ERK1 in the cells are plotted pairwise. Principle component analysis is used to identify the strongest correlations in expression profiles.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
   (a) labeling a population of cells or cell organelles with a binding agent-oligonucleotide conjugate that comprises a binding agent and an oligonucleotide, wherein the oligonucleotide comprises:
      (i) a first primer binding region, and
      (ii) an epitope-specific barcode that identifies the binding agent to which the oligonucleotide is conjugated, and
   (b) adding cell-specific barcodes onto the oligonucleotide by a split-pool barcoding process.

2. The method of claim 1, wherein the oligonucleotide of the conjugate further comprises:
   (iii) a random or degenerate sequence.

3. The method of claim 1, wherein the method further comprises adding a random or degenerate sequence onto the oligonucleotide during or after the split-pool barcoding process.

4. The method of claim 1, wherein step (a) comprises labeling the population of cells or cell organelles with:
   the first binding agent-oligonucleotide conjugate, and
   a second binding agent-oligonucleotide conjugate that comprises a binding agent and an oligonucleotide,
   wherein the binding agents of the first and second conjugates bind to different target molecules in or on the cells or cell organelles.

5. The method of claim 1, wherein step (a) comprises labeling the population of cells or cell organelles with at least 10 of the binding agent-oligonucleotide conjugates, each binding to a different target molecule.

6. The method of claim 1, wherein the split-pool barcoding process of (b) comprises at least one round of:
   splitting the cells or cell organelles into multiple reaction volumes;
   appending barcode subunits onto the oligonucleotide in the reaction volumes, wherein a plurality of the reaction volumes each receive a different barcode subunit; and
   pooling the reaction volumes.

7. The method of claim 1, wherein the split-pool barcoding process of (b) comprises at least two rounds of:
   splitting the cells or cell organelles into multiple reaction volumes;
   appending barcode subunits onto the oligonucleotide in the reaction volumes, wherein a plurality of the reaction volumes each receive a different barcode subunit; and
   pooling the reaction volumes.

8. The method of claim 7, wherein the cells or cell organelles are split into at least 12 reaction volumes in each of the at least two rounds.

9. The method of claim 1, wherein the method comprises:
   labeling the population of cells or cell organelles with the binding agent-oligonucleotide conjugate in a first reaction volume;
   separating the cells or cell organelles into a plurality of second reaction volumes, wherein at least some of the second reaction volumes receive a single cell or cell organelle from the population of cells or cell organelles;
   adding the cell-specific barcodes onto the oligonucleotide or complement thereof in the second reaction volumes; and then
   pooling the second reaction volumes.

10. The method of claim 9, wherein the second reaction volumes are droplets, wells, or enclosures in a microfluidics device.

11. The method of claim 1, wherein the binding agent is an antibody, peptide, aptamer, peptoid or nucleic acid.

12. The method of claim 1, wherein the binding agent binds to a target molecule that is on the surface of a cell.

13. The method of claim 1, wherein the binding agent binds to a target molecule that is intracellular.

14. The method of claim 1, wherein the population of cells or cell organelles is a cell suspension, cultured cells, blood cells, or cells from a tissue.

15. The method of claim 1, wherein the population of cells or cell organelles is from a sample of blood cells.

16. The method of claim 1, wherein the adding is done by ligation, gap-fill/ligation, by extension by a polymerase, hybridization or affinity binding.

17. The method of claim 1, wherein the binding agent binds to RNA or DNA in or on the cells or cell organelles.

18. The method of claim 1, wherein the binding agent binds to a protein in or on the cells or cell organelles.

19. The method of claim 1, wherein the method further comprises:
   adding an amplification primer binding region to the oligonucleotide or complement thereof, and
   amplifying a nucleic acid comprising the epitope-specific barcode and the cell-specific barcodes to produce an amplification product.

20. The method of claim 19, further comprising sequencing the amplification product.

21. The method of claim 1, wherein the cells or cell organelles are fixed and permeabilized prior to step (a).

22. The method of claim 1, wherein the method is performed on cells that have been exposed to an agent or genetically modified.

23. The method of claim 9, wherein the cells or cell organelles are lysed in the second reaction volumes prior to adding the cell-specific barcodes onto the oligonucleotides.

24. The method of claim 9, wherein the method is performed on cells.

25. The method of claim 9, wherein the method is performed on cell organelles.

26. The method of claim 7, wherein the barcode subunits are appended directly or indirectly onto the oligonucleotide in the reaction volumes, by ligation, gap-fill/ligation, by extension by a polymerase, hybridization or affinity binding.

* * * * *